US010059747B2

(12) United States Patent
Buttigieg et al.

(10) Patent No.: US 10,059,747 B2
(45) Date of Patent: Aug. 28, 2018

(54) CRIMEAN-CONGO HAEMORRHAGIC FEVER VIRUS ANTIGENIC COMPOSITION

(71) Applicant: THE SECRETARY OF STATE FOR HEALTH, London (GB)

(72) Inventors: Karen Buttigieg, Salisbury (GB); Mile Carroll, Salisbury (GB); Roger Hewson, Salisbury (GB); Stuart Dowall, Salisbury (GB); Stephen Findlay-Wilson, Salisbury (GB); Aleksandra Miloszewska, Salisbury (GB)

(73) Assignee: THE SECRETARY OF STATE FOR HEALTH, London (GB)

( * ) Notice: Subject to any disclaimer, the term of this patent is extended or adjusted under 35 U.S.C. 154(b) by 0 days.

(21) Appl. No.: 14/763,622

(22) PCT Filed: Nov. 29, 2013

(86) PCT No.: PCT/GB2013/053174
§ 371 (c)(1),
(2) Date: Jul. 27, 2015

(87) PCT Pub. No.: WO2014/132013
PCT Pub. Date: Sep. 4, 2014

(65) Prior Publication Data
US 2015/0361141 A1     Dec. 17, 2015

(30) Foreign Application Priority Data

Feb. 26, 2013    (GB) .................................. 1303406.1

(51) Int. Cl.
| | |
|---|---|
| *C07K 14/005* | (2006.01) |
| *A61K 39/12* | (2006.01) |
| *C12N 15/86* | (2006.01) |
| *C12N 7/00* | (2006.01) |
| *A61K 39/00* | (2006.01) |

(52) U.S. Cl.
CPC ............ *C07K 14/005* (2013.01); *A61K 39/12* (2013.01); *C12N 7/00* (2013.01); *C12N 15/86* (2013.01); *A61K 39/00* (2013.01); *A61K 2039/523* (2013.01); *A61K 2039/5256* (2013.01); *A61K 2039/53* (2013.01); *A61K 2039/545* (2013.01); *C12N 2710/10341* (2013.01); *C12N 2710/24041* (2013.01); *C12N 2710/24141* (2013.01); *C12N 2760/12034* (2013.01)

(58) Field of Classification Search
CPC ...... A61K 2039/523; A61K 2039/5252; A61K 2039/5254; A61K 39/12; C12N 15/86; C12N 2710/10341; C12N 2710/24041; C12N 2710/24141; C12N 2760/12034; C12N 2760/12221; C12N 2760/12234; C12N 2760/18134; C12N 2760/18143; C12N 2510/02; C12N 2760/12022; C12N 10/24041; C12N 10/24141; C07K 14/005
See application file for complete search history.

(56) References Cited

U.S. PATENT DOCUMENTS

| | | | |
|---|---|---|---|
| 8,741,653 B2 * | 6/2014 | Leyrer | .................. C12N 15/86 435/235.1 |
| 2009/0123494 A1 | 5/2009 | Staplin et al. | |
| 2012/0014988 A1 | 1/2012 | Hausmann et al. | |

FOREIGN PATENT DOCUMENTS

| | | | |
|---|---|---|---|
| WO | WO2010072365 A1 * | 7/2010 | |
| WO | 2011059334 A1 | 5/2011 | |

OTHER PUBLICATIONS

Sanchez et al. Journal of Virology, 2002, 76 (14), 7263-7275.*
Souza et al. (Brazilian Journal of Medical Biological Research 2005, vol. 38, pp. 509-522).*
Ghiasi et al. "Miche Orally Immunized with a Transgenic Plant Expressing the Glycoprotein of Crimean-Congo Hemorrhagic Fever Virus." Clin. Vaccine Immunol. 18(12):2031-2037 (2013).
Keshtkar-Jahromi et al. "Crimean-Congo hemorrhagic fever: Current and future prospects of vaccines and therapies." Antiviral Research vol. 90, pp. 85-92 (2011).
Sahib et al. "Rapid Development of Optimized Recombinant Adenoviral Vaccines for Biosafety Level 4 Viruses." http://search.proquest.com/docview/853333121—UMI Dissertations Publishing (2010) pp. 1-159.
Spik et al. "Immunogenicity of combination DNA vaccines for Rift Valley fever virus, tick-borne encephalitis virus, Hantaan virus, and Crimean Congo hemorrhagic fever virus." Vaccine vol. 24, pp. 4657-4666 (2006).
International Search Report for PCT/GB2013/053174 dated Feb. 27, 2014 (3 pages).
Blanchard, "Curriculum Vitae," (witnessed May 31, 2016) United Kingdom, pp. 1-8.
Blanchard, "Declaration by Dr. Thomas Blanchard," The Tropical and Infectious Disease Unit, (witnessed May 31, 2016) United Kingdom, pp. 1-3.
Dowall et al., "A Crimean-Congo hemorrhagic fever (CCHF) viral vaccine expressing nucleoprotein is immunogenic but fails to confer protection against lethal disease," Human Vaccines & Immunotherapeutics 12:2, 519-527, (Feb. 2016).
Dowall et al., "A Crimean-Congo hemorrhagic fever (CCHF) viral vaccine expressing nucleoprotein is immunogenic but fails to confer protection against lethal disease," Human Vaccines & Immunotherapeutics 12:2, 519-527, (2016).

(Continued)

*Primary Examiner* — Bao Q Li
(74) *Attorney, Agent, or Firm* — Merchant & Gould P.C.

(57) ABSTRACT

The present invention provides a viral vector or bacterial vector, said vector comprising a nucleic acid sequence encoding a Crimean-Congo Haemorrhagic Fever Virus (CCHFV) glycoprotein or antigenic fragment thereof; wherein said vector is capable of inducing an immune response in a subject. The present invention also provides compositions and uses of the vector in methods of medical treatment.

13 Claims, 25 Drawing Sheets
Specification includes a Sequence Listing.

(56) References Cited

OTHER PUBLICATIONS

Henikoff et al., "Amino acid substitution matrices from protein blocks", Biochemistry, Proc. Natl, Acad. Sci. USA 89:10915-10919 (1992).
Sahib et al., "Rapid Development of Adenovirus-Based Vaccines Against Emerging/Re-Emerging Biosafety Level 4 Viruses", Adenovirus Vector Biology, 118, Molecular Therapy vol. 17, Supplement 1:S46 (2009).
Buttigieg et al., "A Novel Vaccine against Crimean-Congo Haemorrhagic Fever Protects 100% of Animals against Lethal Challenge in a Mouse Model", PLOS one, 9(3), e91516:1-14 (2014).
Search Report for British Patent Application No. 1303406.1, dated Aug. 15, 2013.
Office Action for European Patent Application No. 13802091.2, dated Mar. 29, 2017.
Written Opinion (ISA/237) for PCT/GB2013/053174, dated Feb. 27, 2014.
Written Opinion (IPEA/408) for PCT/GB2013/053174, dated May 28, 2015.

* cited by examiner

Summed antigen response to
CCHF glycoprotein peptides
(mean + SD)

SEQUENCE LISTING

```
<160> NUMBER OF SEQ ID NOS: 7

<210> SEQ ID NO 1
<211> LENGTH: 5055
<212> TYPE: DNA
<213> ORGANISM: Crimean-Congo hemorrhagic fever virus

<400> SEQUENCE: 1
atgcatatat cattaatgta tgcaatcctt tgcctacagc tgtgtggtct gggagagact      60
catggatcac acaatgaaac tagacacaat aaaacagaca ccatgacaac acacggtgat     120
aacccgagct ctgaaccgcc agtgagcacg gccttgtcta ttacacttga cccctccact     180
gtcacaccca caaccagc cagtggatta gaaggctcag gggaagtcta cacatcccct      240
ccgatcacca ccgggagctt gcccctgtcg gagacaacac cagaactccc tgttacaacc     300
ggcacagaca ccttaagcgc aggtgatgtc gatcccagca cgcagacagc cggaggcacc     360
tccgcaccaa cagtccgcac aagtctaccc aacagcccta gcacaccatc tacaccacaa     420
gacacacacc atcctgtgag aaatctactt tcagtcacga gtcctgggcc agatgaaaca     480
tcaacaccct cgggaacagg caaagagagc tcagcaacca gtagccctca tccagtctcc     540
aacagaccac caacccctcc tgcaacagcc cagggaccca ctgaaaatga cagtcacaac     600
gccactgaac accctgagtc cctgacacag tcagcaaccc caggcctaat gacctctcca     660
acacagatag tccacccaca aagtgccacc cccataaccg ttcaagacac acatcccagt     720
ccaacgaaca ggtctaaaag aaaccttaag atggaaataa tcttgacttt atctcagggt     780 ttaaaaagt actatgggaa aatattaagg cttctgcaac tcaccttaga ggaggacact     840
gaaggtctac tggaatggtg taagagaaat cttggtcttg attgtgatga cactttcttt     900
caaaagagaa ttgaagaatt ctttataact ggtgagggcc attttaatga agttttacaa     960
tttagaacgc caggcacgtt gagcaccaca gagtcaacac ctgctgggct gccaacagct    1020 gaaccttta agtcctactt cgccaaaggc ttcctctcga tagattcagg ttactactca    1080
gccaaatgtt actcaggaac atccaattca gggcttcaat tgattaacat tacccgacat    1140
tcaactagaa tagttgacac acctgggcct aagatcacta acctaaagac catcaactgc    1200
ataaacttga aggcatcgat cttcaaagaa catagagagg ttgaaatcaa tgtgcttctc    1260
ccccaagttg cagttaatct ctcaaactgt acgttgtaa tcaaatcaca tgtctgtgac    1320
tactctttag acattgacgg tgcggtgagg cttcctcaca tttaccatga aggagttttc    1380
```

```
atcccaggaa cttacaaaat agtgatagat aaaaaaaata agttgaatga cagatgcacc      1440
ttatttaccg actgtgtgat aaaaggaagg gaggttcgta aaggacagtc agttttgagg      1500
cagtacaaga cggaaatcag gattggcaag gcatcaaccg gctttagaag attgctttca      1560
gaagaaccca gtgatgactg tgtatcaaga actcaactat taaggacaga gactgcagag      1620
atccacggcg acaactatgg tggcccgggt gacaaaataa ccatctgcaa tggctcaact      1680
attgtagacc aaagactggg cagtgaacta ggatgctaca ccatcaatag agtgaggtca      1740
ttcaagctat gcgaaaacag tgccacaggg aagaattgtg aaatagacag tgtcccagtt      1800
aaatgcaggc agggttattg cctaagaatc actcaggaag ggaggggcca cgtaaaatta      1860 tctagggggct cagaggttgt cttagatgca tgcgatacaa gctgtgaaat aatgatacct      1920
aagggcactg gtgacatcct agttgactgt tcaggtgggc agcaacattt tctaaaggac      1980
aatttgatag atctaggatg ccccaaaatt ccattattgg gcaaaatggc tatttacatt      2040
tgcagaatgt caaccaccc caaacaacc atggctttcc tcttctggtt cagctttggc      2100
tatgtaataa cctgcatact ttgcaaggct atttttttact tgttaataat tgttggaaca      2160
ctagggagaa ggctcaagca gtatagagag ttgaaacctc agacttgcac catatgtgag      2220
acaactcctg taaatgcaat agatgctgag atgcatgacc tcaattgcag ttacaacatt      2280 tgtcccctact gtgcatctag actaacctca gatgggcttg ctaggcatgt gatacaatgc      2340
cctaagcgga aggagaaagt ggaagaaact gaactgtact tgaacttaga aagaattcct      2400
tgggttgtaa gaaagctgtt gcaggtgtca gagtcaactg gtgtggcatt gaaaagaagc      2460
agttggctga ttgtgctgct tgtgctattc actgtttcat tatcaccagt tcaatcagca      2520
cccattggtc aagggaagac aattgaggca taccgggcca gggaagggta cacaagtata      2580
tgcctctttg tactaggaag tatcctattt atagtttctt gcctaatgaa agggctggtt      2640
gacagtgttg gcaactcctt cttccctgga ctgtccattt gcaaaacgtg ctccataagc      2700
agcattaatg gctttgaaat tgagtcccat aagtgctatt gcagcttatt ctgttgcccc      2760
tattgtaggc actgctctac cgataaagaa attcataagc tgcacttgag catctgcaaa      2820
aaaaggaaaa caggaagtaa tgtcatgttg gctgtctgca agctcatgtg tttcagggcc      2880
accatggaag taagtaacag agccctgttt atccgtagca tcatcaacac cacttttgtt      2940
ttgtgcatac tgatactagc agtttgtgtt gttagcacct cagcagtgga gatgaaaac      3000 ctaccagcag ggacctggga agagaagaa gacctaacaa atttctgtca tcaggaatgc      3060
caggttacag agactgaatg cctctgccct tatgaagctc tagtactcag aaagccttta      3120
ttcctagata gtacagctaa aggcatgaaa atctgctaa attcaacaag tttagaaacg      3180
agtttatcaa ttgaggcacc atgggagca ataaatgttc agtcaaccta caaaccaact      3240
gtgtcaactg caaacatagc actcagttgg agctcagtgg aacacagagg caataagatc      3300
ttggtttcag gcagatcaga atcaattatg aagctggaag aaaggacagg aatcagctgg      3360
gatctcggtg tagaagatgc ctctgaatct aaactgctta cagtatctgt catggacttg      3420
tctcagatgt actctcctgt cttcgagtac ttatcagggg acagacaggt ggaagagtgg      3480
cccaaagcaa cttgcacagg tgactgccca gaaagatgtg gctgcacatc atcaacctgt      3540
ttgcacaaag aatggcctca ctcaagaaat tggagatgca atcccacttg gtgctgggt      3600 gtagggactg gctgcacctg ttgtgggatta gatgtgaaag accttttac agattatatg      3660 tttgtcaagt ggaagttga atacatcaag acagaggcca tagtgtgtgt agaacttact      3720
agtcaggaaa ggcagtgtag cttgattgaa gcgggcacaa ggttcaattt aggtcctgtg      3780
```

```
accatcacac tgtcagaacc aagaaacatc caacaaaaac tccctcctga aataatcaca    3840
ctgcatccta ggatcgaaga aggttttttt gacctgatgc atgtgcaaaa ggtgttatcg    3900
gcaagcacag tgtgtaagtt gcagagttgc acacatggtg tgccaggaga cctacaggtc    3960
taccacatcg gaaatttatt aaaggggat aaggtaaatg acatctaat tcataaaatt     4020 gagccacact tcaacacctc ctggatgtcc tgggatggtt gtgacctaga ctactactgc    4080
aacatgggag attggccttc ttgcacatac acaggggtca cccaacacaa tcatgcttca    4140
tttgtaaact tactcaacat tgaaactgat tacacaaaga acttccactt tcactctaaa    4200
agggtcactg cacacggaga taccacacaa ctagatctta aggcaagacc aacctatggt    4260
gcaggcgaga tcactgttct ggtagaagtt gctgacatgg agttacatac aaagaagatt    4320
gaaatatcag gcttaaaatt tgcaagctta gcttgcacag gttgttatgc ttgtagctct    4380
agcatctcat gcaaagttag aattcatgtg gatgaaccag atgaacttac agtacatgtt    4440
aaaagtgatg atccagatgt ggttgcagct agctcaagtc tcatggcaag gaagcttgaa    4500
tttggaacag acagtacatt taaagctttc tcggccatgc ctaaaacttc tctatgtttc    4560
tacattgttg aaagagaaca ctgtaagagc tgcagtgaag aagacacaaa aaatgtgtt    4620 aacacaaaac ttgagcaacc acaaagcatt ttgatcgaac acaagggaac tataatcgga    4680
aagcaaaaca gcacttgcac ggctaaggca agttgctggt tagagtcagt caagagtttt    4740
ttttatggcc taagaacat gcttagtggc atttttggca atgtctttat gggcattttc    4800
ttgttccttg ccccttcat cctgttaata ctattcttta tgtttgggtg gaggatccta    4860
ttctgcttta aatgttgtag aagaaccaga ggcctgttca agtatagaca cctcaaagac    4920
gatgaagaaa ctggttatag aaggattatt gaaaaactaa acaataaaaa aggaaaaaac    4980
aaactgcttg atggtgaaag acttgctgat ggaagaattg ccgaactgtt ctctacaaaa    5040
acacacattg gctag                                                    5055

<210> SEQ ID NO 2
<211> LENGTH: 876
<212> TYPE: DNA
<213> ORGANISM: Crimean-Congo hemorrhagic fever virus

<400> SEQUENCE: 2
agaagattgc tttcagaaga acccagtgat gactgtgtat caagaactca actattaagg      60
acagagactg cagagatcca cggcgacaac tatggtggcc cgggtgacaa ataaccatc      120 tgcaatggct caactattgt agaccaaaga ctgggcagtg aactaggatg ctacaccatc     180
aatagagtga ggtcattcaa gctatgcgaa acagtgcca cagggaagaa ttgtgaaata      240
gacagtgtcc cagttaaatg caggcagggt tattgcctaa gaatcactca ggaagggagg     300
ggccacgtaa aattatctag gggctcagag gttgtcttag atgcatgcga tacaagctgt     360
gaaataatga tacctaaggg cactggtgac atcctagttg actgttcagg tgggcagcaa     420
cattttctaa aggacaattt gatagatcta ggatgcccca aaattccatt attgggcaaa     480
atggctattt acatttgcag aatgtcaaac caccccaaaa caaccatggc tttcctcttc     540
tggttcagct ttggctatgt aataacctgc atactttgca aggctatttt ttacttgtta     600
ataattgttg gaacactagg gagaaggctc aagcagtata gagagttgaa acctcagact     660
tgcaccatat gtgagacaac tcctgtaaat gcaatagatg ctgagatgca tgacctcaat     720
tgcagttaca catttgtcc ctactgtgca tctagactaa cctcagatgg gcttgctagg     780
```

| | |
|---|---:|
| catgtgatac aatgccctaa gcggaaggag aaagtggaag aaactgaact gtacttgaac | 840 |
| ttagaaagaa ttccttgggt tgtaagaaag ctgttg | 876 |

<210> SEQ ID NO 3
<211> LENGTH: 1947
<212> TYPE: DNA
<213> ORGANISM: Crimean-Congo hemorrhagic fever virus

<400> SEQUENCE: 3

| | |
|---|---:|
| agaaagcctt tattcctaga tagtacagct aaaggcatga aaaatctgct aaattcaaca | 60 |
| agtttagaaa cgagtttatc aattgaggca ccatggggag caataaatgt tcagtcaacc | 120 |
| tacaaaccaa ctgtgtcaac tgcaaacata gcactcagtt ggagctcagt ggaacacaga | 180 |
| ggcaataaga tcttggtttc aggcagatca gaatcaatta tgaagctgga agaaaggaca | 240 |
| ggaatcagct gggatctcgg tgtagaagat gcctctgaat ctaaactgct tacagtatct | 300 |
| gtcatggact tgtctcagat gtactctcct gtcttcgagt acttatcagg ggacagacag | 360 |
| gtggaagagt ggcccaaagc aacttgcaca ggtgactgcc cagaaagatg tggctgcaca | 420 |
| tcatcaacct gtttgcacaa gaatggcct cactcaagaa attggagatg caatcccact | 480 |
| tggtgctggg gtgtagggac tggctgcacc tgttgtggat tagatgtgaa agaccttttt | 540 |
| acagattata tgtttgtcaa gtggaaagtt gaatacatca agacagaggc catagtgtgt | 600 |
| gtagaactta ctagtcagga aaggcagtgt agcttgattg aagcgggcac aaggttcaat | 660 |
| ttaggtcctg tgaccatcac actgtcagaa ccaagaaaca tccaacaaaa actccctcct | 720 |
| gaaataatca cactgcatcc taggatcgaa gaagttttt tgacctgat gcatgtgcaa | 780 |
| aaggtgttat cggcaagcac agtgtgtaag ttgcagagtt gcacacatgg tgtgccagga | 840 |
| gacctacagg tctaccacat cggaaattta ttaaaagggg ataaggtaaa tggacatcta | 900 |
| attcataaaa ttgagccaca cttcaacacc tcctggatgt cctgggatgg ttgtgaccta | 960 |
| gactactact gcaacatggg agattggcct tcttgcacat acacaggggt cacccaacac | 1020 |
| aatcatgctt catttgtaaa cttactcaac attgaaactg attacacaaa gaacttccac | 1080 |
| tttcactcta aagggtcac tgcacacgga gatacaccac aactagatct taaggcaaga | 1140 |
| ccaacctatg gtgcaggcga gatcactgtt ctggtagaag ttgctgacat ggagttacat | 1200 |
| acaaagaaga ttgaaatatc aggcttaaaa tttgcaagct agcttgcac aggttgttat | 1260 |
| gcttgtagct ctagcatctc atgcaaagtt agaattcatg tggatgaacc agatgaactt | 1320 |
| acagtacatg ttaaaagtga tgatccagat gtggttgcag ctagctcaag tctcatggca | 1380 |
| aggaagcttg aatttggaac agacagtaca tttaaagctt tctcggccat gcctaaaact | 1440 |
| tctctatgtt tctacattgt tgaaagagaa cactgtaaga gctgcagtga agaagacaca | 1500 |
| aaaaaatgtg ttaacacaaa acttgagcaa ccacaaagca ttttgatcga acacaaggga | 1560 |
| actataatcg gaaagcaaaa cagcacttgc acggctaagg caagttgctg gttagagtca | 1620 |
| gtcaagagtt ttttttatgg cctaaagaac atgcttagtg gcattttgg caatgtcttt | 1680 |
| atgggcattt tcttgttcct tgccccttc atcctgttaa tactattctt tatgtttggg | 1740 |
| tggaggatcc tattctgctt taaatgttgt agaagaacca gaggcctgtt caagtataga | 1800 |
| cacctcaaag acgatgaaga aactggttat agaaggatta ttgaaaaact aaacaataaa | 1860 |
| aaaggaaaaa acaaactgct tgatggtgaa agacttgctg atggaagaat tgccgaactg | 1920 |
| ttctctacaa aaacacacat tggctag | 1947 |

<210> SEQ ID NO 4
<211> LENGTH: 1684
<212> TYPE: PRT
<213> ORGANISM: Crimean-Congo hemorrhagic fever virus

<400> SEQUENCE: 4

```
Met His Ile Ser Leu Met Tyr Ala Ile Leu Cys Leu Gln Leu Cys Gly
1               5                   10                  15

Leu Gly Glu Thr His Gly Ser His Asn Glu Thr Arg His Asn Lys Thr
            20                  25                  30

Asp Thr Met Thr Thr His Gly Asp Asn Pro Ser Ser Glu Pro Pro Val
        35                  40                  45

Ser Thr Ala Leu Ser Ile Thr Leu Asp Pro Ser Thr Val Thr Pro Thr
    50                  55                  60

Thr Pro Ala Ser Gly Leu Glu Gly Ser Gly Glu Val Tyr Thr Ser Pro
65                  70                  75                  80

Pro Ile Thr Thr Gly Ser Leu Pro Leu Ser Glu Thr Thr Pro Glu Leu
                85                  90                  95

Pro Val Thr Thr Gly Thr Asp Thr Leu Ser Ala Gly Asp Val Asp Pro
            100                 105                 110

Ser Thr Gln Thr Ala Gly Gly Thr Ser Ala Pro Thr Val Arg Thr Ser
        115                 120                 125

Leu Pro Asn Ser Pro Ser Thr Pro Ser Thr Pro Gln Asp Thr His His
130                 135                 140

Pro Val Arg Asn Leu Leu Ser Val Thr Ser Pro Gly Pro Asp Glu Thr
145                 150                 155                 160

Ser Thr Pro Ser Gly Thr Gly Lys Glu Ser Ser Ala Thr Ser Ser Pro
                165                 170                 175

His Pro Val Ser Asn Arg Pro Pro Thr Pro Pro Ala Thr Ala Gln Gly
            180                 185                 190

Pro Thr Glu Asn Asp Ser His Asn Ala Thr Glu His Pro Glu Ser Leu
        195                 200                 205

Thr Gln Ser Ala Thr Pro Gly Leu Met Thr Ser Pro Thr Gln Ile Val
    210                 215                 220

His Pro Gln Ser Ala Thr Pro Ile Thr Val Gln Asp Thr His Pro Ser
225                 230                 235                 240

Pro Thr Asn Arg Ser Lys Arg Asn Leu Lys Met Glu Ile Ile Leu Thr
                245                 250                 255

Leu Ser Gln Gly Leu Lys Lys Tyr Tyr Gly Lys Ile Leu Arg Leu Leu
            260                 265                 270

Gln Leu Thr Leu Glu Glu Asp Thr Glu Gly Leu Leu Glu Trp Cys Lys
        275                 280                 285

Arg Asn Leu Gly Leu Asp Cys Asp Asp Thr Phe Phe Gln Lys Arg Ile
290                 295                 300

Glu Glu Phe Phe Ile Thr Gly Glu Gly His Phe Asn Glu Val Leu Gln
305                 310                 315                 320

Phe Arg Thr Pro Gly Thr Leu Ser Thr Thr Glu Ser Thr Pro Ala Gly
                325                 330                 335

Leu Pro Thr Ala Glu Pro Phe Lys Ser Tyr Phe Ala Lys Gly Phe Leu
            340                 345                 350

Ser Ile Asp Ser Gly Tyr Tyr Ser Ala Lys Cys Tyr Ser Gly Thr Ser
        355                 360                 365

Asn Ser Gly Leu Gln Leu Ile Asn Ile Thr Arg His Ser Thr Arg Ile
    370                 375                 380
```

```
Val Asp Thr Pro Gly Pro Lys Ile Thr Asn Leu Lys Thr Ile Asn Cys
385                 390                 395                 400

Ile Asn Leu Lys Ala Ser Ile Phe Lys Glu His Arg Glu Val Glu Ile
                405                 410                 415

Asn Val Leu Leu Pro Gln Val Ala Val Asn Leu Ser Asn Cys His Val
            420                 425                 430

Val Ile Lys Ser His Val Cys Asp Tyr Ser Leu Asp Ile Asp Gly Ala
        435                 440                 445

Val Arg Leu Pro His Ile Tyr His Glu Gly Val Phe Ile Pro Gly Thr
    450                 455                 460

Tyr Lys Ile Val Ile Asp Lys Lys Asn Lys Leu Asn Asp Arg Cys Thr
465                 470                 475                 480

Leu Phe Thr Asp Cys Val Ile Lys Gly Arg Glu Val Arg Lys Gly Gln
                485                 490                 495

Ser Val Leu Arg Gln Tyr Lys Thr Glu Ile Arg Ile Gly Lys Ala Ser
            500                 505                 510

Thr Gly Phe Arg Arg Leu Leu Ser Glu Glu Pro Ser Asp Asp Cys Val
        515                 520                 525

Ser Arg Thr Gln Leu Leu Arg Thr Glu Thr Ala Glu Ile His Gly Asp
530                 535                 540

Asn Tyr Gly Gly Pro Gly Asp Lys Ile Thr Ile Cys Asn Gly Ser Thr
545                 550                 555                 560

Ile Val Asp Gln Arg Leu Gly Ser Glu Leu Gly Cys Tyr Thr Ile Asn
                565                 570                 575

Arg Val Arg Ser Phe Lys Leu Cys Glu Asn Ser Ala Thr Gly Lys Asn
            580                 585                 590

Cys Glu Ile Asp Ser Val Pro Val Lys Cys Arg Gln Gly Tyr Cys Leu
        595                 600                 605

Arg Ile Thr Gln Glu Gly Arg Gly His Val Lys Leu Ser Arg Gly Ser
610                 615                 620

Glu Val Val Leu Asp Ala Cys Asp Thr Ser Cys Glu Ile Met Ile Pro
625                 630                 635                 640

Lys Gly Thr Gly Asp Ile Leu Val Asp Cys Ser Gly Gly Gln Gln His
                645                 650                 655

Phe Leu Lys Asp Asn Leu Ile Asp Leu Gly Cys Pro Lys Ile Pro Leu
            660                 665                 670

Leu Gly Lys Met Ala Ile Tyr Ile Cys Arg Met Ser Asn His Pro Lys
        675                 680                 685

Thr Thr Met Ala Phe Leu Phe Trp Phe Ser Phe Gly Tyr Val Ile Thr
690                 695                 700

Cys Ile Leu Cys Lys Ala Ile Phe Tyr Leu Leu Ile Ile Val Gly Thr
705                 710                 715                 720

Leu Gly Arg Arg Leu Lys Gln Tyr Arg Glu Leu Lys Pro Gln Thr Cys
                725                 730                 735

Thr Ile Cys Glu Thr Thr Pro Val Asn Ala Ile Asp Ala Glu Met His
            740                 745                 750

Asp Leu Asn Cys Ser Tyr Asn Ile Cys Pro Tyr Cys Ala Ser Arg Leu
        755                 760                 765

Thr Ser Asp Gly Leu Ala Arg His Val Ile Gln Cys Pro Lys Arg Lys
770                 775                 780

Glu Lys Val Glu Glu Thr Glu Leu Tyr Leu Asn Leu Glu Arg Ile Pro
785                 790                 795                 800

Trp Val Val Arg Lys Leu Leu Gln Val Ser Glu Ser Thr Gly Val Ala
```

-continued

Leu Lys Arg Ser Ser Trp Leu Ile Val Leu Val Leu Phe Thr Val
805                 810                 815

Ser Leu Ser Pro Val Gln Ser Ala Pro Ile Gly Gln Gly Lys Thr Ile
    820                 825                 830

Glu Ala Tyr Arg Ala Arg Glu Gly Tyr Thr Ser Ile Cys Leu Phe Val
    835                 840                 845

Leu Gly Ser Ile Leu Phe Ile Val Ser Cys Leu Met Lys Gly Leu Val
850                 855                 860

Asp Ser Val Gly Asn Ser Phe Phe Pro Gly Leu Ser Ile Cys Lys Thr
865                 870                 875                 880

Cys Ser Ile Ser Ser Ile Asn Gly Phe Glu Ile Glu Ser His Lys Cys
                885                 890                 895

Tyr Cys Ser Leu Phe Cys Cys Pro Tyr Cys Arg His Cys Ser Thr Asp
            900                 905                 910

Lys Glu Ile His Lys Leu His Leu Ser Ile Cys Lys Lys Arg Lys Thr
        915                 920                 925

Gly Ser Asn Val Met Leu Ala Val Cys Lys Leu Met Cys Phe Arg Ala
    930                 935                 940

Thr Met Glu Val Ser Asn Arg Ala Leu Phe Ile Arg Ser Ile Ile Asn
945                 950                 955                 960

Thr Thr Phe Val Leu Cys Ile Leu Ile Leu Ala Val Cys Val Val Ser
                965                 970                 975

Thr Ser Ala Val Glu Met Glu Asn Leu Pro Ala Gly Thr Trp Glu Arg
            980                 985                 990

Glu Glu Asp Leu Thr Asn Phe Cys His Gln Glu Cys Gln Val Thr
        995                 1000                1005

Glu Thr Glu Cys Leu Cys Pro Tyr Glu Ala Leu Val Leu Arg Lys
    1010                1015                1020

Pro Leu Phe Leu Asp Ser Thr Ala Lys Gly Met Lys Asn Leu Leu
    1025                1030                1035

Asn Ser Thr Ser Leu Glu Thr Ser Leu Ser Ile Glu Ala Pro Trp
    1040                1045                1050

Gly Ala Ile Asn Val Gln Ser Thr Tyr Lys Pro Thr Val Ser Thr
    1055                1060                1065

Ala Asn Ile Ala Leu Ser Trp Ser Ser Val Glu His Arg Gly Asn
    1070                1075                1080

Lys Ile Leu Val Ser Gly Arg Ser Glu Ser Ile Met Lys Leu Glu
    1085                1090                1095

Glu Arg Thr Gly Ile Ser Trp Asp Leu Gly Val Glu Asp Ala Ser
    1100                1105                1110

Glu Ser Lys Leu Leu Thr Val Ser Val Met Asp Leu Ser Gln Met
    1115                1120                1125

Tyr Ser Pro Val Phe Glu Tyr Leu Ser Gly Asp Arg Gln Val Glu
    1130                1135                1140

Glu Trp Pro Lys Ala Thr Cys Thr Gly Asp Cys Pro Glu Arg Cys
    1145                1150                1155

Gly Cys Thr Ser Ser Thr Cys Leu His Lys Glu Trp Pro His Ser
    1160                1165                1170

Arg Asn Trp Arg Cys Asn Pro Thr Trp Cys Trp Gly Val Gly Thr
    1175                1180                1185

Gly Cys Thr Cys Cys Gly Leu Asp Val Lys Asp Leu Phe Thr Asp
    1190                1195                1200

-continued

```
Tyr Met Phe Val Lys Trp Lys Val Glu Tyr Ile Lys Thr Glu Ala
    1220            1225                1230

Ile Val Cys Val Glu Leu Thr Ser Gln Glu Arg Gln Cys Ser Leu
    1235            1240                1245

Ile Glu Ala Gly Thr Arg Phe Asn Leu Gly Pro Val Thr Ile Thr
    1250            1255                1260

Leu Ser Glu Pro Arg Asn Ile Gln Gln Lys Leu Pro Pro Glu Ile
    1265            1270                1275

Ile Thr Leu His Pro Arg Ile Glu Glu Gly Phe Phe Asp Leu Met
    1280            1285                1290

His Val Gln Lys Val Leu Ser Ala Ser Thr Val Cys Lys Leu Gln
    1295            1300                1305

Ser Cys Thr His Gly Val Pro Gly Asp Leu Gln Val Tyr His Ile
    1310            1315                1320

Gly Asn Leu Leu Lys Gly Asp Lys Val Asn Gly His Leu Ile His
    1325            1330                1335

Lys Ile Glu Pro His Phe Asn Thr Ser Trp Met Ser Trp Asp Gly
    1340            1345                1350

Cys Asp Leu Asp Tyr Tyr Cys Asn Met Gly Asp Trp Pro Ser Cys
    1355            1360                1365

Thr Tyr Thr Gly Val Thr Gln His Asn His Ala Ser Phe Val Asn
    1370            1375                1380

Leu Leu Asn Ile Glu Thr Asp Tyr Thr Lys Asn Phe His Phe His
    1385            1390                1395

Ser Lys Arg Val Thr Ala His Gly Asp Thr Pro Gln Leu Asp Leu
    1400            1405                1410

Lys Ala Arg Pro Thr Tyr Gly Ala Gly Glu Ile Thr Val Leu Val
    1415            1420                1425

Glu Val Ala Asp Met Glu Leu His Thr Lys Lys Ile Glu Ile Ser
    1430            1435                1440

Gly Leu Lys Phe Ala Ser Leu Ala Cys Thr Gly Cys Tyr Ala Cys
    1445            1450                1455

Ser Ser Ser Ile Ser Cys Lys Val Arg Ile His Val Asp Glu Pro
    1460            1465                1470

Asp Glu Leu Thr Val His Val Lys Ser Asp Asp Pro Asp Val Val
    1475            1480                1485

Ala Ala Ser Ser Ser Leu Met Ala Arg Lys Leu Glu Phe Gly Thr
    1490            1495                1500

Asp Ser Thr Phe Lys Ala Phe Ser Ala Met Pro Lys Thr Ser Leu
    1505            1510                1515

Cys Phe Tyr Ile Val Glu Arg Glu His Cys Lys Ser Cys Ser Glu
    1520            1525                1530

Glu Asp Thr Lys Lys Cys Val Asn Thr Lys Leu Glu Gln Pro Gln
    1535            1540                1545

Ser Ile Leu Ile Glu His Lys Gly Thr Ile Ile Gly Lys Gln Asn
    1550            1555                1560

Ser Thr Cys Thr Ala Lys Ala Ser Cys Trp Leu Glu Ser Val Lys
    1565            1570                1575

Ser Phe Phe Tyr Gly Leu Lys Asn Met Leu Ser Gly Ile Phe Gly
    1580            1585                1590

Asn Val Phe Met Gly Ile Phe Leu Phe Leu Ala Pro Phe Ile Leu
    1595            1600                1605
```

```
Leu Ile Leu Phe Phe Met Phe Gly Trp Arg Ile Leu Phe Cys Phe
    1610            1615                1620

Lys Cys Cys Arg Arg Thr Arg Gly Leu Phe Lys Tyr Arg His Leu
    1625            1630                1635

Lys Asp Asp Glu Glu Thr Gly Tyr Arg Arg Ile Ile Glu Lys Leu
    1640            1645                1650

Asn Asn Lys Lys Gly Lys Asn Lys Leu Leu Asp Gly Glu Arg Leu
    1655            1660                1665

Ala Asp Gly Arg Ile Ala Glu Leu Phe Ser Thr Lys Thr His Ile
    1670            1675                1680

Gly

<210> SEQ ID NO 5
<211> LENGTH: 292
<212> TYPE: PRT
<213> ORGANISM: Crimean-Congo hemorrhagic fever virus

<400> SEQUENCE: 5

Arg Arg Leu Leu Ser Glu Glu Pro Ser Asp Asp Cys Val Ser Arg Thr
1               5                   10                  15

Gln Leu Leu Arg Thr Glu Thr Ala Glu Ile His Gly Asp Asn Tyr Gly
            20                  25                  30

Gly Pro Gly Asp Lys Ile Thr Ile Cys Asn Gly Ser Thr Ile Val Asp
        35                  40                  45

Gln Arg Leu Gly Ser Glu Leu Gly Cys Tyr Thr Ile Asn Arg Val Arg
    50                  55                  60

Ser Phe Lys Leu Cys Glu Asn Ser Ala Thr Gly Lys Asn Cys Glu Ile
65                  70                  75                  80

Asp Ser Val Pro Val Lys Cys Arg Gln Gly Tyr Cys Leu Arg Ile Thr
                85                  90                  95

Gln Glu Gly Arg Gly His Val Lys Leu Ser Arg Gly Ser Glu Val Val
            100                 105                 110

Leu Asp Ala Cys Asp Thr Ser Cys Glu Ile Met Ile Pro Lys Gly Thr
        115                 120                 125

Gly Asp Ile Leu Val Asp Cys Ser Gly Gly Gln His Phe Leu Lys
    130                 135                 140

Asp Asn Leu Ile Asp Leu Gly Cys Pro Lys Ile Pro Leu Leu Gly Lys
145                 150                 155                 160

Met Ala Ile Tyr Ile Cys Arg Met Ser Asn His Pro Lys Thr Thr Met
                165                 170                 175

Ala Phe Leu Phe Trp Phe Ser Phe Gly Tyr Val Ile Thr Cys Ile Leu
            180                 185                 190

Cys Lys Ala Ile Phe Tyr Leu Leu Ile Ile Val Gly Thr Leu Gly Arg
        195                 200                 205

Arg Leu Lys Gln Tyr Arg Glu Leu Lys Pro Gln Thr Cys Thr Ile Cys
    210                 215                 220

Glu Thr Thr Pro Val Asn Ala Ile Asp Ala Glu Met His Asp Leu Asn
225                 230                 235                 240

Cys Ser Tyr Asn Ile Cys Pro Tyr Cys Ala Ser Arg Leu Thr Ser Asp
                245                 250                 255

Gly Leu Ala Arg His Val Ile Gln Cys Pro Lys Arg Lys Glu Lys Val
            260                 265                 270

Glu Glu Thr Glu Leu Tyr Leu Asn Leu Glu Arg Ile Pro Trp Val Val
        275                 280                 285
```

Arg Lys Leu Leu
    290

<210> SEQ ID NO 6
<211> LENGTH: 648
<212> TYPE: PRT
<213> ORGANISM: Crimean-Congo hemorrhagic fever virus

<400> SEQUENCE: 6

Arg Lys Pro Leu Phe Leu Asp Ser Thr Ala Lys Gly Met Lys Asn Leu
1               5                   10                  15

Leu Asn Ser Thr Ser Leu Glu Thr Ser Leu Ser Ile Glu Ala Pro Trp
            20                  25                  30

Gly Ala Ile Asn Val Gln Ser Thr Tyr Lys Pro Thr Val Ser Thr Ala
        35                  40                  45

Asn Ile Ala Leu Ser Trp Ser Ser Val Glu His Arg Gly Asn Lys Ile
    50                  55                  60

Leu Val Ser Gly Arg Ser Glu Ser Ile Met Lys Leu Glu Glu Arg Thr
65                  70                  75                  80

Gly Ile Ser Trp Asp Leu Gly Val Glu Asp Ala Ser Glu Ser Lys Leu
                85                  90                  95

Leu Thr Val Ser Val Met Asp Leu Ser Gln Met Tyr Ser Pro Val Phe
            100                 105                 110

Glu Tyr Leu Ser Gly Asp Arg Gln Val Glu Glu Trp Pro Lys Ala Thr
        115                 120                 125

Cys Thr Gly Asp Cys Pro Glu Arg Cys Gly Cys Thr Ser Ser Thr Cys
    130                 135                 140

Leu His Lys Glu Trp Pro His Ser Arg Asn Trp Arg Cys Asn Pro Thr
145                 150                 155                 160

Trp Cys Trp Gly Val Gly Thr Gly Cys Thr Cys Cys Gly Leu Asp Val
                165                 170                 175

Lys Asp Leu Phe Thr Asp Tyr Met Phe Val Lys Trp Lys Val Glu Tyr
            180                 185                 190

Ile Lys Thr Glu Ala Ile Val Cys Val Glu Leu Thr Ser Gln Glu Arg
        195                 200                 205

Gln Cys Ser Leu Ile Glu Ala Gly Thr Arg Phe Asn Leu Gly Pro Val
    210                 215                 220

Thr Ile Thr Leu Ser Glu Pro Arg Asn Ile Gln Gln Lys Leu Pro Pro
225                 230                 235                 240

Glu Ile Ile Thr Leu His Pro Arg Ile Glu Glu Gly Phe Phe Asp Leu
                245                 250                 255

Met His Val Gln Lys Val Leu Ser Ala Ser Thr Val Cys Lys Leu Gln
            260                 265                 270

Ser Cys Thr His Gly Val Pro Gly Asp Leu Gln Val Tyr His Ile Gly
        275                 280                 285

Asn Leu Leu Lys Gly Asp Lys Val Asn Gly His Leu Ile His Lys Ile
    290                 295                 300

Glu Pro His Phe Asn Thr Ser Trp Met Ser Trp Asp Gly Cys Asp Leu
305                 310                 315                 320

Asp Tyr Tyr Cys Asn Met Gly Asp Trp Pro Ser Cys Thr Tyr Thr Gly
                325                 330                 335

Val Thr Gln His Asn His Ala Ser Phe Val Asn Leu Leu Asn Ile Glu
            340                 345                 350

Thr Asp Tyr Thr Lys Asn Phe His Phe His Ser Lys Arg Val Thr Ala
        355                 360                 365

His Gly Asp Thr Pro Gln Leu Asp Leu Lys Ala Arg Pro Thr Tyr Gly
    370                 375                 380

Ala Gly Glu Ile Thr Val Leu Val Glu Val Ala Asp Met Glu Leu His
385                 390                 395                 400

Thr Lys Lys Ile Glu Ile Ser Gly Leu Lys Phe Ala Ser Leu Ala Cys
                405                 410                 415

Thr Gly Cys Tyr Ala Cys Ser Ser Ser Ile Ser Cys Lys Val Arg Ile
            420                 425                 430

His Val Asp Glu Pro Asp Glu Leu Thr Val His Val Lys Ser Asp Asp
        435                 440                 445

Pro Asp Val Val Ala Ala Ser Ser Leu Met Ala Arg Lys Leu Glu
    450                 455                 460

Phe Gly Thr Asp Ser Thr Phe Lys Ala Phe Ser Ala Met Pro Lys Thr
465                 470                 475                 480

Ser Leu Cys Phe Tyr Ile Val Glu Arg Glu His Cys Lys Ser Cys Ser
                485                 490                 495

Glu Glu Asp Thr Lys Lys Cys Val Asn Thr Lys Leu Glu Gln Pro Gln
            500                 505                 510

Ser Ile Leu Ile Glu His Lys Gly Thr Ile Ile Gly Lys Gln Asn Ser
        515                 520                 525

Thr Cys Thr Ala Lys Ala Ser Cys Trp Leu Glu Ser Val Lys Ser Phe
    530                 535                 540

Phe Tyr Gly Leu Lys Asn Met Leu Ser Gly Ile Phe Gly Asn Val Phe
545                 550                 555                 560

Met Gly Ile Phe Leu Phe Leu Ala Pro Phe Ile Leu Leu Ile Leu Phe
                565                 570                 575

Phe Met Phe Gly Trp Arg Ile Leu Phe Cys Phe Lys Cys Cys Arg Arg
            580                 585                 590

Thr Arg Gly Leu Phe Lys Tyr Arg His Leu Lys Asp Asp Glu Glu Thr
        595                 600                 605

Gly Tyr Arg Arg Ile Ile Glu Lys Leu Asn Asn Lys Lys Gly Lys Asn
    610                 615                 620

Lys Leu Leu Asp Gly Glu Arg Leu Ala Asp Gly Arg Ile Ala Glu Leu
625                 630                 635                 640

Phe Ser Thr Lys Thr His Ile Gly
                645

<210> SEQ ID NO 7
<211> LENGTH: 7620
<212> TYPE: DNA
<213> ORGANISM: Artificial Sequence
<220> FEATURE:
<223> OTHER INFORMATION: MVA-GP nucleic acid sequence

<400> SEQUENCE: 7
gttggtggtc gccatggatg gtgttattgt atactgtcta aacgcgttag taaaacatgg     60
cgaggaaata atcatataa aaaatgattt catgattaaa ccatgttgtg aaaaagtcaa    120
gaacgttcac attggcggac aatctaaaaa caatacagtg attgcagatt tgccatatat    180
ggataatgcg gtatccgatg tatgcaattc actgtataaa aagaatgtat caagaatatc    240
cagatttgct aatttgataa agatagatga cgatgacaag actcctactg gtgtatataa    300
ttattttaaa cctaaagatg ccattcctgt tattatatcc ataggaaagg atagagatgt    360
tgtgaactta ttaatctcat ctgataaagc gtgtgcgtgt atagagttaa attcatataa    420

```
agtagccatt cttcccatgg atgtttcctt ttttaccaaa ggaaatgcat cattgattat      480
tctcctgttt gatttctcta tcgatgcggc acctctctta agaagtgtaa ccgataataa      540
tgttattata tctagacacc agcgtctaca tgacgagctt ccgagttcca attggttcaa      600
gttttacata agtataaagt ccgactattg ttctatatta tatatggttg ttgatggatc      660
tgtgatgcat gcaatagctg ataatagaac ttacgcaaat attagcaaaa atatattaga      720
caatactaca attaacgatg agtgtagatg ctgttatttt gaaccacaga ttaggattct      780
tgatagagat gagatgctca atggatcatc gtgtgatatg aacagacatt gtattatgat      840
gaatttacct gatgtaggcg aatttggatc tagtatgttg gggaaatatg aacctgacat      900
gattaagatt gctcttcgg tggctgggta ccaggcgcgc ctttcatttt gtttttttct       960
atgctataaa tggtgagcaa gggcgaggag ctgttcaccg gggtggtgcc catcctggtc     1020
gagctggacg gcgacgtaaa cggccacaag ttcagcgtgt ccggcgaggg cgagggcgat     1080
gccacctacg gcaagctgac cctgaagttc atctgcacca ccggcaagct gcccgtgccc     1140
tggcccaccc tcgtgaccac cctgacctac ggcgtgcagt gcttcagccg ctaccccgac     1200
cacatgaagc agcacgactt cttcaagtcc gccatgcccg aaggctacgt ccaggagcgc     1260
accatcttct tcaaggacga cggcaactac aagacccgcg ccgaggtgaa gttcgagggc     1320
gacaccctgg tgaaccgcat cgagctgaag ggcatcgact tcaaggagga cggcaacatc     1380
ctggggcaca agctggagta caactacaac agccacaacg tctatatcat ggccgacaag     1440
cagaagaacg gcatcaaggt gaacttcaag atccgccaca acatcgagga cggcagcgtg     1500
cagctcgccg accactacca gcagaacacc cccatcggcg acggccccgt gctgctgccc     1560
gacaaccact acctgagcac ccagtccgcc ctgagcaaag accccaacga gaagcgcgat     1620
cacatggtcc tgctggagtt cgtgaccgcc gccgggatca ctctcggcat gcacgagctg     1680
tacaagtaag cggccgctgg tacccaacct aaaaattgaa aataaataca aggttcttg      1740 agggttgtgt taaattgaaa gcagaaaata atcataaata agcccggtgc caccatggat     1800
gcaatgaaga gagggctctg ctgtgtgctg ctgctgtgtg gagcagtctt cgtttcgccc     1860
agccaggaaa tccatgcccg attcagaaga ggagccagat ctcccatcaa acaagtttgt     1920
acaaaaaagc aggctcatat atcattaatg tatgcaatcc tttgcctaca gctgtgtggt     1980 ctggagaga ctcatggatc acacaatgaa actagacaca ataaaacaga caccatgaca      2040
acacacggtg ataacccgag ctctgaaccg ccagtgagca cggccttgtc tattacactt     2100
gacccctcca ctgtcacacc cacaacacca gccagtggat tagaaggctc aggggaagtc     2160
tacacatccc ctccgatcac caccgggagc ttgcccctgt cggagacaac accagaactc     2220
cctgttacaa ccggcacaga caccttaagc gcaggtgatg tcgatcccag cacgcagaca     2280
gccggaggca cctccgcacc aacagtccgc acaagtctac ccaacagccc tagcacacca     2340
tctacaccac aagacacaca ccatcctgtg agaaatctac tttcagtcac gagtcctggg     2400
ccagatgaaa catcaacacc ctcgggaaca ggcaaagaga gctcagcaac cagtagccct     2460
catccagtct ccaacagacc accaaccccct cctgcaacag cccagggacc cactgaaaat     2520
gacagtcaca acgccactga cacccctgag tccctgacac agtcagcaac cccaggccta     2580
atgacctctc caacacagat agtccaccca caaagtgcca cccccataac cgttcaagac     2640
acacatccca gtccaacgaa caggtctaaa agaaacctta agatggaaat aatcttgact     2700
ttatctcagg gtttaaaaaa gtactatggg aaaaattaaa ggcttctgca actcaccttá     2760 gaggaggaca ctgaaggtct actggaatgg tgtaagagaa atcttggtct tgattgtgat     2820
```

```
gacactttct tcaaaagag aattgaagaa ttctttataa ctggtgaggg ccattttaat    2880
gaagttttac aatttagaac gccaggcacg ttgagcacca cagagtcaac acctgctggg    2940
ctgccaacag ctgaaccttt taagtcctac ttcgccaaag gcttcctctc gatagattca    3000
ggttactact cagccaaatg ttactcagga acatccaatt cagggcttca attgattaac    3060
attacccgac attcaactag aatagttgac acacctgggc ctaagatcac taacctaaag    3120
accatcaact gcataaactt gaaggcatcg atcttcaaag aacatagaga ggttgaaatc    3180
aatgtgcttc tcccccaagt tgcagttaat ctctcaaact gtcacgttgt aatcaaatca    3240
catgtctgtg actactcttt agacattgac ggtgcggtga ggcttcctca catttaccat    3300
gaaggagttt tcatcccagg aacttacaaa atagtgatag ataaaaaaaa taagttgaat    3360
gacagatgca ccttatttac cgactgtgtg ataaaaggaa gggaggttcg taaggacag     3420
tcagttttga ggcagtacaa gacggaaatc aggattggca aggcatcaac cggctttaga    3480
agattgcttt cagaagaacc cagtgatgac tgtgtatcaa gaactcaact attaaggaca    3540
gagactgcag agatccacgg cgacaactat ggtggcccgg gtgacaaaat aaccatctgc    3600
aatggctcaa ctattgtaga ccaaagactg ggcagtgaac taggatgcta caccatcaat    3660
agagtgaggt cattcaagct atgcgaaaac agtgccacag ggaagaattg tgaaatagac    3720
agtgtcccag ttaaatgcag gcagggttat tgcctaagaa tcactcagga agggaggggc    3780
cacgtaaaat tatctagggg ctcagaggtt gtcttagatg catgcgatac aagctgtgaa    3840
ataatgatac ctaagggcac tggtgacatc ctagttgact gttcaggtgg gcagcaacat    3900
tttctaaagg acaatttgat agatctagga tgccccaaaa ttccattatt gggcaaaatg    3960
gctatttaca tttgcagaat gtcaaaccac cccaaaacaa ccatggcttt cctcttctgg    4020
ttcagctttg gctatgtaat aacctgcata cttttgcaagg ctatttttta cttgttaata    4080
attgttggaa cactagggag aaggctcaag cagtatagag agttgaaacc tcagacttgc    4140
accatatgtg agacaactcc tgtaaatgca atagatgctg agatgcatga cctcaattgc    4200
agttacaaca tttgtccta ctgtgcatct agactaaccct cagatgggct tgctaggcat    4260
gtgatacaat gccctaagcg gaaggagaaa gtggaagaaa ctgaactgta cttgaactta    4320
gaaagaattc cttgggttgt aagaaagctg ttgcaggtgt cagagtcaac tggtgtggca    4380
ttgaaaagaa gcagttggct gattgtgctg cttgtgctat tcactgtttc attatcacca    4440
gttcaatcag cacccattgg tcaagggaag acaattgagg cataccgggc cagggaaggg    4500
tacacaagta tatgcctctt tgtactagga agtatcctat ttatagtttc ttgcctaatg    4560
aaagggctgg ttgacagtgt tggcaactcc ttcttccctg gactgtccat ttgcaaaacg    4620
tgctccataa gcagcattaa tggctttgaa attgagtccc ataagtgcta ttgcagctta    4680
ttctgttgcc cctattgtag gcactgctct accgataaag aaattcataa gctgcacttg    4740
agcatctgca aaaaaggaa aacaggaagt aatgtcatgt tggctgtctg caagctcatg    4800
tgtttcaggg ccaccatgga agtaagtaac agagccctgt ttatccgtag catcatcaac    4860
accacttttg ttttgtgcat actgatacta gcagtttgtg ttgttagcac ctcagcagtg    4920
gagatggaaa acctaccagc agggacctgg gaaagagaag aagacctaac aaatttctgt    4980
catcaggaat gccaggttac agagactgaa tgcctctgcc cttatgaagc tctagtactc    5040
agaaagcctt tattcctaga tagtacagct aaaggcatga aaaatctgct aaattcaaca    5100
agtttagaaa cgagtttatc aattgaggca ccatgggag caataaatgt tcagtcaacc    5160
```

```
tacaaaccaa ctgtgtcaac tgcaaacata gcactcagtt ggagctcagt ggaacacaga    5220
ggcaataaga tcttggtttc aggcagatca gaatcaatta tgaagctgga agaaaggaca    5280
ggaatcagct gggatctcgg tgtagaagat gcctctgaat ctaaactgct tacagtatct    5340
gtcatggact tgtctcagat gtactctcct gtcttcgagt acttatcagg ggacagacag    5400
gtggaagagt ggcccaaagc aacttgcaca ggtgactgcc cagaaagatg tggctgcaca    5460
tcatcaacct gtttgcacaa agaatggcct cactcaagaa attggagatg caatcccact    5520
tggtgctggg gtgtagggac tggctgcacc tgttgtggat tagatgtgaa agaccttttt    5580
acagattata tgtttgtcaa gtggaaagtt gaatacatca agacagaggc catagtgtgt    5640
gtagaactta ctagtcagga aaggcagtgt agcttgattg aagcgggcac aaggttcaat    5700
ttaggtcctg tgaccatcac actgtcagaa ccaagaaaca tccaacaaaa actccctcct    5760
gaaataatca cactgcatcc taggatcgaa gaaggtttct ttgacctgat gcatgtgcaa    5820
aaggtgttat cggcaagcac agtgtgtaag ttgcagagtt gcacacatgg tgtgccagga    5880
gacctacagg tctaccacat cggaaattta ttaaaagggg ataaggtaaa tggacatcta    5940
attcataaaa ttgagccaca cttcaacacc tcctggatgt cctgggatgg ttgtgaccta    6000
gactactact gcaacatggg agattggcct tcttgcacat acacaggggt cacccaacac    6060
aatcatgctt catttgtaaa cttactcaac attgaaactg attacacaaa gaacttccac    6120
tttcactcta aagggtcac tgcacacgga gatacaccac aactagatct taaggcaaga    6180
ccaacctatg gtgcaggcga gatcactgtt ctggtagaag ttgctgacat ggagttacat    6240
acaaagaaga ttgaaatatc aggcttaaaa tttgcaagct tagcttgcac aggttgttat    6300
gcttgtagct ctagcatctc atgcaaagtt agaattcatg tggatgaacc agatgaactt    6360
acagtacatg ttaaaagtga tgatccagat gtggttgcag ctagctcaag tctcatggca    6420
aggaagcttg aatttggaac agacagtaca tttaaagctt tctcggccat gcctaaaact    6480
tctctatgtt tctacattgt tgaaagagaa cactgtaaga gctgcagtga agaagacaca    6540
aaaaaatgtg ttaacacaaa acttgagcaa ccacaaagca ttttgatcga acacaaggga    6600
actataatcg gaaagcaaaa cagcacttgc acggctaagg caagttgctg gttagagtca    6660
gtcaagagtt tcttttatgg cctaagaac atgcttagtg gcattttttgg caatgtcttt    6720 atgggcattt tcttgttcct tgccccccttc atcctgttaa tactattctt tatgtttggg    6780
tggaggatcc tattctgctt taaatgttgt agaagaacca gaggcctgtt caagtataga    6840
cacctcaaag acgatgaaga aactggttat agaaggatta ttgaaaaact aaacaataaa    6900
aaaggaaaaa acaaactgct tgatggtgaa agacttgctg atggaagaat tgccgaactg    6960
ttctctacaa aaacacacat tggcacccag ctttcttgta caaagtggtt cgatggggat    7020
ctagagggcc cgcggttcga aggtaagcct atccctaacc ctctcctcgg tctcgattct    7080
acgtaagtcg acctgcaggg aaagttttat aggtagttga tagaacaaaa tacataattt    7140
tgtaaaaata aatcacttttt tatactaata tgacacgatt accaatactt tgttactaa    7200 tatcattagt atacgctaca ccttttcctc agacatctaa aaaataggt gatgatgcaa    7260 ctttatcatg taatcgaaat aatacaaatg actacgttgt tatgagtgct tggtataagg    7320
agcccaattc cattattctt ttagctgcta aaagcgacgt cttgtatttt gataattata    7380
ccaaggataa aatatcttac gactctccat acgatgatct agttacaact atcacaatta    7440
```

```
aatcattgac tgctagagat gccggtactt atgtatgtgc attctttatg acatcgccta    7500
caaatgacac tgataaagta gattatgaag aatactccac agagttgatt gtaaatacag    7560
atagtgaatc gactatagac ataatactat ctggatctac acattcacca gaaactagtt    7620
```

CRIMEAN-CONGO HAEMORRHAGIC FEVER VIRUS ANTIGENIC COMPOSITION

This application is a National Stage Application of PCT/GB2013/053174, filed 29 Nov. 2013, which claims benefit of Serial No. 1303406.1, filed 26 Feb. 2013 in Great Britain and which applications are incorporated herein by reference. To the extent appropriate, a claim of priority is made to each of the above disclosed applications.

BACKGROUND

The present invention relates to viral vectors and bacterial vectors comprising Crimean-Congo Haemorrhagic Fever Virus (CCHFV) antigens and their use in immunogenic and antigenic compositions.

Crimean-Congo Haemorrhagic fever (CCHF) is a viral haemorrhagic fever caused by a virus of the *Nairovirus* group (CCHFV). CCHF is a zoonosis, and infects a range of domestic and wild animals. It is spread via the bite of an infected tick. CCHF was first described in the Crimea in 1944 among soldiers and agricultural workers, and in 1969 it was recognised that the virus causing the disease was identical to a virus isolated from a child in the Congo in 1956.

CCHF virus is endemic in many countries in Africa, the Middle East, Eastern Europe and Asia, and outbreaks have been recorded in Russia, Turkey, Iran, Kazakhstan, Mauritania, Kosovo, Albania, Pakistan, and southern Africa in recent years. The first clinical case of CCHF in Greece was reported in July 2008. The global distribution of cases corresponds to those areas where the ticks are found.

The virus is spread by the bite of infected *Ixodidae* ticks, and the most efficient and common vectors appear to be members of the *Hyalomma* genus, which commonly infest livestock and other animals. Immature ticks acquire the virus by feeding on infected small animals. Once infected, the tick carries the virus for life, and passes it to animals or humans when it bites them. Domestic ruminants such as cattle, sheep and goats carry the virus for around one week after becoming infected. Most birds are thought to be relatively resistant to infection with CCHF virus, however, many bird species carry *Hyalomma* ticks, and human cases have occurred in those working with ostriches in the past.

Humans may be infected with CCHF by the bite of an infected tick, contamination with tick body contents, or direct contact with the blood, tissues or body fluids of infected humans or animals. The majority of cases occur in those living in tick infested areas with occupational exposure to livestock, including farmers, veterinarians, slaughterhouse workers, livestock owners and others working with animals. Cases also occur in healthcare workers or others caring for infected persons without taking adequate infection control precautions.

CCHF outbreaks are generally associated with a change in situation such as war, population and animal movements, or climatic and vegetation changes which produce more ground cover for small mammals which act as hosts for ticks. These conditions can lead to explosions in tick populations, and allow increased tick/human contact.

The incubation period of CCHF appears to vary according to the mode of acquisition of the virus. If a patient has been infected by a tick bite, the incubation period is usually 1-3 days, and up to 9 days. Infection via contact with infected blood or tissues leads to an incubation period of 5-6 days, and the maximum recorded incubation period is 13 days. The illness begins abruptly, with fever, muscle aches, dizziness, neck pain and stiffness, backache, headache, sore eyes and photophobia (sensitivity to light). Nausea, vomiting and sore throat may also occur, with diarrhoea and abdominal pain. Over the next few days the patient may experience mood swings, confusion and aggression, followed by sleepiness, depression and liver enlargement. More severe symptoms may follow, including petechial rash (a rash caused by bleeding into the skin), bruising and generalised bleeding of the gums and orifices. In severe cases patients develop failure of the liver, kidneys and lungs, and become drowsy and comatose after 5 days. Approximately 30% of cases are fatal.

Diagnosis of CCHF requires highly specialised, high biosafety level laboratory facilities. Antibodies may be detected in serum by about day six of illness. The virus may be isolated from blood or tissue specimens in the first five days of illness, and grown in cell culture, and nucleic acid detection methods may also be used to detect the viral genome. Patients with fatal disease do not usually develop a detectable antibody response, and in these individuals, and those in the early stages of infection, diagnosis is by virus detection. General supportive therapy is given, including replacement of blood components, balancing fluids and electrolytes, and maintaining oxygen status and blood pressure. There is evidence that CCHF responds to treatment with the antiviral drug ribavirin, in both oral and intravenous formulations.

A vaccine based on inactivated CCHF virus has been used in Eastern Europe, however this vaccine is not licensed by the EMA or FDA, and there is no literature to demonstrate its efficacy. There is therefore at present no safe and effective, commercially-available vaccine against CCHFV.

There is therefore a need for new vaccine compositions that demonstrate improved immunogenicity when used in the prevention and treatment of CCHFV infections, in particular in human subjects.

SUMMARY AND DETAILED DESCRIPTION

The present invention addresses one or more of the above problems by providing viral vectors and bacterial vectors encoding CCHFV glycoproteins or antigenic fragments thereof, together with corresponding compositions and uses of said vectors and compositions in the prevention and treatment of CCHFV infection.

The vectors and compositions of the invention enable an immune response against CCHFV to be stimulated (i.e. induced) in an individual (i.e. a subject), and provide improved immunogenicity and efficacy.

In one aspect, the invention provides a viral vector or bacterial vector, said vector comprising a nucleic acid sequence encoding a Crimean-Congo Haemorrhagic Fever Virus (CCHFV) glycoprotein or antigenic fragment thereof; wherein said vector is capable of inducing an immune response in an individual. The present inventors have found that highly effective immune responses against CCHFV can be generated in an individual by using a viral vector or bacterial vector to deliver to the subject nucleic acid sequences encoding CCHFV glycoproteins (or antigenic fragments thereof), as described above.

In a preferred embodiment, the vector of the invention is a viral vector.

The CCHFV glycoproteins are two proteins $G_N$ and $G_C$, which are encoded by the M segment of the CCHFV genome. A CCHFV virion carries its genome as three single-stranded, negative sense RNA segments, S (small), M (medium) and L (large), which encode a nucleoprotein, a polyprotein, and an RNA-dependent RNA polymerase, respectively. The M segment, which is approximately 5.4 kb in length, encodes a single open reading frame of approximately 1,400 residues which is translated into a polyprotein. This polyprotein is processed by a complex set of proteolytic cleavage events to release a total of four separate proteins: two glycoproteins $G_N$ and $G_C$ and two other domains, a mucin-like domain and a GP35 domain. The CCHFV glycoproteins $G_N$ and $G_C$ are incorporated into the envelope of mature CCHFV virions, and influence host range, cell tropism and pathogenicity. These glycoprotein ecto-domains are the primary CCHFV proteins exposed to the immune system of an infected individual. The remaining two proteins produced from the M segment polyprotein remain in the Golgi apparatus of an infected cell and play a role in chaperoning the maturation of $G_N$ and $G_C$. The CCHFV glycoproteins contain approximately 80 cysteine residues, suggesting the presence of a large number of disulphide bonds and a complex secondary structure. The $G_N$ precursor protein (Pre-$G_N$) contains a highly variable domain at its amino terminus that contains a high proportion of serine, threonine and proline residues, and is predicted to be heavily glycosylated, thus resembling a mucin-like domain present in other viral glycoproteins.

As used herein, the term "antigenic fragment" means a peptide or protein fragment of a CCHFV glycoprotein which retains the ability to induce an immune response in an individual, as compared to the reference CCHFV glycoprotein. An antigenic fragment may therefore include at least one epitope of the reference protein. By way of example, an antigenic fragment of the present invention may comprise (or consist of) a peptide sequence having at least 10, 20, 30, 40 or 50 amino acids, wherein the peptide sequence has at least 80% sequence homology over a corresponding peptide sequence of (contiguous) amino acids of the reference protein. An antigenic fragment may comprise (or consist of) at least 10 consecutive amino acid residues from the sequence of the reference protein (for example, at least 10, 15, 20, 25, 30, 35, 40, 45, 50, 60, 70, 80, 90, 100, 125, 150, 177, 200, 250, 300, 350, 400, 450, 500, 600, 750, 1000, 1250, or 1500 consecutive amino acid residues of said reference protein).

An antigenic fragment of a reference protein may have a common antigenic cross-reactivity and/or substantially the same in vivo biological activity as the reference protein. For example, an antibody capable of binding to an antigenic fragment of a reference protein would also be capable of binding to the reference protein itself. By way of further example, the reference protein and the antigenic fragment thereof may share a common ability to induce a "recall response" of a T lymphocyte (e.g. CD4+, CD8+, effector T cell or memory T cell such as a TEM or TCM), which has been previously exposed to an antigenic component of a CCHFV infection.

In one embodiment, the nucleic acid sequence encoding a CCHFV glycoprotein or antigenic fragment thereof comprises (or consists of) a nucleic acid sequence having at least 70% (such as at least 70, 75, 80, 82, 84, 86, 88, 90, 92, 94, 95, 96, 97, 98, 99 or 100%) sequence identity to a nucleic acid sequence selected from SEQ ID NOs: 1, 2, and 3.

In one embodiment, the nucleic acid sequence encoding a CCHFV glycoprotein or antigenic fragment thereof comprises (or consists of) a nucleic acid sequence having at least 90% (such as at least 90, 92, 94, 95, 96, 97, 98, 99 or 100%) sequence identity to a nucleic acid sequence selected from SEQ ID NOs: 1, 2, and 3. In a further embodiment, the nucleic acid sequence encoding a CCHFV glycoprotein or antigenic fragment thereof comprises (or consists of) a nucleic acid sequence having at least 95% (such as at least 95, 96, 97, 98, 99 or 100%) sequence identity to a nucleic acid sequence selected from SEQ ID NOs: 1, 2, and 3.

The present inventors have found that the CCHFV glycoproteins encoded by the nucleic acid sequences of SEQ ID NOs: 1, 2, and 3 can be used to generate effective immune responses in individuals against CCHFV. In particular, the inventors have found that a highly effective immune response against CCHFV is obtained when one or more members of this group of glycoproteins is delivered to the subject using a bacterial vector or a viral vector, such as a non-replicating poxvirus vector or an adenovirus vector.

The nucleic acid sequence of SEQ ID NO: 1 represents the full-length M segment open reading frame, encoding both $G_N$ and $G_C$ glycoproteins. Thus, in one embodiment, the nucleic acid sequence encoding a CCHFV glycoprotein or antigenic fragment thereof comprises (or consists of) a CCHFV M segment. In one embodiment, a vector of the invention can be used to deliver a full-length M segment to a target cell in a subject, thus leading to production of the polyprotein encoded by the M segment, subsequent processing of which produces both $G_N$ and $G_C$ glycoproteins, thus stimulating an immune response against both $G_N$ and $G_C$ glycoproteins.

The nucleic acid sequence of SEQ ID NO: 2 encodes the $G_N$ glycoprotein. The nucleic acid sequence of SEQ ID NO: 3 encodes the $G_C$ glycoprotein. Thus, in one embodiment, the nucleic acid sequence encoding a CCHFV glycoprotein encodes a CCHFV $G_N$ or a CCHFV $G_C$ glycoprotein. Accordingly, in one embodiment, a vector of the invention can be used to deliver a nucleic acid sequence encoding a CCHFV $G_N$ glycoprotein to a target cell in a subject, stimulating an immune response against said CCHFV $G_N$ glycoprotein. In another embodiment, a vector of the invention can be used to deliver a nucleic acid sequence encoding a CCHFV $G_C$ glycoprotein to a target cell in a subject, stimulating an immune response against said CCHFV $G_C$ glycoprotein.

An immune response against both $G_N$ and $G_C$ glycoproteins may also be generated using a vector comprising a nucleic acid sequence that encodes both $G_N$ and $G_C$ glycoproteins, but which sequence is not the full-length M segment. Thus, in one embodiment, the nucleic acid sequence encoding a CCHFV glycoprotein or antigenic fragment thereof comprises a first nucleic acid sequence having at least 70% (such as at least 70, 75, 80, 82, 84, 86, 88, 90, 92, 94, 95, 96, 97, 98, 99 or 100%) sequence identity to SEQ ID NO: 2, and a second nucleic acid sequence having at least 70% (such as at least 70, 75, 80, 82, 84, 86, 88, 90, 92, 94, 95, 96, 97, 98, 99 or 100%) sequence identity to SEQ ID NO: 3.

In one embodiment, the vector of the invention (as described above) comprises a nucleic acid sequence encoding a CCHFV protein, wherein said CCHFV protein comprises (or consists of) an amino acid sequence having at least 70% (such as at least 70, 75, 80, 82, 84, 86, 88, 90, 92, 94, 95, 96, 97, 98, 99 or 100%) sequence identity to SEQ ID NO: 4. The amino acid sequence of SEQ ID NO: 4 represents the amino acid sequence of the polyprotein encoded by the full-length CCHFV M segment. As said polyprotein encodes $G_C$ and $G_N$, the polyprotein may also be considered to be a CCHFV glycoprotein.

In one embodiment, the vector of the invention (as described above) encodes a CCHFV glycoprotein or antigenic fragment thereof, wherein said CCHFV glycoprotein or antigenic fragment thereof comprises (or consists of) an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 4, 5 and 6. The amino acid sequence of SEQ ID NO: 5 represents the amino acid sequence of the CCHFV $G_N$ protein. The amino acid sequence of SEQ ID NO: 6 represents the amino acid sequence of the CCHFV $G_C$ protein.

In one embodiment, the vector comprises a nucleic acid sequence having at least 70% (such as at least 70, 75, 80, 82, 84, 86, 88, 90, 92, 94, 95, 96, 97, 98, 99 or 100%) sequence identity to the nucleic acid sequence of SEQ ID NO: 7.

Vectors are tools which can be used as vectors for the delivery of genetic material into a target cell. By way of example, viral vectors serve as antigen delivery vehicles and also have the power to activate the innate immune system through binding cell surface molecules that recognise viral elements. A recombinant viral vector can be produced that carries nucleic acid encoding a given antigen. The viral vector can then be used to deliver the nucleic acid to a target cell, where the encoded antigen is produced and then presented to the immune system by the target cell's own molecular machinery. As "non-self", the produced antigen generates an immune response in the target subject.

Viral vectors suitable for use in the present invention include poxvirus vectors (such as non-replicating poxvirus vectors), adenovirus vectors, and influenza virus vectors.

In certain embodiments, a "viral vector" may be a virus-like particle (VLP). VLPs are lipid enveloped particles which contain viral proteins. Certain viral proteins have an inherent ability to self-assemble, and in this process bud out from cellular membranes as independent membrane-enveloped particles. VLPs are simple to purify and can, for example, be used to present viral antigens. VLPs are therefore suitable for use in immunogenic compositions, such as described below. In certain embodiments, a viral vector is not a virus-like particle.

Bacterial vectors can also be used as antigen delivery vehicles. A recombinant bacterial vector can be produced that carries nucleic acid encoding a given antigen. The recombinant bacterial vector may express the antigen on its surface. Following administration to a subject, the bacterial vector colonises antigen-presenting cells (e.g. dendritic cells or macrophages). An antigen-specific immune response is induced. The immune response may be a cellular (T cell) immune response, or may comprise both humoral (e.g. B cell) and cellular (T cell) immune responses. Examples of bacteria suitable for use as recombinant bacterial vectors include *Escherichia coli*, *Shigella*, *Salmonella* (e.g. *S. typhimurium*), and *Listeria* bacteria. In one embodiment, the vector of the invention is a bacterial vector, wherein the bacterium is a Gram-negative bacterium. In one embodiment, the vector of the invention is a bacterial vector selected from an *Escherichia coli* vector, a *Shigella* vector, a *Salmonella* vector and a *Listeria* vector.

Without wishing to be bound by any one particular theory, the inventors believe that antigen delivery using the vectors of the invention stimulates, amongst other responses, a T cell response in the subject. Thus, the inventors believe that one way in which the present invention provides for protection against CCHFV infection is by stimulating T cell responses and the cell-mediated immunity system. In addition, humoral (antibody) based protection can also be achieved.

A viral vector of the invention may be a non-replicating viral vector.

As used herein, a non-replicating viral vector is a viral vector which lacks the ability to productively replicate following infection of a target cell. Thus, the ability of a non-replicating viral vector to produce copies of itself following infection of a target cell (such as a human target cell in an individual undergoing vaccination with a non-replicating viral vector) is highly reduced or absent. Such a viral vector may also be referred to as attenuated or replication-deficient. The cause can be loss/deletion of genes essential for replication in the target cell. Thus, a non-replicating viral vector cannot effectively produce copies of itself following infection of a target cell. Non-replicating viral vectors may therefore advantageously have an improved safety profile as compared to replication-competent viral vectors. A non-replicating viral vector may retain the ability to replicate in cells that are not target cells, allowing viral vector production. By way of example, a non-replicating viral vector (e.g. a non-replicating poxvirus vector) may lack the ability to productively replicate in a target cell such as a mammalian cell (e.g. a human cell), but retain the ability to replicate (and hence allow vector production) in an avian cell (e.g. a chick embryo fibroblast, or CEF, cell).

A viral vector of the invention may be a non-replicating poxvirus vector. Thus, in one embodiment, the viral vector encoding a CCHFV glycoprotein or antigenic fragment thereof is a non-replicating poxvirus vector.

In one embodiment, the non-replicating poxvirus vector is selected from: a Modified Vaccinia virus Ankara (MVA) vector, a NYVAC vaccinia virus vector, a canarypox (AL-VAC) vector, and a fowlpox (FPV) vector. MVA and NYVAC are both attenuated derivatives of vaccinia virus. Compared to vaccinia virus, MVA lacks approximately 26 of the approximately 200 open reading frames.

In a preferred embodiment, the non-replicating poxvirus vector is an MVA vector.

A viral vector of the invention may be an adenovirus vector. Thus, in one embodiment, the viral vector encoding a CCHFV glycoprotein or antigenic fragment thereof is an adenovirus vector.

In one embodiment, the adenovirus vector is a non-replicating adenovirus vector (wherein non-replicating is defined as above). Adenoviruses can be rendered non-replicating by deletion of the E1 or both the E1 and E3 gene regions. Alternatively, an adenovirus may be rendered non-replicating by alteration of the E1 or of the E1 and E3 gene regions such that said gene regions are rendered non-functional. For example, a non-replicating adenovirus may lack a functional E1 region or may lack functional E1 and E3 gene regions. In this way the adenoviruses are rendered replication incompetent in most mammalian cell lines and do not replicate in immunised mammals. Most preferably, both E1 and E3 gene region deletions are present in the adenovirus, thus allowing a greater size of transgene to be inserted. This is particularly important to allow larger antigens to be expressed, or when multiple antigens are to be expressed in a single vector, or when a large promoter sequence, such as the CMV promoter, is used. Deletion of the E3 as well as the E1 region is particularly favoured for recombinant Ad5 vectors. Optionally, the E4 region can also be engineered.

In one embodiment, the adenovirus vector is selected from: a human adenovirus vector, a simian adenovirus vector, a group B adenovirus vector, a group C adenovirus vector, a group E adenovirus vector, an adenovirus 6 vector, a PanAd3 vector, an adenovirus C3 vector, a ChAdY25 vector, an AdC68 vector, and an Ad5 vector.

In one embodiment, wherein the vector is a viral vector, the virus (i.e. viral vector) is not a pseudotyped virus. Thus, in one embodiment, the envelope of the viral vector does not comprise foreign glycoproteins (i.e. glycoproteins that are not native to said viral vector).

In one embodiment, wherein the vector is a viral vector, the vector is not a retrovirus vector.

In one embodiment, wherein the vector is a viral vector, the vector is not a murine leukaemia virus (MLV) vector (for example, a Moloney murine leukaemia virus (MoMLV) vector).

In one embodiment, wherein the vector is a viral vector, the vector is not a Newcastle disease virus (NDV) vector.

In one embodiment, wherein the vector is an adenovirus vector, the adenovirus is not a human adenovirus serotype 5 (AdHu5).

Thus, in one embodiment, wherein the vector is a viral vector, the vector is not a retrovirus vector, a Newcastle disease virus vector, or a human adenovirus serotype 5 vector.

In one embodiment, wherein the vector is an adenovirus vector (such as a human adenovirus serotype 5 (AdHu5) vector), the nucleic acid sequence encoding a Crimean-Congo Haemorrhagic Fever Virus (CCHFV) glycoprotein or antigenic fragment thereof does not comprise a CCHFV M segment. In one embodiment, wherein the vector is an adenovirus vector, the vector is stable, expresses a CCHFV glycoprotein product, and induces a protective immune response in a subject.

The nucleic acid sequences as described above may comprise a nucleic acid sequence encoding a CCHFV glycoprotein wherein said glycoprotein comprises a fusion protein. The fusion protein may comprise a CCHFV glycoprotein polypeptide fused to one or more further polypeptides, for example an epitope tag, another antigen, or a protein that increases immunogenicity (e.g. a flagellin).

In one embodiment, the nucleic acid sequence encoding a CCHFV glycoprotein (as described above) further encodes a Tissue Plasminogen Activator (tPA) signal sequence, and/or a V5 fusion protein sequence. In certain embodiments, the presence of a tPA signal sequence can provide for increased immunogenicity; the presence of a V5 fusion protein sequence can provide for identification of expressed protein by immunolabeling.

In one embodiment, the vector (as described above) further comprises a nucleic acid sequence encoding an adjuvant (for example, a cholera toxin, an *E. coli* lethal toxin, or a flagellin).

A bacterial vector of the invention may be generated by the use of any technique for manipulating and generating recombinant bacteria known in the art.

In another aspect, the invention provides a nucleic acid sequence encoding a viral vector, as described above. Thus, the nucleic acid sequence may encode a non-replicating poxvirus vector as described above. Alternatively, the nucleic acid sequence may encode an adenovirus vector as described above.

The nucleic acid sequence encoding a viral vector (as described above) may be generated by the use of any technique for manipulating and generating recombinant nucleic acid known in the art.

In one aspect, the invention provides a method of making a viral vector (as described above), comprising providing a nucleic acid, wherein the nucleic acid comprises a nucleic acid sequence encoding a vector (as described above); transfecting a host cell with the nucleic acid; culturing the host cell under conditions suitable for the propagation of the vector; and obtaining the vector from the host cell.

As used herein, "transfecting" may mean any non-viral method of introducing nucleic acid into a cell. The nucleic acid may be any nucleic acid suitable for transfecting a host cell. Thus, in one embodiment, the nucleic acid is a plasmid. The host cell may be any cell in which a vector (e.g. a non-replicating poxvirus vector or an adenovirus vector, as described above) may be grown. As used herein, "culturing the host cell under conditions suitable for the propagation of the vector" means using any cell culture conditions and techniques known in the art which are suitable for the chosen host cell, and which enable the vector to be produced in the host cell. As used herein, "obtaining the vector", means using any technique known in the art that is suitable for separating the vector from the host cell. Thus, the host cells may be lysed to release the vector. The vector may subsequently be isolated and purified using any suitable method or methods known in the art.

In one aspect, the invention provides a host cell comprising a nucleic acid sequence encoding a viral vector, as described above. The host cell may be any cell in which a viral vector (e.g. a non-replicating poxvirus vector or an adenovirus vector, as described above) may be grown or propagated. In one embodiment, the host cell is selected from: a 293 cell (also known as a HEK, or human embryonic kidney, cell), a CHO cell (Chinese Hamster Ovary), a CCL81.1 cell, a Vero cell, a HELA cell, a Per.C6 cell, a BHK cell (Baby Hamster Kidney), a primary CEF cell (Chick Embryo Fibroblast), a duck embryo fibroblast cell, a DF-1 cell, or a rat IEC-6 cell.

The present invention also provides compositions comprising vectors as described above.

In one aspect, the invention provides a composition comprising a vector (as described above) and a pharmaceutically-acceptable carrier.

Substances suitable for use as pharmaceutically-acceptable carriers are known in the art. Non-limiting examples of pharmaceutically-acceptable carriers include water, saline, and phosphate-buffered saline. In some embodiments, however, the composition is in lyophilized form, in which case it may include a stabilizer, such as bovine serum albumin (BSA). In some embodiments, it may be desirable to formulate the composition with a preservative, such as thiomersal or sodium azide, to facilitate long term storage. Examples of buffering agents include, but are not limited to, sodium succinate (pH 6.5), and phosphate buffered saline (PBS; pH 7.4).

In addition to a pharmaceutically-acceptable carrier, the composition of the invention can be further combined with one or more of a salt, excipient, diluent, adjuvant, immunoregulatory agent and/or antimicrobial compound.

The composition may be formulated as a neutral or salt form. Pharmaceutically acceptable salts include acid addition salts formed with inorganic acids such as, for example, hydrochloric or phosphoric acids, or with organic acids such as acetic, oxalic, tartaric, maleic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In one embodiment, the composition (as described above) further comprises at least one CCHFV polypeptide antigen (i.e. an antigen present in the composition in the form of a polypeptide). Thus, the composition may comprise both vector and polypeptide. In one embodiment, the polypeptide antigen is a CCHFV glycoprotein, such as CCHFV $G_N$ or CCHFV $G_C$. In one embodiment, the presence of a polypeptide antigen means that, following administration of the composition to a subject, an improved simultaneous T cell and antibody response can be achieved. In one embodiment, the T cell and antibody response achieved surpasses that achieved when either a vector or a polypeptide antigen is used alone.

In one embodiment, the polypeptide antigen is not bonded to the vector. In one embodiment, the polypeptide antigen is a separate component to the vector. In one embodiment, the polypeptide antigen is provided separately from the vector.

In one embodiment, the polypeptide antigen is a variant of the antigen encoded by the vector. In one embodiment, the polypeptide antigen is a fragment of the antigen encoded by the vector. In one embodiment, the polypeptide antigen comprises at least part of a polypeptide sequence encoded by a nucleic acid sequence of the vector. Thus, the polypeptide antigen may correspond to at least part of the antigen encoded by the vector.

In one embodiment, the polypeptide antigen is a CCHFV glycoprotein comprising (or consisting of) an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 5 and 6.

The polypeptide antigen may be the same as (or similar to) that encoded by a nucleic acid sequence of the vector of the composition. Thus, administration of the composition comprising a vector and a polypeptide antigen may be used to achieve an enhanced immune response against a single antigen, wherein said enhanced immune response comprises a combined T cell and an antibody response, as described above.

In one embodiment, a composition of the invention (as described above) further comprises at least one naked DNA (i.e. a DNA molecule that is separate from, and not part of, the viral vector of the invention) encoding a CCHFV glycoprotein or antigenic fragment thereof. In one embodiment, the naked DNA comprises (or consists of) a nucleic acid sequence having at least 70% (such as at least 70, 75, 80, 82, 84, 86, 88, 90, 92, 94, 95, 96, 97, 98, 99 or 100%) sequence identity to a nucleic acid sequence selected from SEQ ID NOs: 1, 2, and 3. In one embodiment, the naked DNA encodes a CCHFV glycoprotein comprising (or consisting of) an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 5 and 6.

In one embodiment, a composition of the invention (as described above) further comprises an adjuvant. Non-limiting examples of adjuvants suitable for use with compositions of the present invention include aluminium phosphate, aluminium hydroxide, and related compounds; monophosphoryl lipid A, and related compounds; outer membrane vesicles from bacteria; oil-in-water emulsions such as MF59; liposomal adjuvants, such as virosomes, Freund's adjuvant and related mixtures; poly-lactid-co-glycolid acid (PLGA) particles; cholera toxin; E. coli lethal toxin; and flagellin.

The vectors and compositions of the invention (as described above) can be employed as vaccines. Thus, a composition of the invention may be a vaccine composition.

As used herein, a vaccine is a formulation that, when administered to an animal subject such as a mammal (e.g. a human, bovine, porcine, ovine, caprine, equine, cervine, canine or feline subject; in particular a human subject), stimulates a protective immune response against an infectious disease. The immune response may be a humoral and/or a cell-mediated immune response. Thus, the vaccine may stimulate B cells and/or T cells.

The term "vaccine" is herein used interchangeably with the terms "therapeutic/prophylactic composition", "immunogenic composition", "formulation", "antigenic composition", or "medicament".

In one aspect, the invention provides a vector (as described above) or a composition (as described above) for use in medicine.

In one aspect, the invention provides a vector (as described above) or a composition (as described above) for use in a method of inducing an immune response in a subject. The immune response may be against a CCHFV antigen (e.g. a CCHFV glycoprotein) and/or a CCHFV infection. Thus, the vectors and compositions of the invention can be used to induce an immune response in a subject against a CCHFV glycoprotein (for example, as immunogenic compositions or as vaccines).

In one embodiment, the immune response comprises a T cell response.

In one embodiment, the method of inducing an immune response in a subject comprises administering to a subject an effective amount of a vector (as described above) or a composition (as described above).

In one aspect, the invention provides a vector (as described above) or a composition (as described above) for use in a method of preventing or treating a CCHFV infection in a subject.

As used herein, the term "preventing" includes preventing the initiation of CCHFV infection and/or reducing the severity of intensity of a CCHFV infection. Thus, "preventing" encompasses vaccination.

As used herein, the term "treating" embraces therapeutic and preventative/prophylactic measures (including post-exposure prophylaxis) and includes post-infection therapy and amelioration of a CCHFV infection.

Each of the above-described methods can comprise the step of administering to a subject an effective amount, such as a therapeutically effective amount, of a vector or a compound of the invention.

In this regard, as used herein, an effective amount is a dosage or amount that is sufficient to achieve a desired biological outcome. As used herein, a therapeutically effective amount is an amount which is effective, upon single or multiple dose administration to a subject (such as a mammalian subject, in particular a human subject) for treating, preventing, curing, delaying, reducing the severity of, ameliorating at least one symptom of a disorder or recurring disorder, or prolonging the survival of the subject beyond that expected in the absence of such treatment.

Accordingly, the quantity of active ingredient to be administered depends on the subject to be treated, capacity of the subject's immune system to generate a protective immune response, and the degree of protection required. Precise amounts of active ingredient required to be administered may depend on the judgement of the practitioner and may be particular to each subject.

Administration to the subject can comprise administering to the subject a vector (as described above) or a composition (as described above) wherein the composition is sequentially administered multiple times (for example, wherein the composition is administered two, three or four times). Thus, in one embodiment, the subject is administered a vector (as described above) or a composition (as described above) and is then administered the same vector or composition (or a substantially similar vector or composition) again at a different time.

In one embodiment, administration to a subject comprises administering a vector (as described above) or a composition (as described above) to a subject, wherein said composition is administered substantially prior to, simultaneously with, or subsequent to, another immunogenic composition.

Prior, simultaneous and sequential administration regimes are discussed in more detail below.

In certain embodiments, the above-described methods further comprise the administration to the subject of a second vector, wherein the second vector comprises a nucleic acid sequence encoding a CCHFV glycoprotein. Preferably, the second vector is a vector of the invention as described above (such as a viral vector, for example a non-replicating poxvirus vector or an adenovirus vector as described above).

In one embodiment, the first and second vectors encode the same CCHFV glycoprotein(s). In one embodiment, the first and second vectors encode different glycoprotein(s) or different CCHFV antigens.

In one embodiment, the first and second vectors are of the same vector type. In on embodiment, the first and second vectors are of different vector types. In one embodiment, the first vector is an adenovirus vector (as described above) and the second vector is a non-replicating poxvirus vector (as described above). In one embodiment, the first vector is a non-replicating poxvirus vector (as described above) and the second vector is an adenovirus vector (as described above).

In one embodiment, the first and second vectors are administered sequentially, in any order. Thus, the first ("1") and second ("2") vectors may be administered to a subject in the order 1-2, or in the order 2-1.

As used herein, "administered sequentially" has the meaning of "sequential administration", as defined below. Thus, the first and second vectors are administered at (substantially) different times, one after the other.

In one embodiment, the first and second vectors are administered as part of a prime-boost administration protocol. Thus, the first vector may be administered to a subject as the "prime" and the second vector subsequently administered to the same subject as the "boost". Prime-boost protocols are discussed below.

In one embodiment, each of the above-described methods further comprises the step of administration to the subject of a CCHFV polypeptide antigen. In one embodiment, the CCHFV polypeptide antigen is a CCHFV glycoprotein (or antigenic fragment thereof) as described above. In one embodiment, the CCHFV polypeptide antigen is a CCHFV glycoprotein comprising an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 5 and 6.

In one embodiment, the polypeptide antigen is administered separately from the administration of a vector; preferably the polypeptide antigen and a vector are administered sequentially, in any order. Thus, in one embodiment, the vector ("V") and the polypeptide antigen ("P") may be administered in the order V-P, or in the order P-V.

In one embodiment, each of the above-described methods further comprises the step of administration to the subject of a naked DNA encoding a CCHFV glycoprotein or antigenic fragment thereof. In one embodiment, the naked DNA comprises (or consists of) a nucleic acid sequence having at least 70% (such as at least 70, 75, 80, 82, 84, 86, 88, 90, 92, 94, 95, 96, 97, 98, 99 or 100%) sequence identity to a nucleic acid sequence selected from SEQ ID NOs: 1, 2, and 3. In one embodiment, the naked DNA encodes a CCHFV glycoprotein comprising (or consisting of) an amino acid sequence having at least 70% (such as at least 70, 75, 80, 82, 84, 86, 88, 90, 92, 94, 95, 96, 97, 98, 99 or 100%) sequence identity to an amino acid sequence selected from SEQ ID NOs: 5 and 6.

In one embodiment, the naked DNA is administered separately from the administration of a vector; preferably the naked DNA and a vector are administered sequentially, in any order. Thus, in one embodiment, the vector ("V") and the naked DNA ("D") may be administered in the order V-D, or in the order D-V.

In one embodiment, a naked DNA (as described above) is administered to a subject as part of a prime-boost protocol.

Heterologous prime-boosting approaches can improve immune responses, by allowing repeated vaccinations without increasing anti-vector immunity. A CCHFV glycoprotein (GP) or an antigenic fragment thereof can be serially delivered via different vectors (as described above) or naked DNA vectors (as described above). In any heterologous prime-boost vaccination regime, GP-specific antibody response is increased, GP-specific T-cell response is increased, and/or clinical illness is reduced, as compared to use of a single vector. Suitable combinations of vectors include but are not limited to:

DNA prime, MVA boost
DNA prime, Fowlpox boost
Fowlpox prime, MVA boost
MVA prime, Fowlpox boost
DNA prime, Fowlpox boost, MVA boost
MVA prime, Adenovirus boost As used herein, the term polypeptide embraces peptides and proteins.

In certain embodiments, the above-described methods further comprise the administration to the subject of an adjuvant. Adjuvant may be administered with one, two, three, or all four of: a first vector, a second vector, a polypeptide antigen, and a naked DNA.

The immunogenic compositions, therapeutic formulations, medicaments, pharmaceutical compositions, and prophylactic formulations (e.g. vaccines) of the invention may be given in a single dose schedule (i.e. the full dose is given at substantially one time). Alternatively, the immunogenic compositions, therapeutic formulations, medicaments, pharmaceutical compositions, and prophylactic formulations (e.g. vaccines) of the invention may be given in a multiple dose schedule.

A multiple dose schedule is one in which a primary course of treatment (e.g. vaccination) may be with 1-6 separate doses, followed by other doses given at subsequent time intervals required to maintain and or reinforce the immune response, for example (for human subjects), at 1-4 months for a second dose, and if needed, a subsequent dose(s) after a further 1-4 months.

The dosage regimen will be determined, at least in part, by the need of the individual and be dependent upon the judgment of the practitioner (e.g. doctor or veterinarian).

Simultaneous administration means administration at (substantially) the same time.

Sequential administration of two or more compositions/therapeutic agents/vaccines means that the compositions/therapeutic agents/vaccines are administered at (substantially) different times, one after the other.

For example, sequential administration may encompass administration of two or more compositions/therapeutic agents/vaccines at different times, wherein the different times are separated by a number of days (for example, 1, 2, 5, 10, 15, 20, 30, 60, 90, 100, 150 or 200 days).

For example, in one embodiment, the vaccine of the present invention may be administered as part of a 'prime-boost' vaccination regime.

In one embodiment, the immunogenic compositions, therapeutic formulations, medicaments, pharmaceutical compositions, and prophylactic formulations (e.g. vaccines) of the invention can be administered to a subject such as a mammal (e.g. a human, bovine, porcine, ovine, caprine, equine, cervine, ursine, canine or feline subject) in conjunction with (simultaneously or sequentially) one or more immunoregulatory agents selected from, for example, immunoglobulins, antibiotics, interleukins (e.g. IL-2, IL-12), and/or cytokines (e.g. IFNγ).

The immunogenic compositions, therapeutic formulations, medicaments, pharmaceutical compositions, and prophylactic formulations (e.g. vaccines) may contain 5% to 95% of active ingredient, such as at least 10% or 25% of active ingredient, or at least 40% of active ingredient or at least 50, 55, 60, 70 or 75% active ingredient.

The immunogenic compositions, therapeutic formulations, medicaments, pharmaceutical compositions, and prophylactic formulations (e.g. vaccines) are administered in a manner compatible with the dosage formulation, and in such amount as will be prophylactically and/or therapeutically effective.

Administration of immunogenic compositions, therapeutic formulations, medicaments, pharmaceutical compositions, and prophylactic formulations (e.g. vaccines) is generally by conventional routes e.g. intravenous, subcutaneous, intraperitoneal, or mucosal routes. The administration may be by parenteral administration; for example, a subcutaneous or intramuscular injection.

Accordingly, immunogenic compositions, therapeutic formulations, medicaments, pharmaceutical compositions, and prophylactic formulations (e.g. vaccines) of the invention may be prepared as injectables, either as liquid solutions or suspensions. Solid forms suitable for solution in, or suspension in, liquid prior to injection may alternatively be prepared. The preparation may also be emulsified, or the peptide encapsulated in liposomes or microcapsules.

The active ingredients are often mixed with excipients which are pharmaceutically acceptable and compatible with the active ingredient. Suitable excipients are, for example, water, saline, dextrose, glycerol, ethanol, or the like and combinations thereof. In addition, if desired, the immunogenic compositions, therapeutic formulations, medicaments, pharmaceutical compositions, and prophylactic formulations (e.g. vaccines) may contain minor amounts of auxiliary substances such as wetting or emulsifying agents, and/or pH buffering agents.

Generally, the carrier is a pharmaceutically-acceptable carrier. Non-limiting examples of pharmaceutically acceptable carriers include water, saline, and phosphate-buffered saline. In some embodiments, however, the composition is in lyophilized form, in which case it may include a stabilizer, such as bovine serum albumin (BSA). In some embodiments, it may be desirable to formulate the composition with a preservative, such as thiomersal or sodium azide, to facilitate long term storage.

Examples of buffering agents include, but are not limited to, sodium succinate (pH 6.5), and phosphate buffered saline (PBS; pH 6.5 and 7.5).

Additional formulations which are suitable for other modes of administration include suppositories and, in some cases, oral formulations or formulations suitable for distribution as aerosols. For suppositories, traditional binders and carriers may include, for example, polyalkylene glycols or triglycerides; such suppositories may be formed from mixtures containing the active ingredient in the range of 0.5% to 10%, preferably 1%-2%.

Oral formulations include such normally employed excipients as, for example, pharmaceutical grades of mannitol, lactose, starch, magnesium stearate, sodium saccharine, cellulose, magnesium carbonate, and the like. These compositions take the form of solutions, suspensions, tablets, pills, capsules, sustained release formulations or powders.

It may be desired to direct the compositions of the present invention (as described above) to the respiratory system of a subject. Efficient transmission of a therapeutic/prophylactic composition or medicament to the site of infection in the lungs may be achieved by oral or intra-nasal administration.

Formulations for intranasal administration may be in the form of nasal droplets or a nasal spray. An intranasal formulation may comprise droplets having approximate diameters in the range of 100-5000 μm, such as 500-4000 μm, 1000-3000 μm or 100-1000 μm. Alternatively, in terms of volume, the droplets may be in the range of about 0.001-100 μl, such as 0.1-50 μl or 1.0-25 μl, or such as 0.001-1 μl.

Alternatively, the therapeutic/prophylactic formulation or medicament may be an aerosol formulation. The aerosol formulation may take the form of a powder, suspension or solution. The size of aerosol particles is relevant to the delivery capability of an aerosol. Smaller particles may travel further down the respiratory airway towards the alveoli than would larger particles. In one embodiment, the aerosol particles have a diameter distribution to facilitate delivery along the entire length of the bronchi, bronchioles, and alveoli. Alternatively, the particle size distribution may be selected to target a particular section of the respiratory airway, for example the alveoli. In the case of aerosol delivery of the medicament, the particles may have diameters in the approximate range of 0.1-50 μm, preferably 1-25 μm, more preferably 1-5 μm.

Aerosol particles may be for delivery using a nebulizer (e.g. via the mouth) or nasal spray. An aerosol formulation may optionally contain a propellant and/or surfactant.

In one embodiment, the immunogenic compositions, therapeutic formulations, medicaments, pharmaceutical compositions, and prophylactic formulations (e.g. vaccines) of the invention comprise a pharmaceutically acceptable carrier, and optionally one or more of a salt, excipient, diluent and/or adjuvant.

In one embodiment, the immunogenic compositions, therapeutic formulations, medicaments, pharmaceutical compositions, and prophylactic formulations (e.g. vaccines) of the invention may comprise one or more immunoregulatory agents selected from, for example, immunoglobulins, antibiotics, interleukins (e.g. IL-2, IL-12), and/or cytokines (e.g. IFNγ).

The present invention encompasses polypeptides that are substantially homologous to polypeptides based on any one of the polypeptide antigens identified in this application (including fragments thereof). The terms "sequence identity" and "sequence homology" are considered synonymous in this specification.

By way of example, a polypeptide of interest may comprise an amino acid sequence having at least 70, 75, 80, 82, 84, 86, 88, 90, 92, 94, 96, 98, 99 or 100% amino acid sequence identity with the amino acid sequence of a reference polypeptide.

There are many established algorithms available to align two amino acid sequences.

Typically, one sequence acts as a reference sequence, to which test sequences may be compared. The sequence comparison algorithm calculates the percentage sequence identity for the test sequence(s) relative to the reference sequence, based on the designated program parameters. Alignment of amino acid sequences for comparison may be conducted, for example, by computer implemented algorithms (e.g. GAP, BESTFIT, FASTA or TFASTA), or BLAST and BLAST 2.0 algorithms.

The BLOSUM62 table shown below is an amino acid substitution matrix derived from about 2,000 local multiple alignments of protein sequence segments, representing highly conserved regions of more than 500 groups of related proteins (Henikoff & Henikoff, Proc. Natl. Acad. Sci. USA 89:10915-10919, 1992; incorporated herein by reference). Amino acids are indicated by the standard one-letter codes. The percent identity is calculated as:

$$\frac{\text{Total number of identical matches}}{\left[\begin{array}{c}\text{length of the longer sequence plus} \\ \text{the number of gaps Introduced into the} \\ \text{longer sequence in order to align the two sequences}\end{array}\right]} \times 100$$

In a homology comparison, the identity may exist over a region of the sequences that is at least 10 amino acid residues in length (e.g. at least 15, 20, 30, 40, 50, 75, 100, 150, 200, 250, 300, 350, 400, 450, 500, 550, 600, 650 or 685 amino acid residues in length—e.g. up to the entire length of the reference sequence.

Substantially homologous polypeptides have one or more amino acid substitutions, deletions, or additions. In many embodiments, those changes are of a minor nature, for example, involving only conservative amino acid substitutions. Conservative substitutions are those made by replacing one amino acid with another amino acid within the following groups: Basic: arginine, lysine, histidine; Acidic: glutamic acid, aspartic acid; Polar: glutamine, asparagine; Hydrophobic: leucine, isoleucine, valine; Aromatic: phenylalanine, tryptophan, tyrosine; Small: glycine, alanine, serine, threonine, methionine. Substantially homologous polypeptides also encompass those comprising other substitutions that do not significantly affect the folding or activity of the polypeptide; small deletions, typically of 1 to about 30 amino acids (such as 1-10, or 1-5 amino acids); and small amino- or carboxyl-terminal extensions, such as an amino-terminal methionine residue, a small linker peptide of up to about 20-25 residues, or an affinity tag.

As used herein, the terms "nucleic acid sequence" and "polynucleotide" are used interchangeably and do not imply any length restriction. As used herein, the terms "nucleic acid" and "nucleotide" are used interchangeably. The terms "nucleic acid sequence" and "polynucleotide" embrace DNA (including cDNA) and RNA sequences.

BLOSUM62 table

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 |   |   |   |   |   |   |   |   |   |   |   |   |   |   |   |   |   |   |   |
| R | -1 | 5 |   |   |   |   |   |   |   |   |   |   |   |   |   |   |   |   |   |   |
| N | -2 | 0 | 6 |   |   |   |   |   |   |   |   |   |   |   |   |   |   |   |   |   |
| D | -2 | -2 | 1 | 6 |   |   |   |   |   |   |   |   |   |   |   |   |   |   |   |   |
| C | 0 | -3 | -3 | -3 | 9 |   |   |   |   |   |   |   |   |   |   |   |   |   |   |   |
| Q | -1 | 1 | 0 | 0 | -3 | 5 |   |   |   |   |   |   |   |   |   |   |   |   |   |   |
| E | -1 | 0 | 0 | 2 | -4 | 2 | 5 |   |   |   |   |   |   |   |   |   |   |   |   |   |
| G | 0 | -2 | 0 | -1 | -3 | -2 | -2 | 6 |   |   |   |   |   |   |   |   |   |   |   |   |
| H | -2 | 0 | 1 | -1 | -3 | 0 | 0 | -2 | 8 |   |   |   |   |   |   |   |   |   |   |   |
| I | -1 | -3 | -3 | -3 | -1 | -3 | -3 | -4 | -3 | 4 |   |   |   |   |   |   |   |   |   |   |
| L | -1 | -2 | -3 | -4 | -1 | -2 | -3 | -4 | -3 | 2 | 4 |   |   |   |   |   |   |   |   |   |
| K | -1 | 2 | 0 | -1 | -3 | 1 | 1 | -2 | -1 | -3 | -2 | 5 |   |   |   |   |   |   |   |   |
| M | -1 | -1 | -2 | -3 | -1 | 0 | -2 | -3 | -2 | 1 | 2 | -1 | 5 |   |   |   |   |   |   |   |
| F | -2 | -3 | -3 | -3 | -2 | -3 | -3 | -3 | -1 | 0 | 0 | -3 | 0 | 6 |   |   |   |   |   |   |
| P | -1 | -2 | -2 | -1 | -3 | -1 | -1 | -2 | -2 | -3 | -3 | -1 | -2 | -4 | 7 |   |   |   |   |   |
| S | 1 | -1 | 1 | 0 | -1 | 0 | 0 | 0 | -1 | -2 | -2 | 0 | -1 | -2 | -1 | 4 |   |   |   |   |
| T | 0 | -1 | 0 | -1 | -1 | -1 | -1 | -2 | -2 | -1 | -1 | -1 | -1 | -2 | -1 | 1 | 5 |   |   |   |
| W | -3 | -3 | -4 | -4 | -2 | -2 | -3 | -2 | -2 | -3 | -2 | -3 | -1 | 1 | -4 | -3 | -2 | 11 |   |   |
| Y | -2 | -2 | -2 | -3 | -2 | -1 | -2 | -3 | 2 | -1 | -1 | -2 | -1 | 3 | -3 | -2 | -2 | 2 | 7 |   |
| V | 0 | -3 | -3 | -3 | -1 | -2 | -2 | -3 | -3 | 3 | 1 | -2 | 1 | -1 | -2 | -2 | 0 | -3 | -1 | 4 |

The polynucleotide sequences of the present invention include nucleic acid sequences that have been removed from their naturally occurring environment, recombinant or cloned DNA isolates, and chemically synthesized analogues or analogues biologically synthesized by heterologous systems.

The polynucleotides of the present invention may be prepared by any means known in the art. For example, large amounts of the polynucleotides may be produced by replication in a suitable host cell. The natural or synthetic DNA fragments coding for a desired fragment will be incorporated into recombinant nucleic acid constructs, typically DNA constructs, capable of introduction into and replication in a prokaryotic or eukaryotic cell. Usually the DNA constructs will be suitable for autonomous replication in a unicellular host, such as yeast or bacteria, but may also be intended for introduction to and integration within the genome of a cultured insect, mammalian, plant or other eukaryotic cell lines.

The polynucleotides of the present invention may also be produced by chemical synthesis, e.g. by the phosphoramidite method or the tri-ester method, and may be performed on commercial automated oligonucleotide synthesizers. A double-stranded fragment may be obtained from the single stranded product of chemical synthesis either by synthesizing the complementary strand and annealing the strand together under appropriate conditions or by adding the complementary strand using DNA polymerase with an appropriate primer sequence.

When applied to a nucleic acid sequence, the term "isolated" in the context of the present invention denotes that the polynucleotide sequence has been removed from its natural genetic milieu and is thus free of other extraneous or unwanted coding sequences (but may include naturally occurring 5' and 3' untranslated regions such as promoters and terminators), and is in a form suitable for use within genetically engineered protein production systems. Such isolated molecules are those that are separated from their natural environment.

In view of the degeneracy of the genetic code, considerable sequence variation is possible among the polynucleotides of the present invention. Degenerate codons encompassing all possible codons for a given amino acid are set forth below:

| Amino Acid | Codons | Degenerate Codon |
|---|---|---|
| Cys | TGC TGT | TGY |
| Ser | AGC AGT TCA TCC TCG TCT | WSN |
| Thr | ACA ACC ACG ACT | ACN |
| Pro | CCA CCC CCG CCT | CCN |
| Ala | GCA GCC GCG GCT | GCN |
| Gly | GGA GGC GGG GGT | GGN |
| Asn | AAC AAT | AAY |
| Asp | GAC GAT | GAY |
| Glu | GAA GAG | GAR |
| Gln | CAA CAG | CAR |
| His | CAC CAT | CAY |
| Arg | AGA AGG CGA CGC CGG CGT | MGN |
| Lys | AAA AAG | AAR |
| Met | ATG | ATG |
| Ile | ATA ATC ATT | ATH |
| Leu | CTA CTC CTG CTT TTA TTG | YTN |
| Val | GTA GTC GTG GTT | GTN |
| Phe | TTC TTT | TTY |
| Tyr | TAC TAT | TAY |
| Trp | TGG | TGG |
| Ter | TAA TAG TGA | TRR |
| Asn/Asp |  | RAY |
| Glu/Gln |  | SAR |
| Any |  | NNN |

One of ordinary skill in the art will appreciate that flexibility exists when determining a degenerate codon, representative of all possible codons encoding each amino acid. For example, some polynucleotides encompassed by the degenerate sequence may encode variant amino acid sequences, but one of ordinary skill in the art can easily identify such variant sequences by reference to the amino acid sequences of the present invention.

A "variant" nucleic acid sequence has substantial homology or substantial similarity to a reference nucleic acid sequence (or a fragment thereof). A nucleic acid sequence or fragment thereof is "substantially homologous" (or "substantially identical") to a reference sequence if, when optimally aligned (with appropriate nucleotide insertions or deletions) with the other nucleic acid (or its complementary strand), there is nucleotide sequence identity in at least about 70%, 75%, 80%, 82, 84, 86, 88, 90, 92, 94, 96, 98 or 99% of the nucleotide bases. Methods for homology determination of nucleic acid sequences are known in the art.

Alternatively, a "variant" nucleic acid sequence is substantially homologous with (or substantially identical to) a reference sequence (or a fragment thereof) if the "variant" and the reference sequence they are capable of hybridizing under stringent (e.g. highly stringent) hybridization conditions. Nucleic acid sequence hybridization will be affected by such conditions as salt concentration (e.g. NaCl), temperature, or organic solvents, in addition to the base composition, length of the complementary strands, and the number of nucleotide base mismatches between the hybridizing nucleic acids, as will be readily appreciated by those skilled in the art. Stringent temperature conditions are preferably employed, and generally include temperatures in excess of 30° C., typically in excess of 37° C. and preferably in excess of 45° C. Stringent salt conditions will ordinarily be less than 1000 mM, typically less than 500 mM, and preferably less than 200 mM. The pH is typically between 7.0 and 8.3. The combination of parameters is much more important than any single parameter.

Methods of determining nucleic acid percentage sequence identity are known in the art. By way of example, when assessing nucleic acid sequence identity, a sequence having a defined number of contiguous nucleotides may be aligned with a nucleic acid sequence (having the same number of contiguous nucleotides) from the corresponding portion of a nucleic acid sequence of the present invention. Tools known in the art for determining nucleic acid percentage sequence identity include Nucleotide BLAST.

One of ordinary skill in the art appreciates that different species exhibit "preferential codon usage". As used herein, the term "preferential codon usage" refers to codons that are most frequently used in cells of a certain species, thus favouring one or a few representatives of the possible codons encoding each amino acid. For example, the amino acid threonine (Thr) may be encoded by ACA, ACC, ACG, or ACT, but in mammalian host cells ACC is the most commonly used codon; in other species, different Thr codons may be preferential. Preferential codons for a particular host cell species can be introduced into the polynucleotides of the present invention by a variety of methods known in the art. Introduction of preferential codon sequences into recombinant DNA can, for example, enhance production of the protein by making protein translation more efficient within a particular cell type or species.

Thus, in one embodiment of the invention, the nucleic acid sequence is codon optimized for expression in a host cell.

A "fragment" of a polynucleotide of interest comprises a series of consecutive nucleotides from the sequence of said full-length polynucleotide. By way of example, a "fragment" of a polynucleotide of interest may comprise (or consist of) at least 30 consecutive nucleotides from the sequence of said polynucleotide (e.g. at least 35, 50, 75, 100, 150, 200, 250, 300, 350, 400, 450, 500, 550, 600, 650, 700, 750, 800 850, 900, 950 or 1000 consecutive nucleic acid residues of said polynucleotide). A fragment may include at least one antigenic determinant and/or may encode at least one antigenic epitope of the corresponding polypeptide of interest.

BRIEF DESCRIPTION OF THE DRAWINGS

FIG. 1A. Cassette used in plasmid pLW44. Green Fluorescent Protein (GFP) is driven by poxvirus promoter p11. A multi-cloning site is downstream of poxvirus promoter mH5. MVA flanks L and R allow recombination with MVA genome.

FIG. 1B. Cassette used in plasmid pLW44 following modification (renamed as plasmid pDEST44-TPA-V5).

FIG. 1C. Recombination between pDEST44-TPA-V5 and pENTR-GP results in pTP-GP, containing the depicted cassette (SEQ ID NO: 7).

FIG. 2. MVA-GP immunogenicity in Balb/c mice. IFN-γ ELISpot on splenocytes 8 or 14 days post-boost showed T-cell immunogenicity of GP FIG. 3. Experimental protocol for Example 2.

Figure 5B:
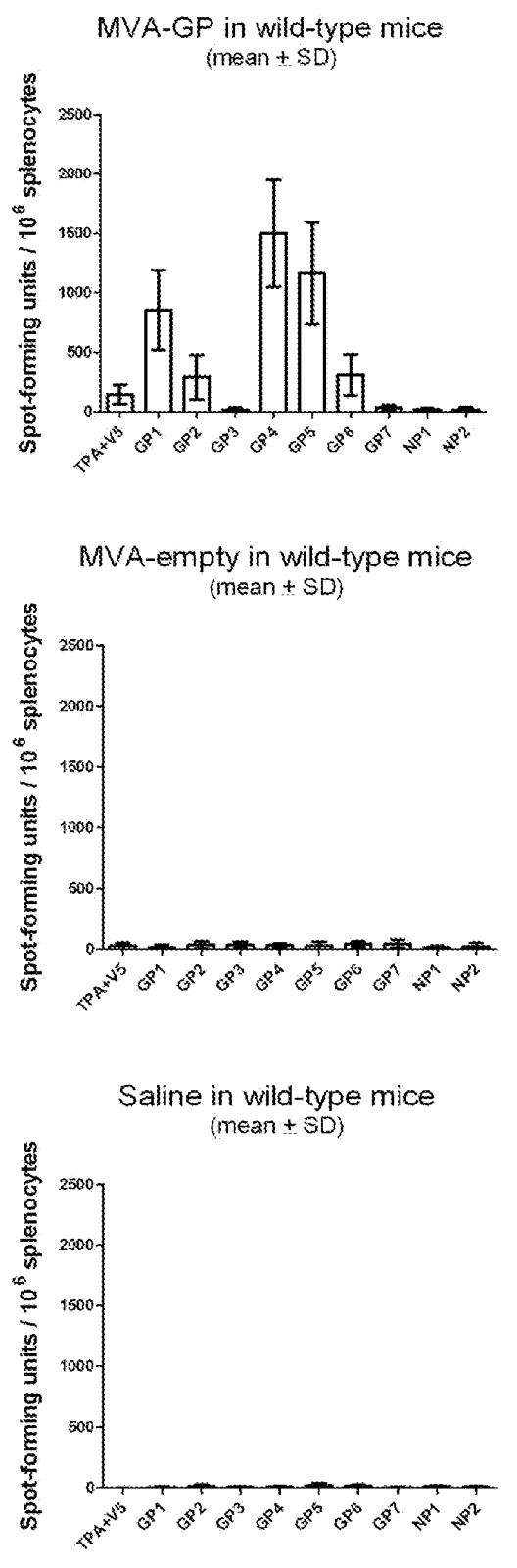

FIG. 5A-B. IFN-γ ELISPOT results subdivided into peptide pools (1 for TPA/V5, 7 for GP and 2 for NP).

Figure 1A:
FIG. 1A-C. Example MVA Vector Construction.

Western Blot Analysis of Glycoproteins Expressed by MVA-GP and CCHFv.

(A) Western blotting of MVA-GP with anti-V5 antibody indicates a protein of approximately 75 kDa, confirming recombinant protein expression, and consistent with cleavage of the predicted 76.6 kDa $G_C$~V5 fusion protein.

(B) Western blotting of MVA-1974 (lane 1), MVA-GP (lane 2), CCHFv-infected SW13 cells (lane 3) and uninfected SW13 cells (lane 4) with polyclonal serum from rabbits vaccinated with peptides derived from the CCHF viral glycoprotein. Major products expressed by MVA-GP correspond with those expressed by CCHFv, indicating the recombinant protein undergoes similar post-translational cleavages as the native protein.

FIG. 16.

Antibody Responses from Vaccinated A129 and 129Sv/Ev Mice.

Sera from vaccinated mice were tested for reactivity with CCHFv-infected (lane 3) or uninfected (lane 2) SW13 cells by Western blotting. Lane 1 shows a molecular weight marker. Blots show proteins reactive with serum from representative individual animals 7 days after booster vaccination (A-E) or representative pooled serum 14 days after booster vaccination (F). Secondary antibody used was specific for mouse IgG (A-C, F), or mouse IgG, IgA and IgM (D-E). Arrows indicate CCHFv-specific proteins, indicating specific antibody responses in both mouse strains.

(A) 129Sv/Ev mouse vaccinated with MVA-GP. (B, E) A129 mouse vaccinated with MVA-GP. (C) A129 mouse vaccinated with MVA 1974. (D) A129 mouse vaccinated with MVA-GP. (F) Pooled serum from A129 mice vaccinated with MVA-GP.

FIG. 17.

Tissue Histology of A129 Mice, 4 Days after Challenge with CCHFv.

A129 mice were challenged with double the minimum lethal dose of CCHFv, 14 days after booster vaccination with MVA 1974 (A-B) or MVA-GP (C-D). Four days after challenge, sections of spleen (A, C) and liver (B, D) were fixed, HE stained, and examined for pathology. More severe pathology was found in mice that received MVA 1974, compared to those that received MVA-GP. (A) Marked lymphocyte loss with prominent apoptotic bodies, and infiltration by macrophages. (B) Marked, multifocally extensive hepatocyte necrosis (arrows). (C) A single infiltration of macrophages in the white pulp (asterisk) (scored minimal). (D) Scattered, multifocal areas of hepatocellular necrosis with a mixed inflammatory cell infiltrate (arrows) (scored moderate).

FIG. 18.

Immunohistochemistry of Tissues from A129 Mice, 4 Days after Challenge with CCHFv.

A129 mice were challenged with double the minimum lethal dose of CCHFv, 14 days after booster vaccination with MVA 1974 (A-C) or MVA-GP (D-E). Four days after challenge, sections of spleen (A, D) and liver (B-C, E) were fixed, immunohistochemically stained with CCHFv-specific antibody, and examined microscopically. Tissues in panels A, B, D and E were from the same individuals as shown in FIGS. 5A, 5B, 5C and 5D, respectively. A diffuse staining pattern of viral proteins was found in tissues from animals that received the MVA 1974 negative control. However, in MVA-GP vaccinated animals, the only staining found was of a minimal degree, in liver from one individual.

(A) A few, scattered cells with cytoplasmic staining within the parenchyma. (B) Frequent, diffuse, positively stained hepatocytes. (C) Scattered, small, elongated cells consistent with Kupffer cells, with cytoplasmic staining. (D) Normal parenchyma. (E) A few, positively stained cells within an inflammatory cell focus.

FIG. 19.

Viral Load Analysis of CCHFv RNA Copy Number by RT-PCR.

A129 mice (n=9) were challenged with double the minimum lethal dose of CCHFv, 14 days after booster vaccination with MVA-GP, MVA 1974, or saline. Four days post-challenge (day 32), 3 randomly selected animals from each group were killed humanely and analysed by RT-PCR for copy number of CCHFv S segment in various tissues. Fourteen days post-challenge (day 42), all surviving animals were killed humanely and also analysed. Each bar represents the mean±standard deviation in an individual animal.

In all tissues tested, viral load was significantly lower in MVA-GP vaccinated mice than in control groups. Within the MVA-GP group, there was no significant difference in viral load between 4 days and 14 days post-challenge. (A) Blood. (B) Spleen. (C) Liver.

FIG. 20.

Normalised Viral Load Analysis of CCHFv RNA by RT-PCR.

A129 mice (n=9) were challenged with double the minimum lethal dose of CCHFv, 14 days after booster vaccination with MVA-GP, MVA 1974, or saline. Four days post-challenge (day 32), 3 randomly selected animals from each group were killed humanely and analysed by RT-PCR for CCHFv gene expression, normalised to mouse HPRT gene expression. Fourteen days post-challenge (day 42), all surviving animals were killed humanely and also analysed. Each point represents the mean value of triplicate measurements in an individual animal. Lines show mean±standard deviation.

In all tissues tested, viral load was significantly lower in MVA-GP vaccinated mice than in control groups. Within the MVA-GP group, there was no significant difference in viral load between 4 days and 14 days post-challenge. (A) Blood. (B) Spleen. (C) Liver.

KEY TO SEQ ID NOS

SEQ ID NO: 1 Full length CCHFV M segment open reading frame nucleic acid sequence (from Accession Number U39455).

SEQ ID NO: 2 CCHFV $G_N$ glycoprotein nucleic acid sequence.

SEQ ID NO: 3 CCHFV $G_C$ glycoprotein nucleic acid sequence.

SEQ ID NO: 4 Amino acid sequence of protein encoded by CCHFV M segment.

SEQ ID NO: 5 CCHFV $G_N$ glycoprotein amino acid sequence.

SEQ ID NO: 6 CCHFV $G_C$ glycoprotein amino acid sequence.

Figure 1B:
Figure 1C:

SEQ ID NO: 7 MVA-GP nucleic acid sequence (representing the section shown in FIG. 1C).

Sequences

SEQ ID NO: 1 atgcatatatcattaatgtatgcaatcctttgcctacagctgtgtggtct gggagagactcatggatcacacaatgaaactagacacaataaaacagaca ccatgacaacacacggtgataacccgagctctgaaccgccagtgagcacg gccttgtctattacacttgaccctccactgtcacacccacaacaccagc cagtggattagaaggctcaggggaagtctacacatcccctccgatcacca ccgggagcttgccctgtcggagacaacaccagaactccctgttacaacc ggcacagacaccttaagcgcaggtgatgtcgatcccagcacgcagacagc cggaggcacctccgcaccaacagtccgcacaagtctacccaacagcccta gcacaccatctacaccacaagacacacaccatcctgtgagaaatctactt tcagtcacgagtcctgggccagatgaaacatcaaccctcgggaacagg caaagagagctcagcaaccagtagccctcatccagtctccaacagaccac caacccctcctgcaacagcccagggacccactgaaaatgacagtcacaac gccactgaacaccctgagtccctgacacagtcagcaaccccaggcctaat gacctctccaacacagatagtccacccacaaagtgccaccccccataaccg ttcaagacacacatcccagtccaacgaacaggtctaaaagaaaccttaag atggaaataatcttgactttatctcagggtttaaaaaagtactatgggaa aatattaaggcttctgcaactcaccttagaggaggacactgaaggtctac tggaatggtgtaagagaaatcttggtcttgattgtgatgacactttcttt caaaagagaattgaagaattctttataactggtgagggccattttaatga agttttacaatttagaacgccaggcacgttgagcaccacagagtcaacac ctgctgggctgccaacagctgaaccttttaagtcctacttcgccaaaggc ttcctctcgatagattcaggttactactcagccaaatgttactcaggaac atccaattcagggcttcaattgattaacattacccgacattcaactagaa tagttgacacacctgggcctaagatcactaacctaaagaccatcaactgc ataaacttgaaggcatcgatcttcaaagaacatagagaggttgaaatcaa tgtgcttctcccccaagttgcagttaatctctcaaactgtcacgttgtaa tcaaatcacatgtctgtgactactctttagacattgacggtgcggtgagg cttcctcacatttaccatgaaggagttttcatcccaggaacttacaaaat agtgatagataaaaaaaataagttgaatgacagatgcaccttatttaccg actgtgtgataaaaggaagggaggttcgtaaaggacagtcagtttttgagg cagtacaagacggaaatcaggattggcaaggcatcaaccggctttagaag attgctttcagaagaacccagtgatgactgtgtatcaagaactcaactat taaggacagagactgcagagatccacggcgacaactatggtggcccgggt gacaaaataaccatctgcaatggctcaactattgtagaccaaagactggg cagtgaactaggatgctacaccatcaatagagtgaggtcattcaagctat gcgaaaacagtgccacagggaagaattgtgaaatagacagtgtcccagtt aaatgcaggcagggttattgcctaagaatcactcaggaagggaggggcca cgtaaaattatctaggggctcagaggttgtcttagatgcatgcgatacaa gctgtgaaataatgatacctaagggcactggtgacatcctagttgactgt -continued tcaggtgggcagcaacattttctaaaggacaatttgatagatctaggatg ccccaaaattccattattgggcaaaatggctatttacatttgcagaatgt caaaccaccccaaaacaaccatggctttcctcttctggttcagctttggc tatgtaataacctgcatactttgcaaggctatttttttacttgttaataat tgttggaacactagggagaaggctcaagcagtatagagagttgaaacctc agacttgcaccatatgtgagacaactcctgtaaatgcaatagatgctgag atgcatgacctcaattgcagttacaacatttgtccctactgtgcatctag actaacctcagatgggcttgctaggcatgtgatacaatgccctaagcgga aggagaaagtggaagaaactgaactgtacttgaacttagaaagaattcct tgggttgtaagaaagctgttgcaggtgtcagagtcaactggtgtggcatt gaaaagaagcagttggctgattgtgctgcttgtgctattcactgtttcat tatcaccagttcaatcagcacccattggtcaagggaagacaattgaggca taccgggccagggaagggtacacaagtatatgcctctttgtactaggaag tatcctatttatagtttcttgcctaatgaaagggctggttgacagtgttg gcaactccttcttccctggactgtccatttgcaaaacgtgctccataagc agcattaatggctttgaaattgagtcccataagtgctattgcagcttatt ctgttgcccctattgtaggcactgctctaccgataaagaaattcataagc tgcacttgagcatctgcaaaaaaggaaaacaggaagtaatgtcatgttg gctgtctgcaagctcatgtgtttcagggccaccatggaagtaagtaacag agccctgtttatccgtagcatcatcaacaccacttttgttttgtgcatac tgatactagcagtttgtgttgttagcacctcagcagtggagatggaaaac ctaccagcagggacctgggaaagagaagaagacctaacaaatttctgtca tcaggaatgccaggttacagagactgaatgcctctgcccttatgaagctc tagtactcagaaagcctttattcctagatagtacagctaaaggcatgaaa aatctgctaaattcaacaagtttagaaacgagtttatcaattgaggcacc atggggagcaataaatgttcagtcaacctacaaaccaactgtgtcaactg caaacatagcactcagtggagctcagtgaacacagaggcaataagatc ttggtttcaggcagatcagaatcaattatgaagctggaagaaaggacagg aatcagctgggatctcggtgtagaagatgcctctgaatctaaactgctta cagtatctgtcatggacttgtctcagatgtactctcctgtcttcgagtac ttatcaggggacagacaggtggaagagtggcccaaagcaacttgcacagg tgactgcccagaaagatgtggctgcacatcatcaacctgtttgcacaaag aatgcctcactcaagaaattggagatgcaatcccacttggtgctgggt gtagggactggctgcacctgttgtggattagatgtgaaagacctttttac agattatatgtttgtcaagtggaaagttgaatacatcaagacagaggca tagtgtgtgtagaacttactagtcaggaaaggcagtgtagcttgattgaa gcgggcacaaggttcaatttaggtcctgtgaccatcacactgtcagaacc aagaaacatccaacaaaaactccctcctgaaataatcacactgcatccta ggatcgaagaaggttttttttgacctgatgcatgtgcaaaaggtgttatcg gcaagcacagtgtgtaagttgcagagttgcacacatggtgtgccaggaga cctacaggtctaccacatcggaaatttattaaaaggggataaggtaaatg gacatctaattcataaaattgagccacacttcaacacctcctggatgtcc tgggatggttgtgacctagactactactgcaacatgggagattggccttc ttgcacatacacagggtcacccaacacaatcatgcttcatttgtaaact tactcaacattgaaactgattacacaaagaacttccactttcactctaaa agggtcactgcacacggagatacaccacaactagatcttaaggcaagacc aacctatggtgcaggcgagatcactgttctggtagaagttgctgacatgg agttacatacaaagaagattgaaatatcaggcttaaaatttgcaagctta gcttgcacaggttgttatgcttgtagctctagcatctcatgcaaagttag aattcatgtggatgaaccagatgaacttacagtacatgttaaaagtgatg atccagatgtggttgcagctagctcaagtctcatggcaaggaagcttgaa tttggaacagacagtacatttaaagctttctcggccatgcctaaaacttc tctatgtttctacattgttgaaagagaacactgtaagagctgcagtgaag aagacacaaaaaaatgtgttaacacaaaacttgagcaaccacaaagcatt ttgatcgaacacaaggaactataatcggaaagcaaaacagcacttgcac ggctaaggcaagttgctggttagagtcagtcaagagtttttttatggcc taaagaacatgcttagtggcatttttggcaatgtctttatgggcattttc ttgttccttgccccctcatcctgttaatactattcttatgtttgggtg gaggatcctattctgctttaaatgttgtagaagaaccagaggcctgttca agtatagacacctcaaagacgatgaagaaactggttatagaaggattatt gaaaaactaaacaataaaaaaggaaaaaacaaactgcttgatggtgaaag acttgctgatggaagaattgccgaactgttctctacaaaaacacacattg gctag SEQ ID NO: 2
agaagattgctttcagaagaacccagtgatgactgtgtatcaagaactca actattaaggacagagactgcagagatccacggcgacaactatggtggcc cgggtgacaaaataaccatctgcaatggctcaactattgtagaccaaaga ctgggcagtgaactaggatgctacaccatcaatagagtgaggtcattcaa gctatgcgaaaacagtgccacagggaagaattgtgaaatagacagtgtcc cagttaaatgcaggcagggttattgcctaagaatcactcaggaagggagg ggccacgtaaaattatctaggggctcagaggttgtcttagatgcatgcga tacaagctgtgaaataatgatacctaagggcactggtgacatcctagttg actgttcaggtgggcagcaacattttctaaaggacaatttgatagatcta ggatgccccaaaattccattattgggcaaaatggctatttacatttgcag aatgtcaaaccaccccaaaacaaccatggctttcctcttctggttcagct ttggctatgtaataacctgcatactttgcaaggctatttttttacttgtta ataattgttggaacactagggagaaggctcaagcagtatagagagttgaa acctcagacttgcaccatatgtgagacaactcctgtaaatgcaatagatg ctgagatgcatgacctcaattgcagttacaacatttgtccctactgtgca tctagactaacctcagatgggcttgctaggcatgtgatacaatgccctaa

```
gcggaaggagaaagtggaagaaactgaactgtacttgaacttagaagaa
ttccttgggttgtaagaaagctgttg
                                            SEQ ID NO: 3
agaaagcctttattcctagatagtacagctaaaggcatgaaaaatctgct
aaattcaacaagtttagaaacgagtttatcaattgaggcaccatggggag
caataaatgttcagtcaacctacaaaccaactgtgtcaactgcaaacata
gcactcagttggagctcagtggaacacagaggcaataagatcttggtttc
aggcagatcagaatcaattatgaagctggaagaaaggacaggaatcagct
gggatctcggtgtagaagatgcctctgaatctaaactgcttacagtatct
gtcatggacttgtctcagatgtactctcctgtcttcgagtacttatcagg
ggacagacaggtggaagagtggcccaaagcaacttgcacaggtgactgcc
cagaaagatgtggctgcacatcatcaacctgtttgcacaaagaatggcct
cactcaagaaattggagatgcaatcccacttggtgctggggtgtaggac
tggctgcacctgttgtggattagatgtgaaagacctttttacagattata
tgtttgtcaagtggaaagttgaatacatcaagacagaggccatagtgtgt
gtagaacttactagtcaggaaaggcagtgtagcttgattgaagcgggcac
aaggttcaatttaggtcctgtgaccatcacactgtcagaaccaagaaaca
tccaacaaaaactccctcctgaaataatcacactgcatcctaggatcgaa
gaaggttttttttgacctgatgcatgtgcaaaaggtgttatcggcaagcac
agtgtgtaagttgcagagttgcacacatggtgtgccaggagacctacagg
tctaccacatcggaaatttattaaaaggggataaggtaaatggacatcta
attcataaaattgagccacacttcaacacctcctggatgtcctgggatgg
ttgtgacctagactactactgcaacatgggagattggccttcttgcacat
acacaggggtcacccaacacaatcatgcttcatttgtaaacttactcaac
attgaaactgattacacaaagaacttccactttcactctaaaagggtcac
tgcacacggagatacaccacaactagatcttaaggcaagaccaacctatg
gtgcaggcgagatcactgttctggtagaagttgctgacatggagttacat
acaaagaagattgaaatatcaggcttaaaatttgcaagcttagcttgcac
aggttgttatgcttgtagctctagcatctcatgcaaagttagaattcatg
tggatgaaccagatgaacttacagtacatgttaaaagtgatgatccagat
gtggttgcagctagctcaagtctcatggcaaggaagcttgaatttggaac
agacagtacatttaaagctttctcggccatgcctaaaacttctctatgtt
tctacattgttgaaagagaacactgtaagagctgcagtgaagaagacaca
aaaaaatgtgttaacacaaaacttgagcaaccacaaagcatttttgatcga
acacaagggaactataatcggaaagcaaaacagcacttgcacggctaagg
caagttgctggtagagtcagtcaagagttttttttatggcctaaagaac
atgcttagtggcattttggcaatgtctttatgggcattttcttgttcct
tgccccctttcatcctgttaatactattctttatgtttgggtggaggatcc
tattctgctttaaatgttgtagaagaaccagaggcctgttcaagtataga
cacctcaaagacgatgaagaaactggttatagaaggattattgaaaaact
```
```
aaacaataaaaaaggaaaaaacaaactgcttgatggtgaaagacttgctg
atggaagaattgccgaactgttctctacaaaaacacacattggctag
                                            SEQ ID NO: 4
MHISLMYAILCLQLCGLGETHGSHNETRHNKTDTMTTHGDNPSSEPPVST
ALSITLDPSTVTPTTPASGLEGSGEVYTSPPITTGSLPLSETTPELPVTT
GTDTLSAGDVDPSTQTAGGTSAPTVRTSLPNSPSTPSTPQDTHHPVRNLL
SVTSPGPDETSTPSGTGKESSATSSPHPVSNRPPTPPATAQGPTENDSHN
ATEHPESLTQSATPGLMTSPTQIVHPQSATPITVQDTHPSPTNRSKRNLK
MEIILTLSQGLKKYYGKILRLLQLTLEEDTEGLLEWCKRNLGLDCDDTFF
QKRIEEFFITGEGHFNEVLQFRTPGTLSTTESTPAGLPTAEPFKSYFAKG
FLSIDSGYYSAKCYSGTSNSGLQLINITRHSTRIVDTPGPKITNLKTINC
INLKASIFKEHREVEINVLLPQVAVNLSNCHVVIKSHVCDYSLDIDGAVR
LPHIYHEGVFIPGTYKIVIDKKNKLNDRCTLFTDCVIKGREVRKGQSVLR
QYKTEIRIGKASTGFRRLLSEEPSDDCVSRTQLLRTETAEIHGDNYGGPG
DKITICNGSTIVDQRLGSELGCYTINRVRSFKLCENSATGKNCEIDSVPV
KCRQGYCLRITQEGRGHVKLSRGSEVVLDACDTSCEIMIPKGTGDILVDC
SGGQQHFLKDNLIDLGCPKIPLLGKMAIYICRMSNHPKTTMAFLFWFSFG
YVITCILCKAIFYLLIIVGTLGRRLKQYRELKPQTCTICETTPVNAIDAE
MHDLNCSYNICPYCASRLTSDGLARHVIQCPKRKEKVEETELYLNLERIP
WVVRKLLQVSESTGVALKRSSWLIVLLVLFTVSLSPVQSAPIGQGKTIEA
YRAREGYTSICLFVLGSILFIVSCLMKGLVDSVGNSFFPGLSICKTCSIS
SINGFEIESHKCYCSLFCCPYCRHCSTDKEIHKLHLSICKKRKTGSNVML
AVCKLMCFRATMEVSNRALFIRSIINTTFVLCILILAVCVVSTSAVEMEN
LPAGTWEREEDLTNFCHQECQVTETECLCPYEALVLRKPLFLDSTAKGMK
NLLNSTSLETSLSIEAPWGAINVQSTYKPTVSTANIALSWSSVEHRGNKI
LVSGRSESIMKLEERTGISWDLGVEDASESKLLTVSVMDLSQMYSPVFEY
LSGDRQVEEWPKATCTGDCPERCGCTSSTCLHKEWPHSRNWRCNPTWCWG
VGTGCTCCGLDVKDLFTDYMFVKWKVEYIKTEAIVCVELTSQERQCSLIE
AGTRFNLGPVTITLSEPRNIQQKLPPEIITLHPRIEEGFFDLMHVQKVLS
ASTVCKLQSCTHGVPGDLQVYHIGNLLKGDKVNGHLIHKIEPHFNTSWMS
WDGCDLDYYCNMGDWPSCTYTGVTQHNHASFVNLLNIETDYTKNFHFHSK
RVTAHGDTPQLDLKARPTYGAGEITVLVEVADMELHTKKIEISGLKFASL
ACTGCYACSSSISCKVRIHVDEPDELTVHVKSDDPDVVAASSSLMARKLE
FGTDSTFKAFSAMPKTSLCFYIVEREHCKSCSEEDTKKCVNTKLEQPQSI
LIEHKGTIIGKQNSTCTAKASCWLESVKSFFYGLKNMLSGIFGNVFMGIF
LFLAPFILLILFFMFGWRILFCFKCCRRTRGLFKYRHLKDDEETGYRRII
EKLNNKKGKNKLLDGERLADGRIAELFSTKTHIG
                                            SEQ ID NO: 5
RRLLSEEPSDDCVSRTQLLRTETAEIHGDNYGGPGDKITICNGSTIVDQR
LGSELGCYTINRVRSFKLCENSATGKNCEIDSVPVKCRQGYCLRITQEGR
GHVKLSRGSEVVLDACDTSCEIMIPKGTGDILVDCSGGQQHFLKDNLIDL
```

GCPKIPLLGKMAIYICRMSNHPKTTMAFLFWFSFGYVITCILCKAIFYLL
IIVGTLGRRLKQYRELKPQTCTICETTPVNAIDAEMHDLNCSYNICPYCA
SRLTSDGLARHVIQCPKRKEKVEETELYLNLERIPWVVRKLL

SEQ ID NO: 6
RKPLFLDSTAKGMKNLLNSTSLETSLSIEAPWGAINVQSTYKPTVSTANI
ALSWSSVEHRGNKILVSGRSESIMKLEERTGISWDLGVEDASESKLLTVS
VMDLSQMYSPVFEYLSGDRQVEEWPKATCTGDCPERCGCTSSTCLHKEWP
HSRNWRCNPTWCWGVGTGCTCCGLDVKDLFTDYMFVKWKVEYIKTEAIVC
VELTSQERQCSLIEAGTRFNLGPVTITLSEPRNIQQKLPPEIITLHPRIE
EGFFDLMHVQKVLSASTVCKLQSCTHGVPGDLQVYHIGNLLKGDKVNGHL
IHKIEPHFNTSWMSWDGCDLDYYCNMGDWPSCTYTGVTQHNHASFVNLLN
IETDYTKNFHFHSKRVTAHGDTPQLDLKARPTYGAGEITVLVEVADMELH
TKKIEISGLKFASLACTGCYACSSSISCKVRIHVDEPDELTVHVKSDDPD
VVAASSSLMARKLEFGTDSTFKAFSAMPKTSLCFYIVEREHCKSCSEEDT
KKCVNTKLEQPQSILIEHKGTIIGKQNSTCTAKASCWLESVKSFFYGLKN
MLSGIFGNVFMGIFLFLAPFILLILFFMFGWRILFCFKCCRRTRGLFKYR
HLKDDEETGYRRIIEKLNNKKGKNKLLDGERLADGRIAELFSTKTHIG

SEQ ID NO: 7
GTTGGTGGTCGCCATGGATGGTGTTATTGTATACTGTCTAAACGCGTTAG
TAAAACATGGCGAGGAAATAAATCATATAAAAAATGATTTCATGATTAAA
CCATGTTGTGAAAAAGTCAAGAACGTTCACATTGGCGGACAATCTAAAAA
CAATACAGTGATTGCAGATTTGCCATATATGGATAATGCGGTATCCGATG
TATGCAATTCACTGTATAAAAGAATGTATCAAGAATATCCAGATTTGCT
AATTTGATAAAGATAGATGACGATGACAAGACTCCTACTGGTGTATATAA
TTATTTTAAACCTAAAGATGCCATTCCTGTTATTATATCCATAGGAAAGG
ATAGAGATGTTTGTGAACTATTAATCTCATCTGATAAAGCGTGTGCGTGT
ATAGAGTTAAATTCATATAAAGTAGCCATTCTTCCCATGGATGTTTCCTT
TTTTTACCAAAGGAAATGCATCATTGATTATTCTCCTGTTTGATTTCTCTA
TCGATGCGGCACCTCTCTTAAGAAGTGTAACCGATAATAATGTTATTATA
TCTAGACACCAGCGTCTACATGACGAGCTTCCGAGTTCCAATTGGTTCAA
GTTTTACATAAGTATAAAGTCCGACTATTGTTCTATATTATATATGGTTG
TTGATGGATCTGTGATGCATGCAATAGCTGATAATAGAACTTACGCAAAT
ATTAGCAAAATATATTAGACAATACTACAATTAACGATGAGTGTAGATG
CTGTTATTTTGAACCACAGATTAGGATTCTTGATAGAGATGAGATGCTCA
ATGGATCATCGTGTGATATGAACAGACATTGTATTATGATGAATTTACCT
GATGTAGGCGAATTTGGATCTAGTATGTTGGGGAAATATGAACCTGACAT
GATTAAGATTGCTCTTTCGGTGGCTGGGTACCAGGCGCGCCTTTCATTTT
GTTTTTTTCTATGCTATAAATGGTGAGCAAGGGCGAGGAGCTGTTCACCG
GGGTGGTGCCCATCCTGGTCGAGCTGGACGGCGACGTAAACGGCCACAAG
TTCAGCGTGTCCGGCGAGGGCGAGGGCGATGCCACCTACGGCAAGCTGAC
CCTGAAGTTCATCTGCACCACCGGCAAGCTGCCCGTGCCCTGGCCCACCC
TCGTGACCACCCTGACCTACGGCGTGCAGTGCTTCAGCCGCTACCCCGAC

CACATGAAGCAGCACGACTTCTTCAAGTCCGCCATGCCCGAAGGCTACGT
CCAGGAGCGCACCATCTTCTTCAAGGACGACGGCAACTACAAGACCCGCG
CCGAGGTGAAGTTCGAGGGCGACACCCTGGTGAACCGCATCGAGCTGAAG
GGCATCGACTTCAAGGAGGACGGCAACATCCTGGGGCACAAGCTGGAGTA
CAACTACAACAGCCACAACGTCTATATCATGGCCGACAAGCAGAAGAACG
GCATCAAGGTGAACTTCAAGATCCGCCACAACATCGAGGACGGCAGCGTG
CAGCTCGCCGACCACTACCAGCAGAACACCCCCATCGGCGACGGCCCCGT
GCTGCTGCCCGACAACCACTACCTGAGCACCCAGTCCGCCCTGAGCAAAG
ACCCCAACGAGAAGCGCGATCACATGGTCCTGCTGGAGTTCGTGACCGCC
GCCGGGATCACTCTCGGCATGCACGAGCTGTACAAGTAAGCGGCCGCTGG
TACCCAACCTAAAAATTGAAAATAAATACAAAGGTTCTTGAGGGTTGTGT
TAAATTGAAAGCGAGAAATAATCATAAATAAGCccggtGCCACCATGgat
gcaatgaagagagggctctgctgtgtgctgctgctgtgtggagcagtctt
cgtttcgcccagccaggaaatccatgcccgattcagaagaggagccagat
ctcccATCAAACAAGTTTGTACAAAAAAGCAGGCTcatatatcattaatg
tatgcaatcctttgcctacagctgtgtggtctgggagagactcatggatc
acacaatgaaactagacacaataaaacagacaccatgacaacacacggtg
ataacccgagctctgaaccgccagtgagcacggccttgtctattacactt
gaccctccactgtcacacccacaacaccagccagtggattagaaggctc
aggggaagtctacacatcccctccgatcaccaccgggagcttgcccctgt
cggagacaacaccagaactccctgttacaaccggcacagacaccttaagc
gcaggtgatgtcgatcccagcacgcagacagccggaggcacctccgcacc
aacagtccgcacaagtctacccaacgccctagcacaccatctacaccac
aagacacacaccatcctgtgagaaatctactttcagtcacgagtcctggg
ccagatgaaacatcaaccctcgggaacaggcaaagagagctcagcaac
cagtagccctcatccagtctccaacagaccaccaaccctcctgcaacag
cccaggacccactgaaaatgacagtcacaacgccactgaacaccctgag
tccctgacacagtcagcaaccccaggcctaatgacctctccaacacagat
agtccacccacaaagtgccacccccataaccgttcaagacacacatccca
gtccaacgaacaggtctaaaagaaaccttaagatggaaataatcttgact
ttatctcagggttaaaaaagtactatgggaaatattaaggcttctgca
actcaccttagaggaggacactgaaggtctactggaatggtgtaagagaa
atcttggtcttgattgtgatgacacttcttccaaaagagaattgaagaa
ttctttataactggtgagggccattttaatgaagttttacaatttagaac
gccaggcacgttgagcaccacagagtcaacacctgctgggctgccaacag
ctgaaccttttaagtcctacttcgccaaaggcttcctctcgatagattca
ggttactactcagccaaatgttactcaggaacatccaattcagggcttca
attgattaacattacccgacattcaactagaatagttgacacacctgggc
ctaagatcactaacctaaagaccatcaactgcataaacttgaaggcatcg
atcttcaaagaacatagagaggttgaaatcaatgtgcttctccccccaagt -continued tgcagttaatctctcaaactgtcacgttgtaatcaaatcacatgtctgtg
actactctttagacattgacggtgcggtgaggcttcctcacatttaccat
gaaggagttttcatcccaggaacttacaaaatagtgatagataaaaaaaa
taagttgaatgacagatgcaccttatttaccgactgtgtgataaaaggaa
gggaggttcgtaaaggacagtcagttttgaggcagtacaagacggaaatc
aggattggcaaggcatcaaccggctttagaagattgctttcagaagaacc
cagtgatgactgtgtatcaagaactcaactattaaggacagagactgcag
agatccacggcgacaactatggtggcccgggtgacaaaataaccatctgc
aatggctcaactattgtagaccaaagactgggcagtgaactaggatgcta
caccatcaatagagtgaggtcattcaagctatgcgaaaacagtgccacag
ggaagaattgtgaaatagacagtgtcccagttaaatgcaggcagggttat
tgcctaagaatcactcaggaagggaggggccacgtaaaattatctagggg
ctcagaggttgtcttagatgcatgcgatacaagctgtgaaataatgatac
ctaagggcactggtgacatcctagttgactgttcaggtgggcagcaacat
tttctaaaggacaatttgatagatctaggatgccccaaaattccattatt
gggcaaaatggctatttacatttgcagaatgtcaaaccaccccaaaacaa
ccatggctttcctcttctggttcagctttggctatgtaataacctgcata
ctttgcaaggctatttttacttgttaataattgttggaacactagggag
aaggctcaagcagtatagagagttgaaacctcagacttgcaccatatgtg
agacaactcctgtaaatgcaatagatgctgagatgcatgacctcaattgc
agttacaacatttgtccctactgtgcatctagactaacctcagatgggct
tgctaggcatgtgatacaatgccctaagcggaaggagaaagtggaagaaa
ctgaactgtacttgaacttagaaagaattccttgggttgtaagaaagctg
ttgcaggtgtcagagtcaactggtgtggcattgaaaagaagcagttggct
gattgtgctgcttgtgctattcactgtttcattatcaccagttcaatcag
cacccattggtcaagggaagacaattgaggcataccgggccagggaaggg
tacacaagtatatgcctctttgtactaggaagtatcctatttatagtttc
ttgcctaatgaaagggctggttgacagtgttggcaactccttcttccctg
gactgtccatttgcaaaacgtgctccataagcagcattaatggctttgaa
attgagtcccataagtgctattgcagcttattctgttgccctattgtag
gcactgctctaccgataaagaaattcataagctgcacttgagcatctgca
aaaaaggaaaacaggaagtaatgtcatgttggctgtctgcaagctcatg
tgtttcaggccaccatggaagtaagtaacagagccctgtttatccgtag
catcatcaacaccacttttgttttgtgcatactgatactagcagtttgtg
ttgttagcacctcagcagtggagatgaaaacctaccagcagggacctgg
gaaagagaagaagacctaacaaaattctgtcatcaggaatgccaggttac
agagactgaatgcctctgcccttatgaagctctagtactcagaaagcctt
tattcctagatagtacagctaaaggcatgaaaaatctgctaaattcaaca
agtttagaaacgagtttatcaattgaggcaccatggggagcaataaatgt
tcagtcaacctacaaaccaactgtgtcaactgcaaacatagcactcagtt
ggagctcagtggaacacagaggcaataagatcttggtttcaggcagatca -continued gaatcaattatgaagctggaagaaaggacaggaatcagctgggatctcgg
tgtagaagatgcctctgaatctaaactgcttacagtatctgtcatggact
tgtctcagatgtactctcctgtcttcgagtacttatcaggggacagacag
gtggaagagtggcccaaagcaacttgcacaggtgactgcccagaaagatg
tggctgcacatcatcaacctgtttgcacaaagaatggcctcactcaagaa
attggagatgcaatcccacttggtgctggggtgagggactggctgcacc
tgttgtggattagatgtgaaagacctttttacagattatatgtttgtcaa
gtggaaagttgaatacatcaagacagaggccatagtgtgtgtagaactta
ctagtcaggaaaggcagtgtagcttgattgaagcgggcacaaggttcaat
ttaggtcctgtgaccatcacactgtcagaaccaagaaacatccaacaaaa
actccctcctgaaataatcacactgcatcctaggatcgaagaaggtttCt
ttgacctgatgcatgtgcaaaaggtgttatcggcaagcacagtgtgtaag
ttgcagagttgcacacatggtgtgccaggagacctacaggtctaccacat
cggaaatttattaaaaggggataaggtaaatggacatctaattcataaaa
ttgagccacacttcaacacctcctggatgtcctgggatggttgtgaccta
gactactactgcaacatgggagattggccttcttgcacatacacagggt
cacccaacacaatcatgcttcatttgtaaacttactcaacattgaaactg
attacaaagaacttccactttcactctaaaagggtcactgcacacgga
gatacaccacaactagatcttaaggcaagaccaacctatggtgcaggcga
gatcactgttctggtagaagttgctgacatggagttacatacaaagaaga
ttgaaatatcaggcttaaaatttgcaagcttagcttgcacaggttgttat
gcttgtagctctagcatctcatgcaaagttagaattcatgtggatgaacc
agatgaacttacagtacatgttaaaagtgatgatccagatgtggttgcag
ctagctcaagtctcatggcaaggaagcttgaatttggaacagacagtaca
tttaaagctttctcggccatgcctaaaacttctctatgtttctacattgt
tgaaagagaacactgtaagagctgcagtgaagaagacacaaaaaaatgtg
ttaacacaaaacttgagcaaccacaaagcattttgatcgaacacaaggga
actataatcggaaagcaaaacagcacttgcacggctaaggcaagttgctg
gttagagtcagtcaagagtttCttttatggcctaaagaacatgcttagtg
gcattttggcaatgtctttatgggcattttcttgttccttgccccttc
atcctgttaatactattctttatgtttgggtggaggatcctattctgctt
taaatgttgtagaagaaccagaggcctgttcaagtatagacacctcaaag
acgatgaagaaactggttatagaaggattattgaaaaactaaacaataaa
aaaggaaaaacaaactgcttgatggtgaaagacttgctgatggaagaat
tgccgaactgttctctacaaaaacacacattggcACCCAGCTTTCTTGTA
CAAAGTGGTTCGATggggatctagagggcccgcggttcgaaggtaagcct
atccctaaccctctcctcggtctcgattctacgtaaGTCGACCTGCAGGG
AAAGTTTTATAGGTAGTTGATAGAACAAAATACATAATTTTGTAAAAATA
AATCACTTTTTATACTAATATGACACGATTACCAATACTTTTGTTACTAA
TATCATTAGTATACGCTACACCTTTTCCTCAGACATCTAAAAAAATAGGT -continued
```
GATGATGCAACTTTATCATGTAATCGAAATAATACAAATGACTACGTTGT

TATGAGTGCTTGGTATAAGGAGCCCAATTCCATTATTCTTTTAGCTGCTA

AAAGCGACGTCTTGTATTTTGATAATTATACCAAGGATAAAATATCTTAC

GACTCTCCATACGATGATCTAGTTACAACTATCACAATTAAATCATTGAC

TGCTAGAGATGCCGGTACTTATGTATGTGCATTCTTTATGACATCGCCTA

CAAATGACACTGATAAAGTAGATTATGAAGAATACTCCACAGAGTTGATT

GTAAATACAGATAGTGAATCGACTATAGACATAATACTATCTGGATCTAC

ACATTCACCAGAAACTAGTT
```

EXAMPLES

Example 1. Preparation of an Example MVA-GP (Glycoprotein) Vector (FIG. 1A-1C)

The sequence of the CCHFV M segment was taken from published sequence data on the IbAr10200 CCHFV strain.

The M segment sequence was modified for improved compatibility with MVA expression. M segment untranslated regions were deleted, start and stop codons were deleted, and 2×TTTTTNT sequences (poxvirus transcription stop signals) silently mutated. attB1 and attB2 sequences were added for compatibility with the proprietary cloning system used (Gateway Cloning, by Invitrogen).

Tissue Plasminogen Activator (tPA) signal sequence (for increased immunogenicity and intracellular transport) and V5 fusion protein sequence (for identification of expressed protein by immunolabeling) were added.

The construct was synthesised and recombined into a pDONR vector to generate Entry Clone plasmid (pENTR-GP).

The plasmid was then recombined with Destination vector pDEST44-TPA-V5 to generate pTP-GP plasmid.

This resulted in the gene for tPA-GP-V5 fusion protein downstream of the poxvirus mH5 promoter. This promoter was chosen for increased stability and strong early expression, to drive a cytotoxic T lymphocyte response.

pTP-GP was transfected into MVA-infected cells. Recombination occurs between the MVA flanks on the plasmid and in the MVA genome, inserting the GFP and GP cassette into the MVA genome. The MVA strain used was MVA 1974/NIH clone 1.

Figure 15A:
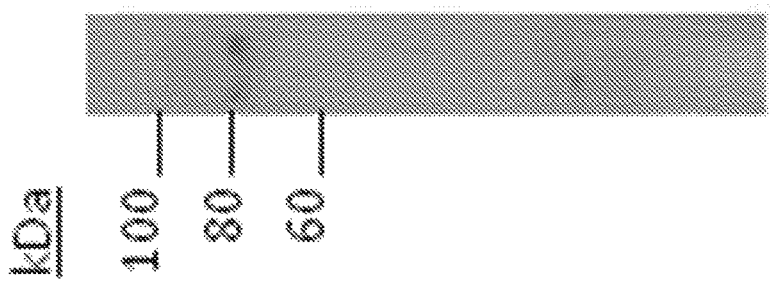
FIG. 15.

MVA-GP was plaque-purified based on GFP expression and underwent quality checks: confirmation of purity by PCR, confirmation of GP expression by Western blot (FIG. 15A), and sequencing of the insertion site.

SDS-PAGE of MVA-GP and Western blotting with anti-V5 antibody (FIG. 15A) indicated a single protein of approximately 75 kDa, confirming expression and consistent with cleavage of the predicted 76.6 kDa Gc-V5 fusion protein from the GP precursor at RKPL sequence.

Figure 15B:
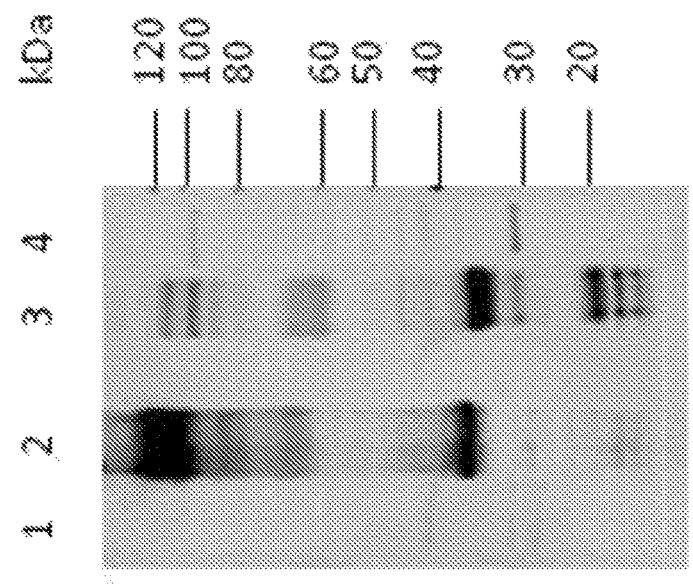

SDS-PAGE and Western blotting with anti-glycoprotein polyclonal serum were performed, in order to compare glycoprotein expression by MVA-GP with CCHFv (FIG. 15B). Several products were expressed by CCHFv (lane 3). Some of these were also detected in uninfected SW13 cells (lane 4), suggesting a possible cross-reaction with cellular proteins. CCHFv-specific products were detected at approximately 109, 60, 34 and <20 kDa. Similarly, sucrose cushion-purified MVA-GP expressed major proteins at approximately 92-136, 64 and 35 kDa (lane 2). Sucrose cushion-purified MVA-1974 (a negative control) did not show any products of a similar size (lane 1), confirming all products in lane 2 as specific to the recombinant vaccine.

The appropriate clone of MVA-GP was amplified, purified by sucrose cushion centrifugation and titrated by plaque assay.

Example 2. MVA-GP Immunogenicity in Balb/c Mice

11 Balb/c mice were injected intramuscularly with $10^7$ plaque-forming units (pfu) per animal of MVA-GP, prepared according to Example 1. A volume of 100 µl was delivered, split into two sites at 50 µl each. Animals received 2 vaccinations, spaced 2 weeks apart. Control animals (n=9) received saline.

Eight days after the final vaccination, 5 (MVA-GP) or 4 (saline) mice were sacrificed for T cell immunogenicity testing. The remaining animals were sacrificed 14 days after the final vaccination.

Animals immunised with MVA-GP showed a significant antigen response to CCHF glycoprotein peptides as compared to control animals (FIG. 2).

Examples 3 and 4 (described below) utilise an animal model that replicates lethal disease in mice that are infected with CCHF virus. In vaccine efficacy experiments, all animals that were vaccinated with MVA-GP survived a lethal challenge dose of CCHFV. Those animals that received a mock immunisation with (i) saline or (ii) a simple MVA preparation all succumbed to disease and met humane clinical endpoints by five days post-challenge.

Example 3. MVA-GP Vaccine Efficacy Study in Mouse Model (Mouse Strains A129 and 129Sv/Ev)

This in vivo efficacy study used both type-1 interferon receptor knockout (A129) and wild-type (129Sv/Ev) mice which were immunised with MVA containing CCHF virus glycoprotein (MVA-GP), construct alone (MVA-empty) and saline. A129 mice are susceptible to CCHF virus infection, and the 129Sv/Ev are the wild-type parent strain. Mice were immunised at day 0, and then boosted at day 14. 7 days after the last immunisation, 5 animals from each group were used to assess immune response. 14 days after the last immunisation, A129 mice from each immunisation group were challenged with $10^2$ $TCID_{50}$ CCHF virus, delivered intradermally. 6 challenged animals from each group were observed for up to 10 days post-challenge for survival studies.

Figure 3:
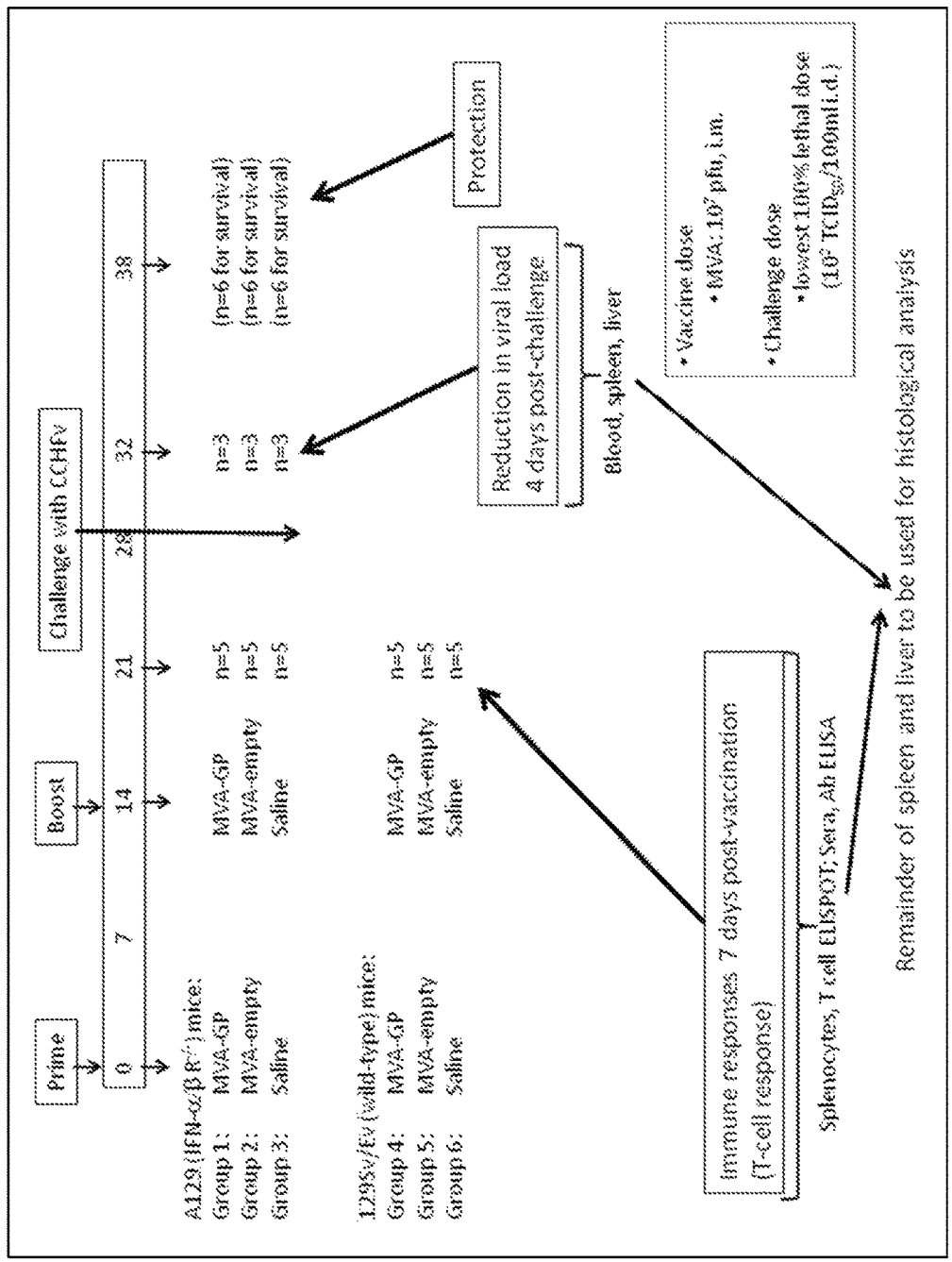
Figure 4A:
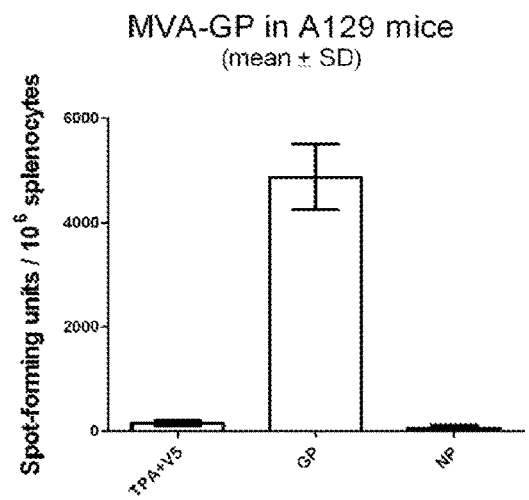
FIG. 4A-B. IFN-γ ELISPOT results.
Figure 4A:
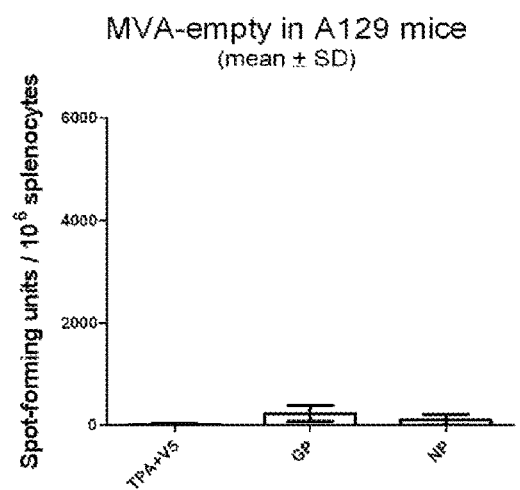
Figure 4A:
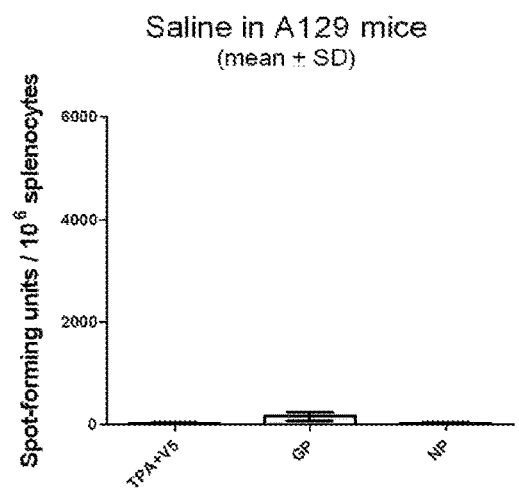
Figure 4B:
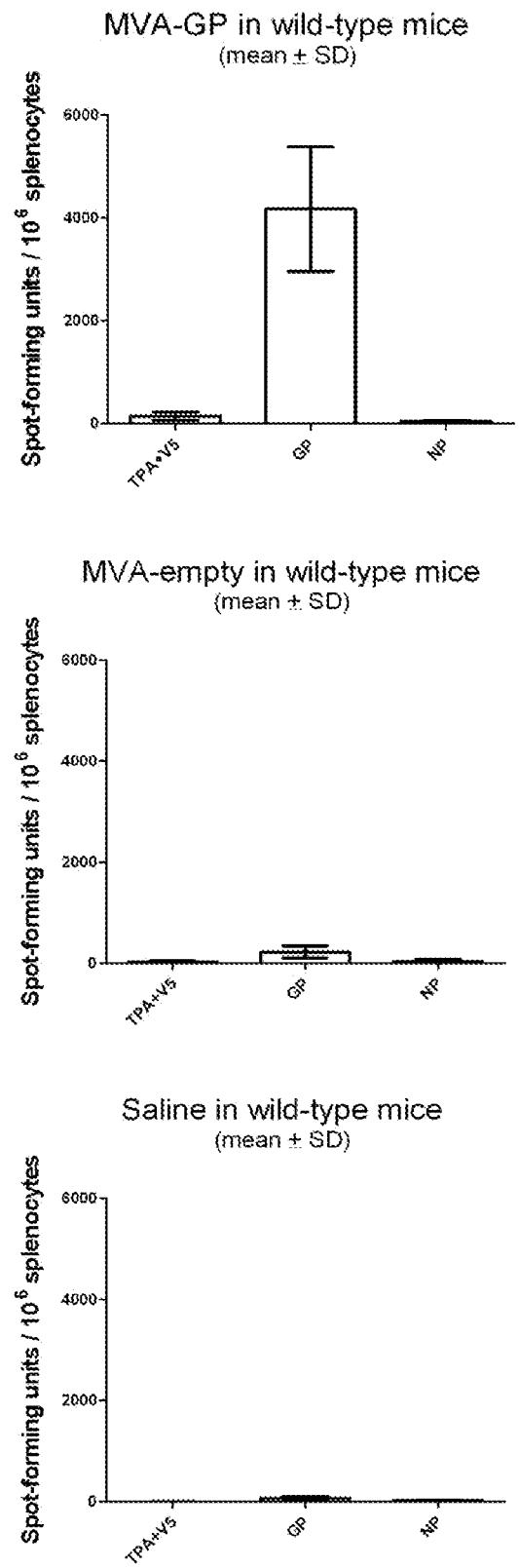
Figure 5A:
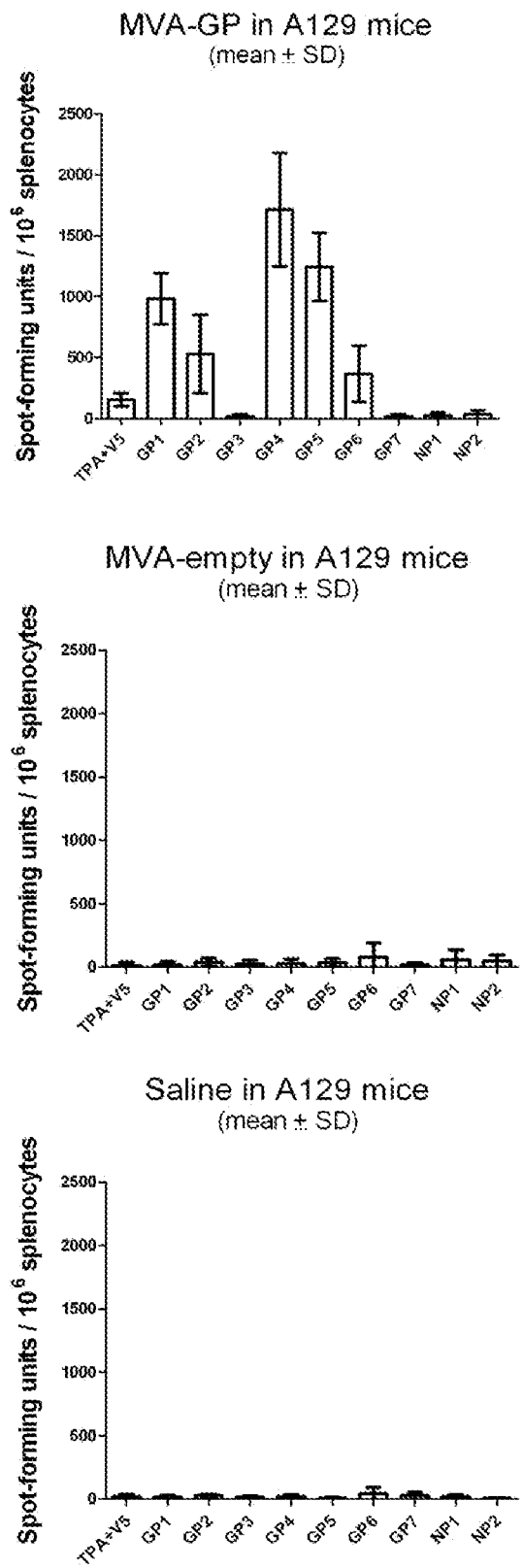

Experimental protocol is depicted in FIG. 3.

Results: IFN-γ ELISPOT results showed that MVA-GP immunised mice generated immune responses specific to the CCHFv glycoproteins that they were immunised with. Statistically similar results were observed between both strains after MVA-GP immunisation (P<0.05, Mann-Whitney statistical test). T-cell responses to peptides derived from the TPA/V5 fusion proteins, or from an irrelevant antigen (NP) were negligible, indicating specificity of the response. (FIG. 4).

When the responses shown in FIG. 4 were subdivided into the peptide pools (1 for TPA/V5, 4 for GP, 3 for GC and 2 for NP) the same pools were optimal between strains. Some peptide pools were consistently non-immunogenic. (FIG. 5).

Figure 6:
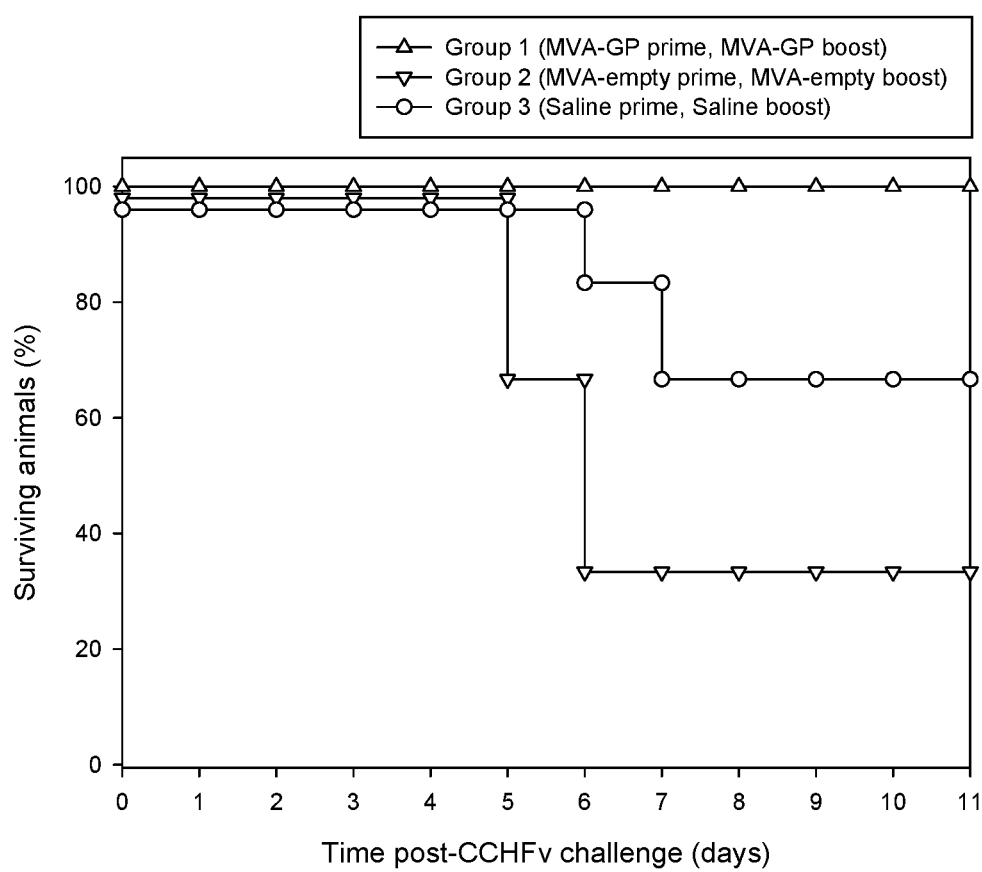
FIG. 6. Animal survival rates following CCHFV challenge (Example 3).

After challenge with CCHF virus, control groups of saline and MVA-empty showed 66% survival and 33% survival, respectively. 100% survival was observed with 2×MVA-GP group. (FIG. 6).

Figure 7A:
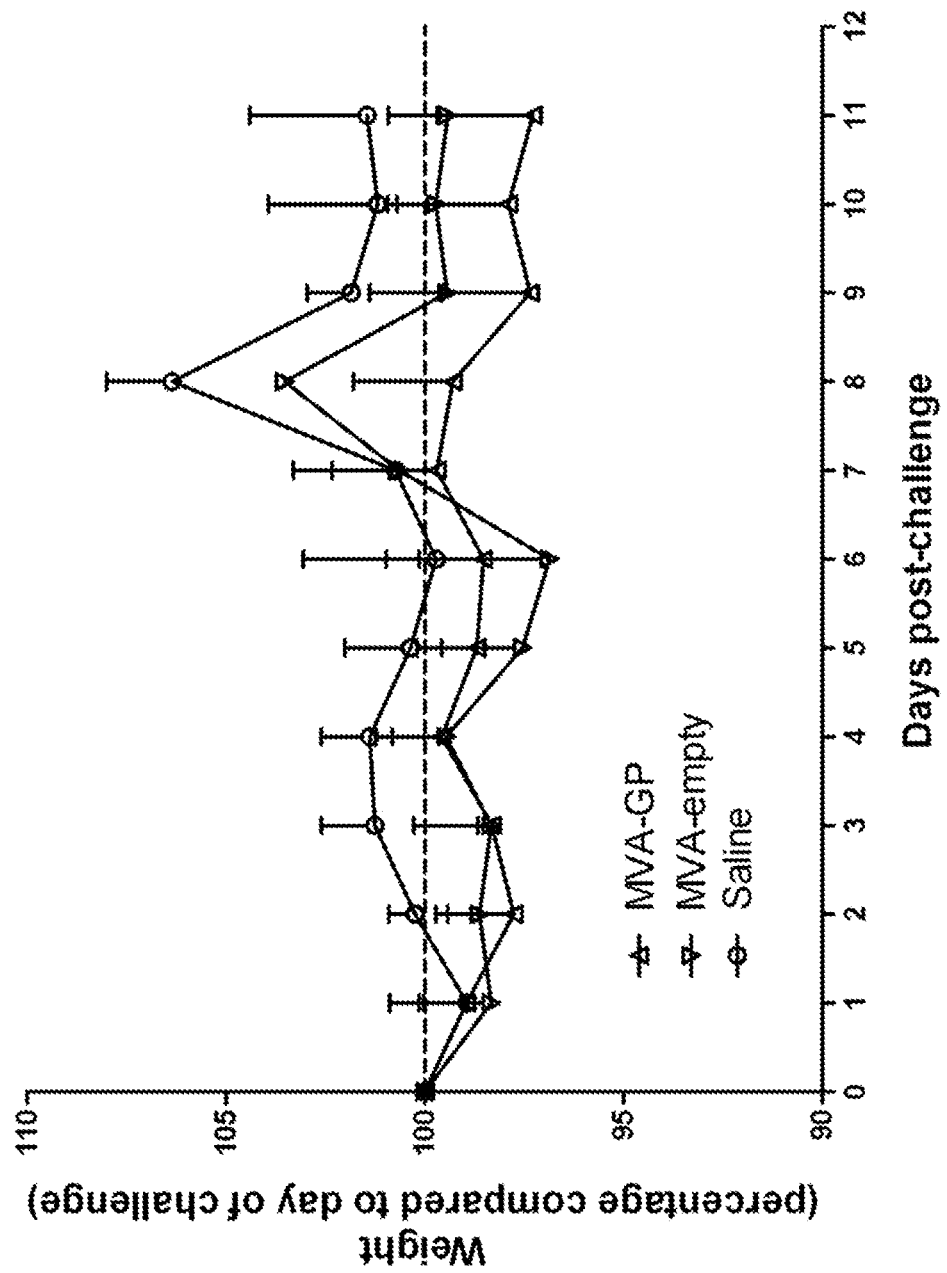
FIG. 7A-B. Weight loss in study animals (Example 3).
Figure 7B:
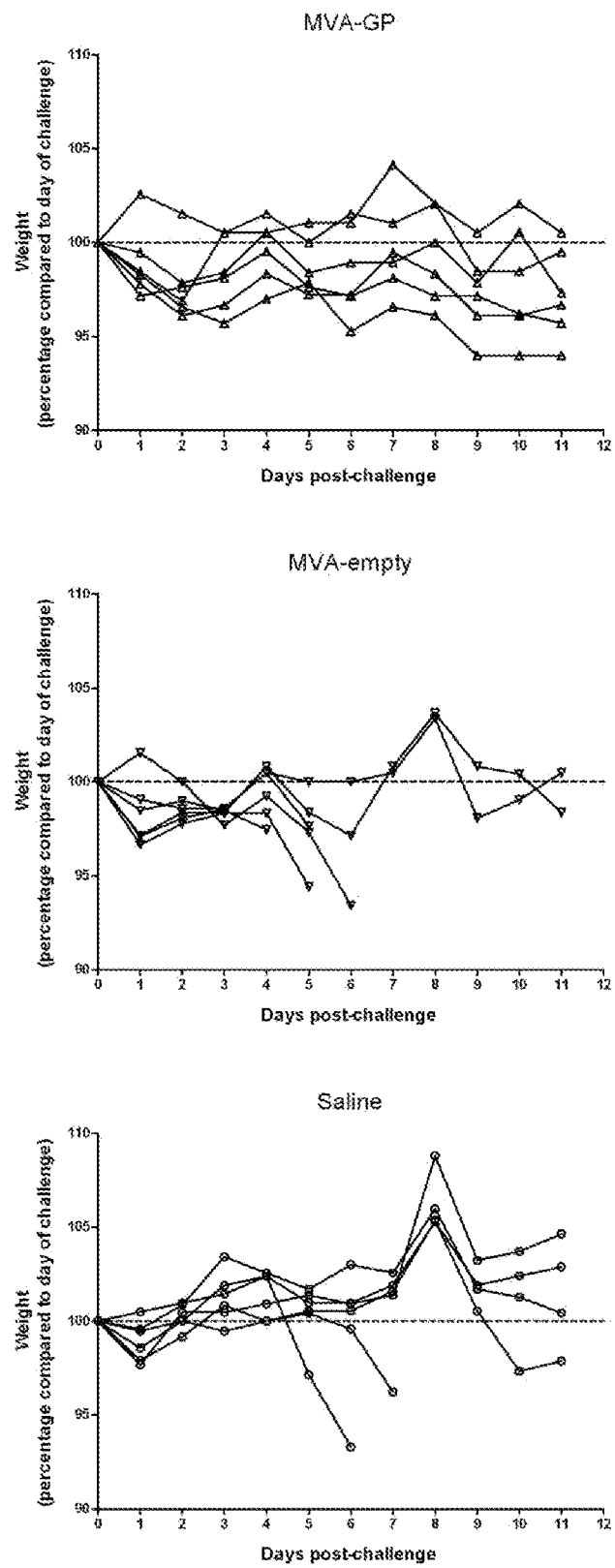

Weight loss was seen in animals that reached humane clinical endpoints in control groups 2 and 3. Some of the vaccinated animals in the 100% survival group showed evidence of weight loss, indicative of disease/illness. (FIG. 7).

Figure 8A:
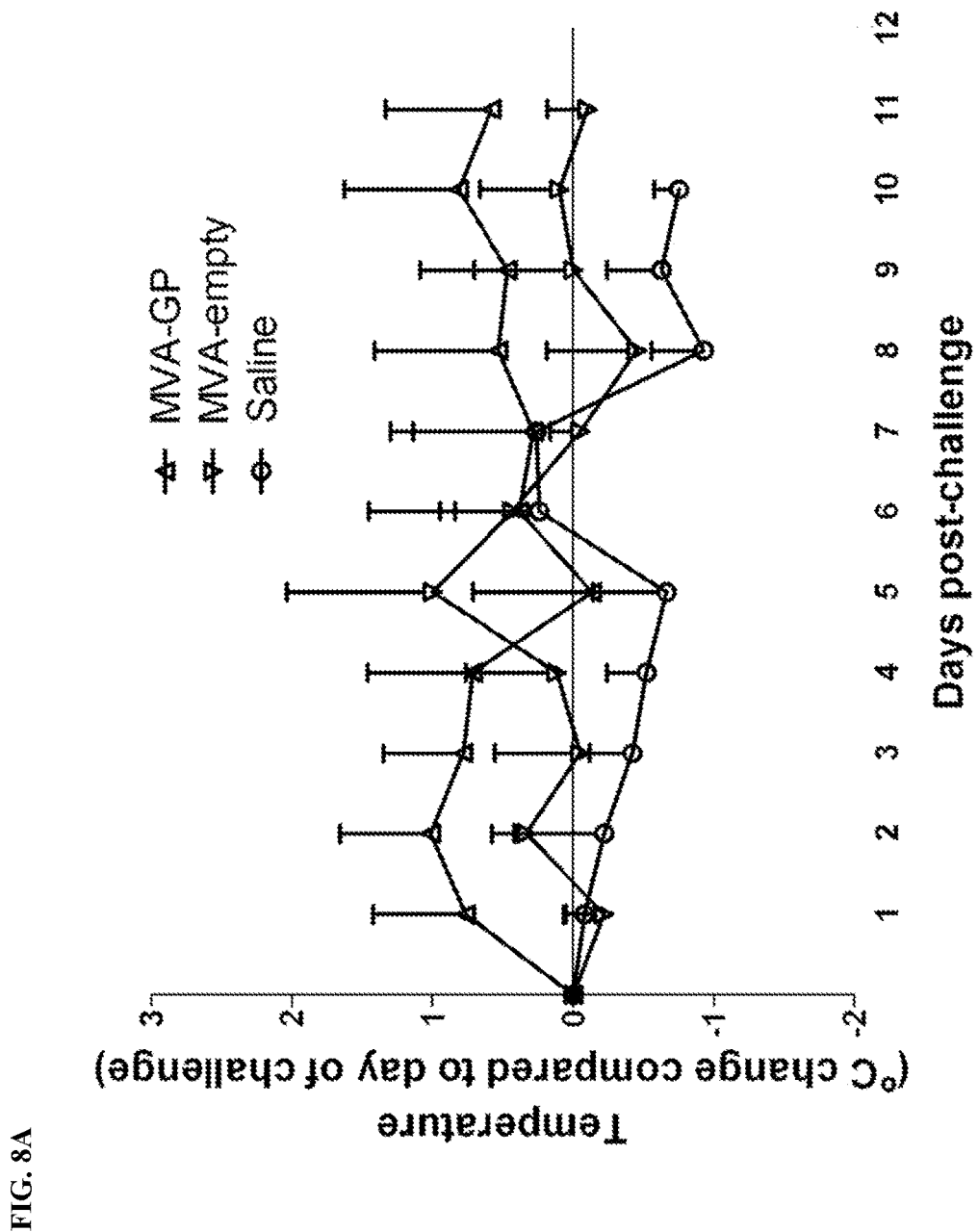
FIG. 8A-B. Temperature rise in study animals (Example 3).
Figure 8B:
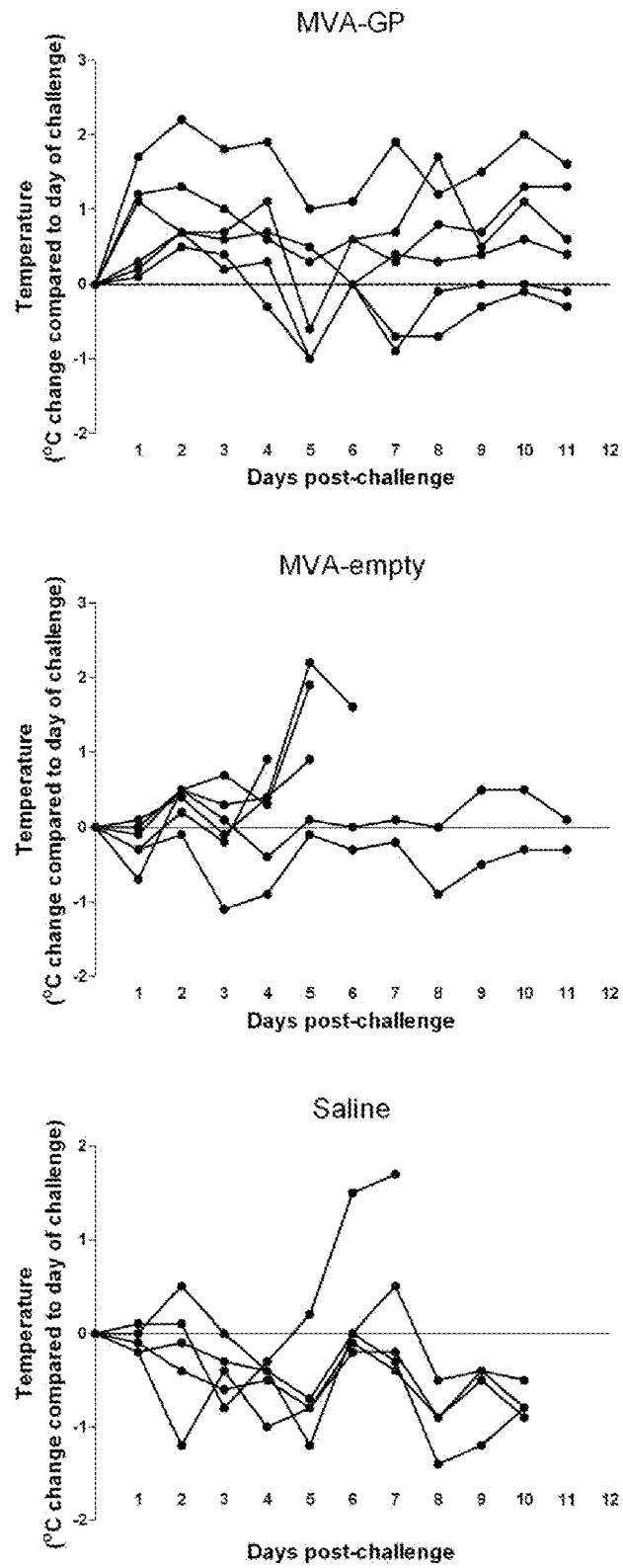

Animals that reached humane clinical endpoints in groups 2 (MVA-empty) and 3 (saline control) also exhibited a rise in temperature at days 5-7 post-challenge. Temperatures fluctuated in the MVA-GP immunised animals, but no trend was observed. (FIG. 8).

Conclusions:
MVA-GP is immunogenic, producing protein-specific immune responses.
No differences were observed in the immune response to MVA-GP between wild-type mice (129Sv/Ev) and those with a knockout in the type-1 interferon receptor (A129).
All MVA-GP immunised animals survived a challenge with $10^2$ $TCID_{50}$ CCHF virus (strain IbAr10200).
Animals which reached humane clinical endpoints in the MVA-empty and saline groups exhibited a rise in temperature and weight loss.

Example 4. MVA-GP Vaccine Efficacy Study in Mouse Model (Mouse Strain A129)

The study described above in Example 3 found $10^2$ $TCID_{50}/100$ µl delivered intradermally (i.d.) to have 34% lethality in saline 'vaccinated' 10 week old IFN-α/βR$^{-/-}$ mice. Therefore this study used $2\times10^2$ $TCID_{50}/100$ µl of strain IbAr10200 delivered i.d. as the challenge dose to IFN-α/βR$^{-/-}$ mice.

Prior to challenge, animals were vaccinated with MVA-GP derived from strain IbAr10200. Vaccinations were given intramuscularly (i.m.) into the caudal thigh at a dose of $10^7$ plaque-forming units (pfu) per animal. A volume of 100 µl was delivered, split into two sites at 50 µl each. Animals received 2 vaccinations, spaced 2 weeks apart. Two weeks elapsed between final vaccination and challenge.

Control groups were vaccinated with saline (groups 1 & 6), or MVA-empty (group 2), which is unmodified, non-recombinant MVA.

Representatives from each vaccination group were sacrificed 7 days post-final vaccination, for histology and immunogenicity (T-cell and antibody) testing. Further animals were sacrificed 4 days post-challenge, for histology and viral load testing. After challenge, animals were weighed and temperature monitored daily, and observed for signs of illness twice daily.

Animals showing moderate symptoms (such as loss of 10% body weight, shaking or paralysis) were euthanised. Spleen and liver samples were collected from animals that reached humane clinical endpoints. At 14 days post-challenge, all remaining animals were culled and samples collected for histology and viral load testing.

Figure 9:
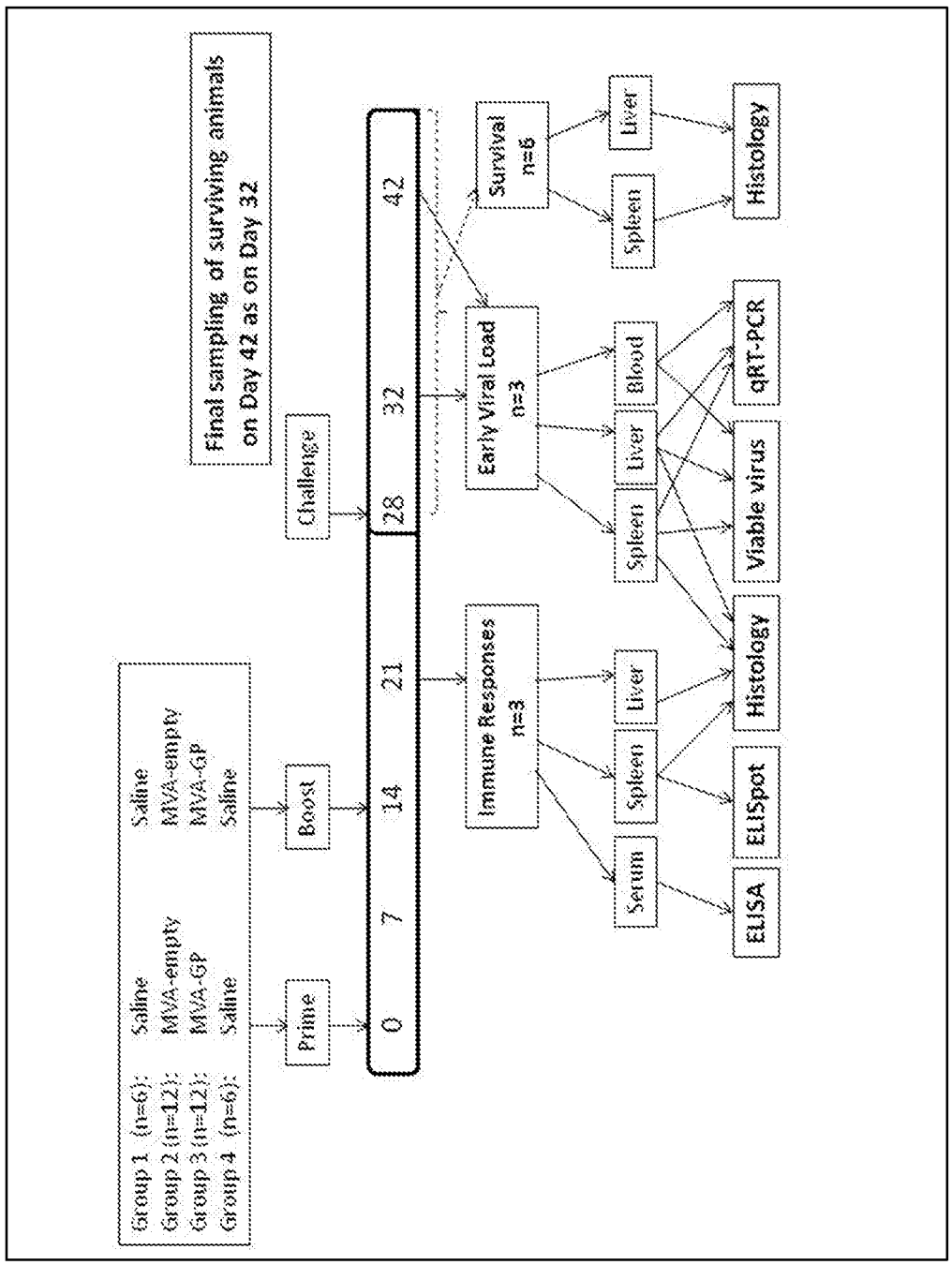
FIG. 9. Experimental protocol for Example 4.

Experimental protocol is depicted in FIG. 9.

Results—Survival.

Figure 10:
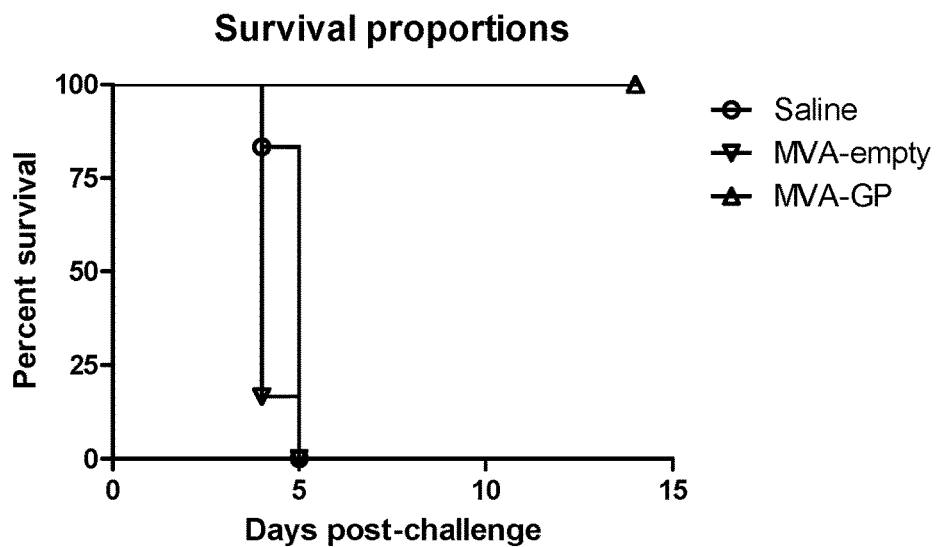
FIG. 10. Animal survival rates following CCHFV challenge (Example 4).

100% protection was achieved with MVA-GP (survival 2 weeks post-challenge). All other groups died 4-5 days post-challenge. (FIG. 10).

Results—Clinical Data.

Figure 11:
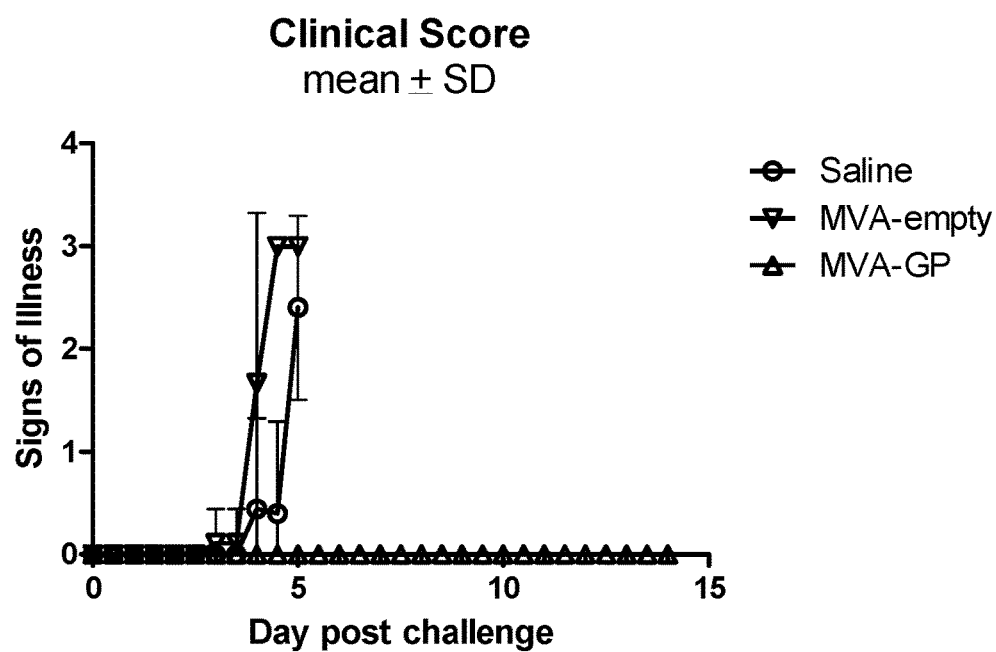
FIG. 11. Animal clinical scores (Example 4).

MVA-GP showed no signs of disease. Control groups showed severe illness and were euthanized. (FIG. 11).

Figure 12:
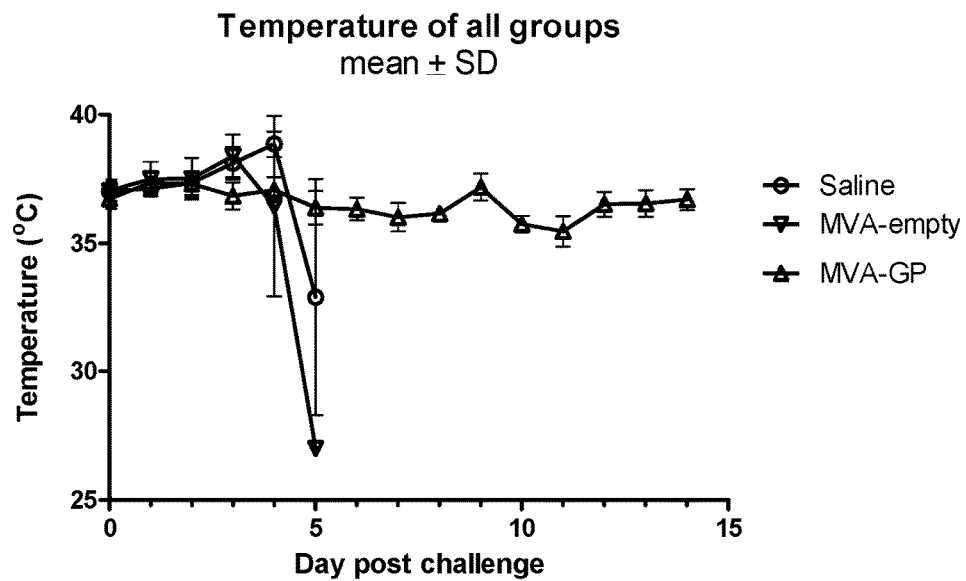
FIG. 12. Animal temperature scores (Example 4).

MVA-GP temperature was stable whilst other groups were succumbing, but slight spike in temperature at 9 days post-challenge. Control groups showed spike in temperature, then sharp reduction as succumbed to disease. (FIG. 12).

Figure 13:
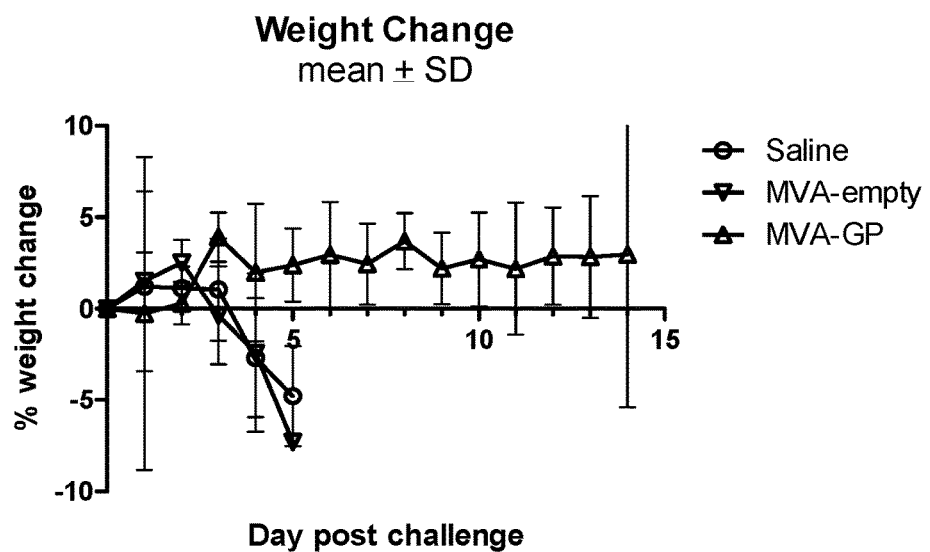
FIG. 13. Animal weight change scores (Example 4).

MVA-GP showed some weight loss at days 4-5, then stable, but did not regain peak weight. Control groups lost 5-10% of body weight. (FIG. 13).

Results—Immune Responses (ELISpot)

Figure 14A:
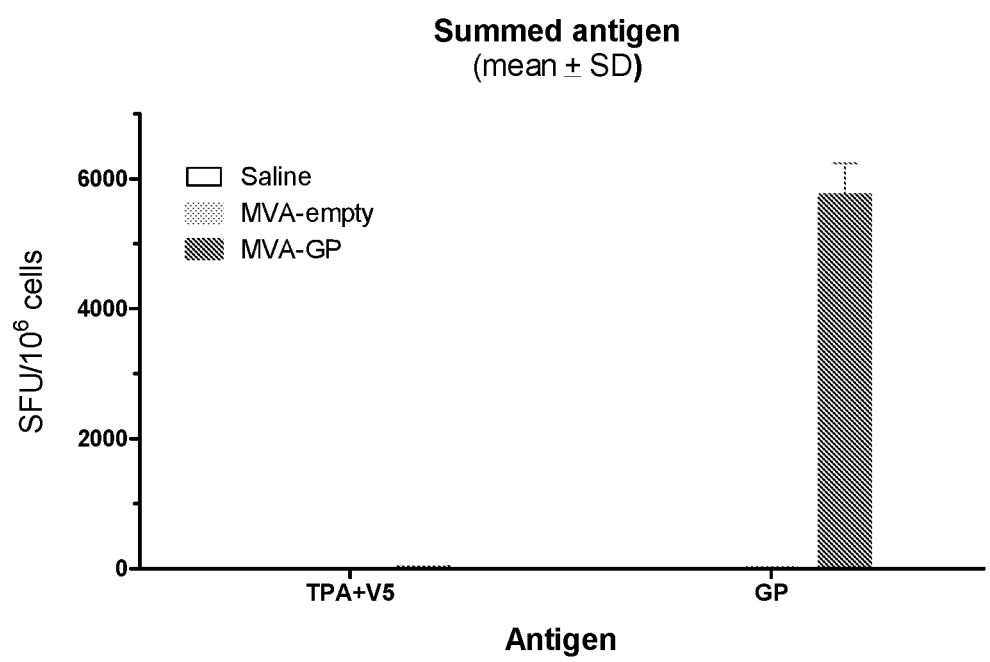
FIG. 14A-B. Animal immune responses (Example 4).
Figure 14B:
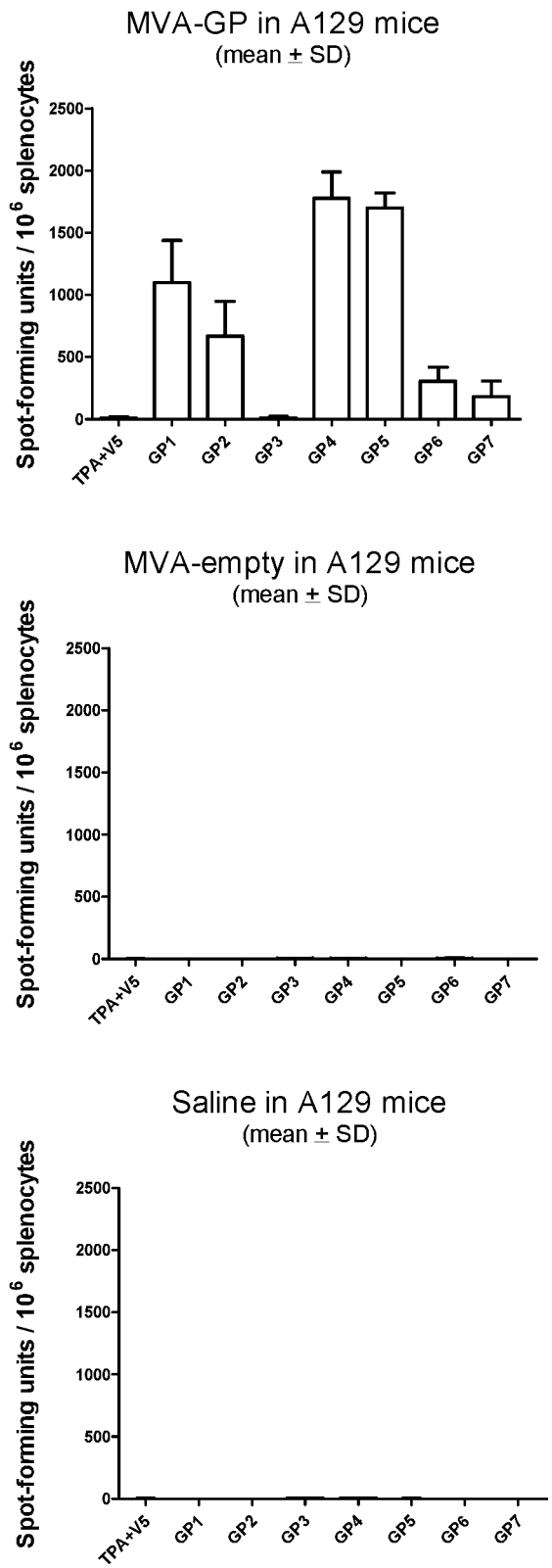

IFN-γ ELISpot on splenocytes 7 days post-boost showed T-cell immunogenicity of GP. Low immunogenicity from TPA & V5 fusion tags (FIG. 14A). GP\ peptide pools showed that density of epitopes varied across the GP protein. (FIG. 14B).

Western Blotting

Figure 16:
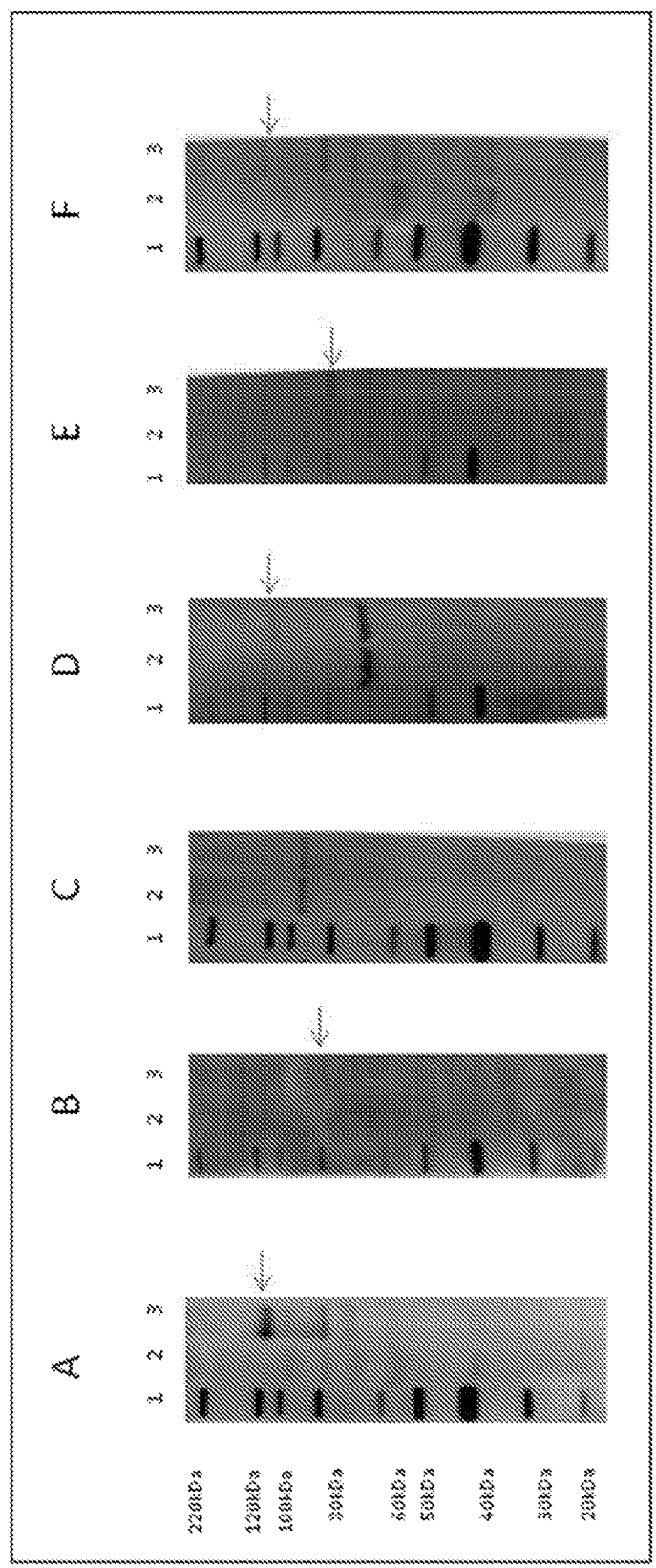

Immunised animals (including those used in Example 3) were also tested for induction of a CCHFv-specific humoral response by MVA-GP, using Western Blotting. IgG antibody reacting with a protein of approximately 114 kDa was detected in 3 out of 5 vaccinated animals' sera from 129Sv/Ev mice collected on day 21 of the vaccination schedule (FIG. 16A). In A129 mice, a CCHFv-specific IgG antibody response was detectable by Western Blot in only 1 out of 8 individual animals, which recognised a 79 kDa protein (FIG. 16B). A randomly selected A129 mouse that received the MVA-1974 negative control was tested, and no CCHFv-specific antibody response was seen (FIG. 16C).

Sera from the 8 A129 animals vaccinated with MVA-GP were also assessed by Western Blot for an early phase immune response, using a detector antibody specific for mouse IgG, IgA and IgM. Antibodies specific for a 79 kDa CCHFv protein were detected in the same individual animal in this assay, as had been detected by anti-IgG only (FIG. 16E). Broadening the sensitivity to additional antibody subclasses, detected antibodies specific for a protein of approximately 112 kDa (FIG. 16D) in a further 4 animals.

Histopathology

Figure 17:
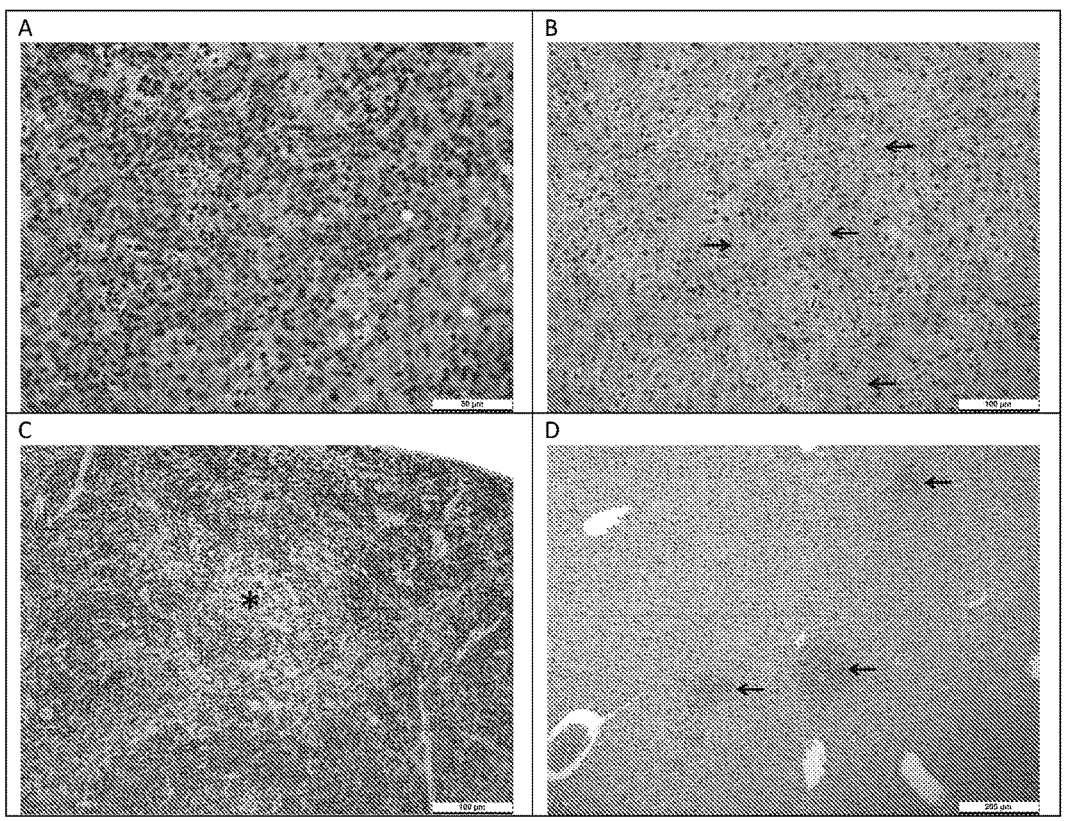
Figure 18:
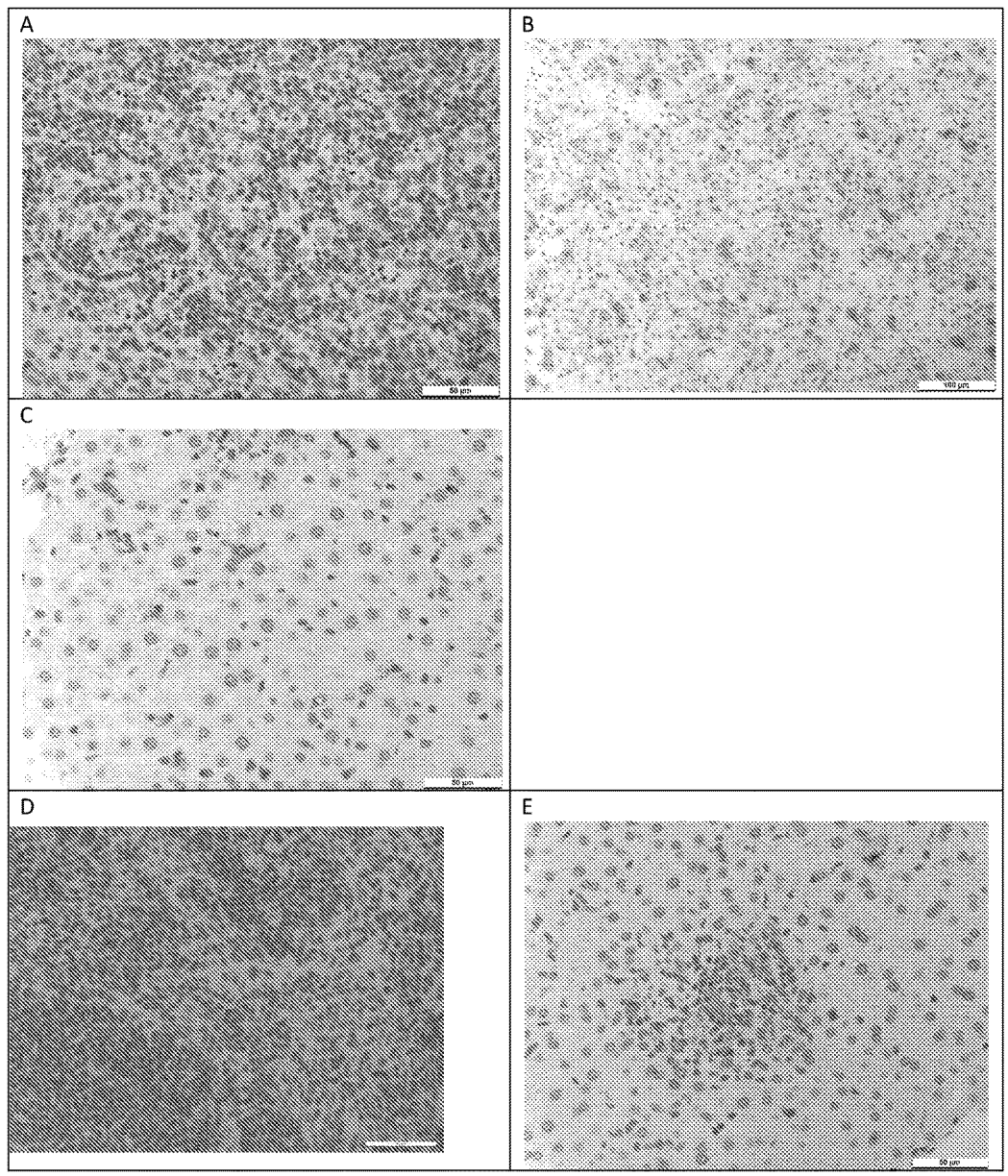

Histopathological findings in immunised, CCHFv challenged mice are shown in FIGS. 17-18 and Tables 1-2 (below).

TABLE 1

Severity of microscopic lesions in HE stained tissues from vaccinated A129 mice, challenged with CCHFv.

| | | Group | | | |
|---|---|---|---|---|---|
| | Severity | Saline (day 32-33) | MVA 1974 (day 32-33) | MVA-GP (day 32) | MVA-GP (day 42) |
| Spleen | Normal | 0 | 0 | 1 | 6 |
| | Minimal | 1 | 1 | 2 | 0 |
| | Mild | 2 | 3 | 0 | 0 |
| | Moderate | 2 | 1 | 0 | 0 |
| | Marked | 4 | 4 | 0 | 0 |
| Liver | Normal | 0 | 1 | 2 | 6 |
| | Minimal | 0 | 0 | 0 | 0 |
| | Mild | 2 | 0 | 0 | 0 |
| | Moderate | 3 | 3 | 1 | 0 |
| | Marked | 4 | 5 | 0 | 0 |

Numbers of animals in each group, according to severity rating of histological lesions.

TABLE 2

Frequency of immunohistochemically stained cells in tissues from selected vaccinated A129 mice, challenged with CCHFv.

| | | Group | | | |
|---|---|---|---|---|---|
| | Frequency | Saline (day 32-33) | MVA 1974 (day 32-33) | MVA-GP (day 32) | MVA-GP (day 42) |
| Spleen | Normal | 0 | 0 | 3 | 1 |
| | Minimal | 4 | 4 | 0 | 0 |
| | Moderate | 2 | 3 | 0 | 0 |
| | Marked | 1 | 0 | 0 | 0 |
| Liver | Normal | 0 | 0 | 2 | 1 |
| | Minimal | 1 | 2 | 1 | 0 |
| | Moderate | 3 | 1 | 0 | 0 |
| | Marked | 3 | 4 | 0 | 0 |

Numbers of animals in each group, according to frequency of cells stained by immunohistochemistry.

Viral Load Analysis

Figures 19A, 19B:
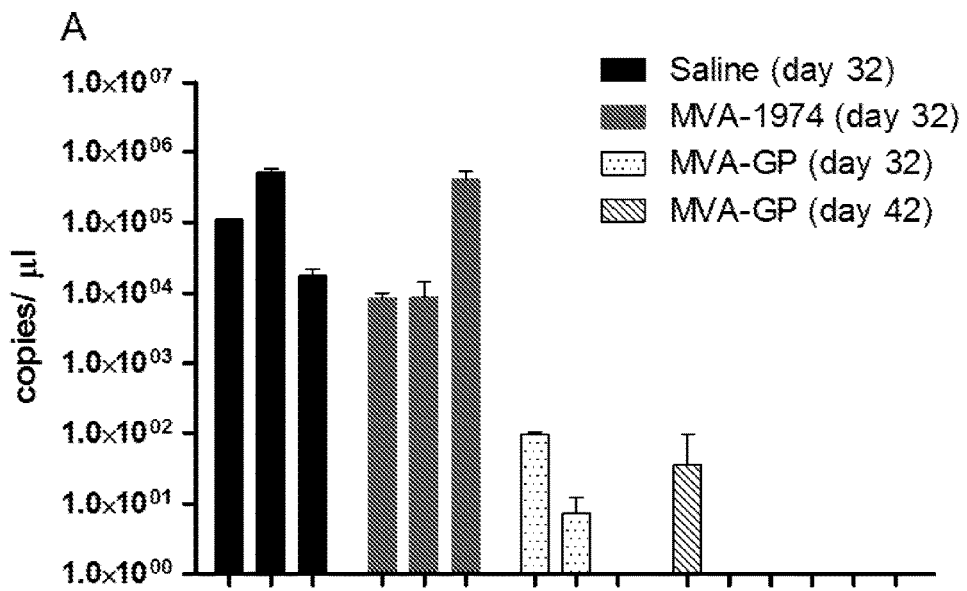
Figure 19C:
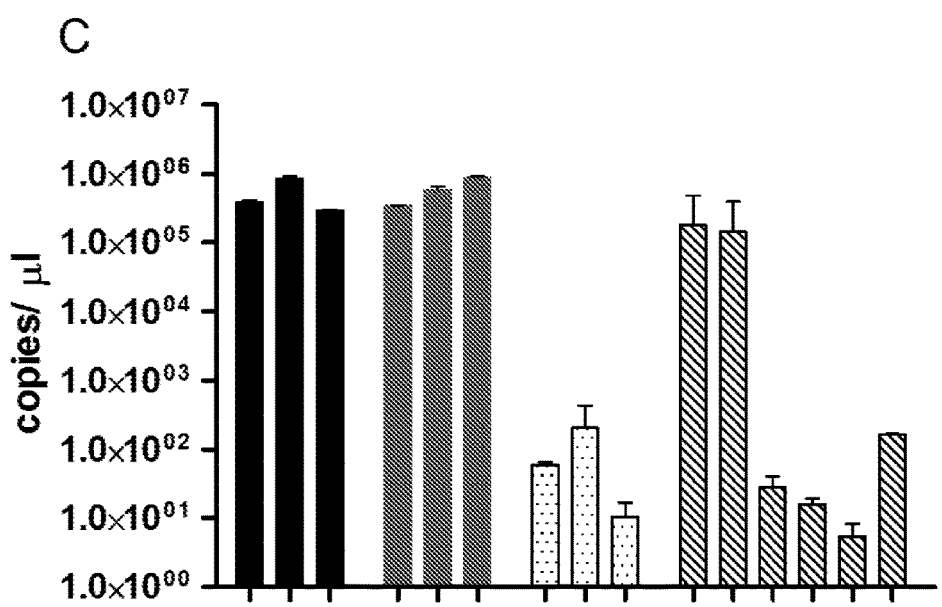

Viral load was analysed by RT-PCR of CCHFv S segment in blood, spleen, and liver from 3 animals per group at day 32, and all surviving animals at day 42. CCHFv copy number was calculated by use of a standard curve. At day 32, CCHFv copy number was significantly lower in MVA-GP vaccinated animals compared to control groups in blood, spleen and liver (p=0.05). In the blood, it was detected in only 2 of 3 animals. At day 42, CCHFv levels were not statistically different in any tissue to those in vaccinated animals at the earlier timepoint. It was detectable in the blood in only 1 out of 5 vaccinated mice (FIG. 19).

Figure 20A:
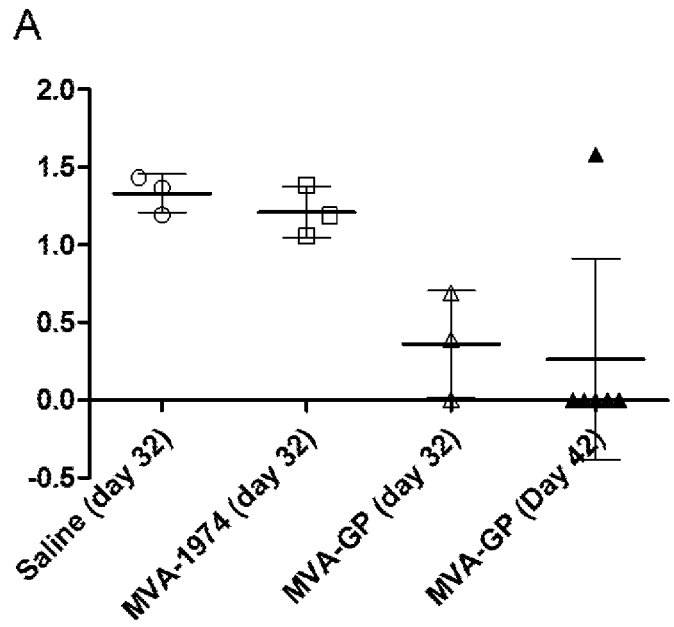
Figure 20B:
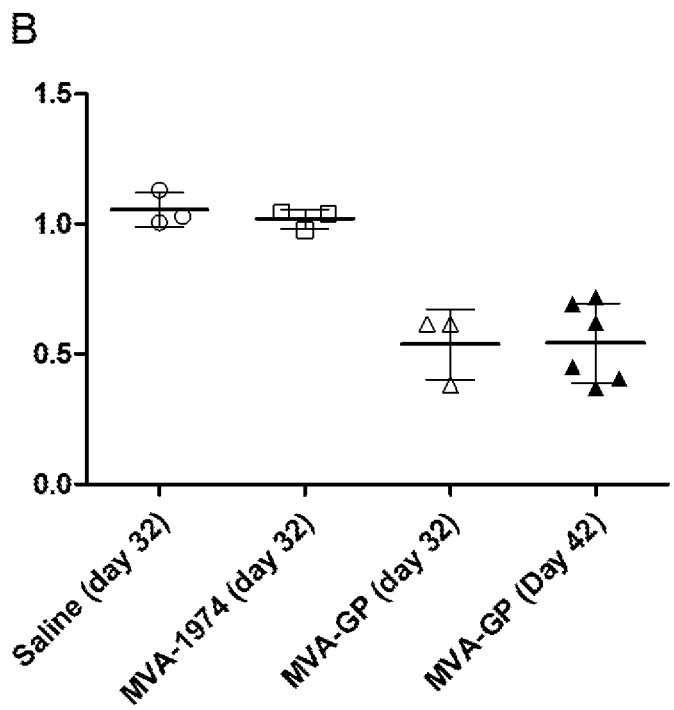
Figure 20C:
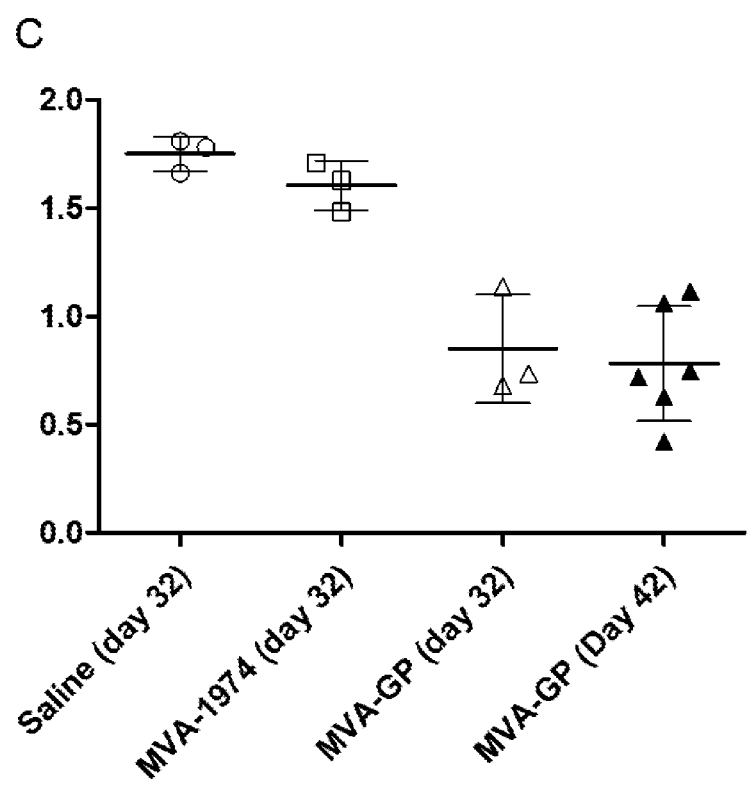

Alternatively, CCHFv expression was normalised to expression of the HPRT reference gene (FIG. 20). Normalised CCHFv expression was significantly lower in MVA-GP vaccinated animals compared to control groups in blood, spleen and liver (p=0.05). There was no statistically significant difference between saline and MVA 1974 control groups, or between day 32 and day 42 samples from MVA-GP vaccinated animals.

Conclusions:
- MVA-GP is immunogenic, producing protein-specific immune responses.
- MVA-GP is protective, protecting 100% of mice from a fully lethal challenge of homologous strain CCHF.
- Animals which reached humane clinical endpoints in the MVA-empty and saline groups exhibited signs of illness, a rise in temperature and weight loss. No such clinical signs were observed in MVA-GP vaccinated animals.

Example 5. Heterologous Prime-Boost Study

Heterologous prime-boosting approaches improve immune responses by allowing repeated vaccinations without increasing anti-vector immunity. A CCHFV glycoprotein (GP) or an antigenic fragment thereof is serially delivered via different viral or DNA vectors.

In a heterologous regime where the prime vaccination is delivered by a DNA vector, and the boost vaccination is delivered by a Fowlpox virus vector, GP-specific antibody response is increased, GP-specific T-cell response is increased, and/or clinical illness is reduced, as compared to where the prime and boost are delivered by the same vector.

The following heterologous combinations of vectors are provided for use in prime-boosting approaches:
DNA prime, MVA boost
Fowlpox prime, MVA boost
MVA prime, Fowlpox boost
DNA prime, Fowlpox boost, MVA boost
MVA prime, Adenovirus boost Example 6. Immunogenicity Studies in Non-Human Primates Prior to use in clinical trials, immune responses to a CCHF vaccine are tested in a non-human primate model.

Non-human primates (e.g. rhesus macaques or cynomolgous macaques) are inoculated with the CCHF vaccine expressing the glycoprotein gene or functional fragment thereof. Animals receive either a single dose, or multiple doses in a prime-boost regime, by a parenteral route. Subsequent immunological analysis indicates that they have generated a CCHF-specific immune response. The latter is confirmed by one or more of the following methods:
CCHF-specific antibodies present in serum
Neutralising antibodies present in serum
Cellular response to peptides derived from the CCHF glycoprotein
Cellular response to virally-infected cells.

A cellular response is characterised by an increase in one or more of: proliferation, production of cytokines or chemokines, phagocytosis, and/or release of granzymes.

Example 7. Preparation of an Example Adenovirus Vector

A non-replicating adenovirus is engineered to express a CCHF glycoprotein or partial fragment thereof. The genetic sequence for the CCHF glycoprotein is inserted into the genome of the adenovirus vector. Expression of the glycoprotein is indicated by reactivity between a glycoprotein-specific antibody and products from the adenovirus by Western blotting or ELISA as follows:

Cellular lysate of cells infected with the recombinant adenovirus, subjected to SDS-PAGE and Western blotting with an antibody specific for the CCHF glycoprotein, show a specific reactivity compared to negative controls.

Alternatively, products from cells infected with the recombinant adenovirus are used to coat an ELISA plate. CCHF-specific antibodies bind to the coating and are detected via a chemical reaction.

Example 8. CCHF Vaccine Provides Cross-Strain Protection

A vaccine expressing the glycoprotein gene or functional fragment thereof, in an adenovirus or non-replicating poxvirus vector, is delivered via a parenteral route into mice that are susceptible to disease caused by CCHF virus. They are challenged with a lethal dose of CCHF virus, from a strain other than that on which the vaccine is based. The challenged animals show no or mild clinical signs of illness, and do not require euthanasia. Control animals which received the same challenge dose of CCHF, but did not receive the vaccine, show severe signs of illness, reach humane clinical endpoints and require euthanasia.

Example 9. MVA-GP Immunogenicity in A129 Mice

Twenty-five A129 mice were injected intramuscularly with $10^7$ pfu per animal of MVA-GP, prepared according to Example 1. A volume of 100 μl was delivered, split into two sites at 50 μl each. Animals received 2 vaccinations, spaced 2 weeks apart. Control animals (n=25) received $10^7$ pfu per animal of non-recombinant MVA 1974/NIH clone 1 according to the same regime.

Fourteen days after the final vaccination, all mice were sacrificed for antibody testing. Sera were prepared, heat-inactivated and pooled; each pool contained sera from 5-6 animals that received the same treatment as each other. Pools were subjected to Western blot analysis against lysate of cells infected with CCHF virus.

In 4 out of 5 pools from animals that received MVA-GP, an IgG antibody response specific for a CCHF virus protein of approximately 114 kDa was detected (FIG. 16F).

Example 10. Preparation and Efficacy of a Recombinant Influenza Virus Vector Reverse genetics are used to construct a recombinant influenza virus that carries a protective epitope of CCHFv glycoprotein in the neuraminidase stalk. CCHFv specific cytotoxic T lymphocytes (CTLs) are induced in mice after intranasal or parenteral administration. These CTLs provide a reduction in viral load and clinical illness after challenge with CCHFv.

Example 11. Preparation and Efficacy of a Recombinant Bacterial Vector

The CCHFv glycoprotein gene, or functional fragment thereof, is expressed on the surface of genetically attenuated, gram-negative bacteria. After intranasal or parenteral administration to mice, the bacterial vector colonises antigen-presenting cells (e.g. dendritic cells or macrophages). A humoral and cellular CCHFv-specific immune response is induced. These immune responses provide a reduction in viral load and clinical illness after challenge with CCHFv.

The invention claimed is:

1. A non-replicating poxvirus vector for inducing a protective immune response in a subject against Crimean-Congo Haemorrhagic Fever Virus (CCHFV), wherein said vector comprises a nucleic acid sequence encoding a CCHFV glycoprotein or antigenic fragment thereof and wherein the non-replicating poxvirus vector comprises a Modified Vaccinia virus Ankara (MVA) vector and wherein the nucleic acid sequence encoding a CCHFV glycoprotein encodes one or more of: a CCHFV $G_N$ glycoprotein, a CCHFV $G_C$ glycoprotein, and a CCHFV M segment polyprotein.

2. The vector of claim 1, wherein the nucleic acid sequence encoding a CCHFV glycoprotein or antigenic fragment thereof comprises a nucleic acid sequence having at least 70% sequence identity to a nucleic acid sequence selected from SEQ ID NOs: 1, 2, and 3.

3. A composition comprising a vector according to claim 1, and a pharmaceutically-acceptable carrier.

4. The composition of claim 3, further comprising an adjuvant.

5. A non-replicating poxvirus vector comprising a Modified Vaccinia virus Ankara (MVA) vector for inducing a protective immune response in a subject against Crimean-Congo Haemorrhagic Fever Virus (CCHFV), wherein said vector comprises a nucleic acid sequence encoding a CCHFV glycoprotein or antigenic fragment thereof and wherein the nucleic acid sequence encoding a CCHFV glycoprotein or antigenic fragment thereof comprises a nucleic acid sequence having at least 70% sequence identity to a nucleic acid sequence selected from SEQ ID NOs: 1, 2, and 3.

6. A non-replicating poxvirus vector comprising a Modified Vaccinia virus Ankara (MVA) vector for inducing a protective immune response in a subject against Crimean-Congo Haemorrhagic Fever Virus (CCHFV), wherein said vector comprises a nucleic acid sequence encoding a CCHFV glycoprotein or antigenic fragment thereof and wherein the nucleic acid sequence encoding a CCHFV glycoprotein encodes one or more of: a CCHFV $G_N$ glycoprotein, a CCHFV $G_C$ glycoprotein, and a CCHFV M segment polyprotein.

7. A nucleic acid sequence encoding a viral vector according to claim 1.

8. A method of making a viral vector, comprising:
providing a nucleic acid, wherein the nucleic acid comprises a nucleic acid sequence encoding a vector according to claim 1;
transfecting a host cell with the nucleic acid;
culturing the host cell under conditions suitable for the propagation of the vector; and
obtaining the vector from the host cell.

9. A host cell comprising the nucleic acid sequence of claim 8.

10. A method of inducing an immune response to a patient in need thereof comprising: administering the composition of claim 1.

11. A method of inducing an immune response in a subject against CCHFV, said method comprising administering to said subject a composition according to claim 3.

12. The method according to claim 11, wherein the immune response comprises a T cell response.

13. A method of preventing or treating a CCHFV infection in a subject, said method comprising administering to said subject a composition according to claim 3.

* * * * *